US012723024B2

(12) United States Patent
Kristensen et al.

(10) Patent No.: US 12,723,024 B2
(45) Date of Patent: Sep. 1, 2026

(54) ACID ADDITION SALTS OF (S)-3-(2,5-DIMETHOXY-4-(TRIFLUOROMETHYL) PHENYL)PIPERIDINE AND (S)-3-(2-METHOXY-5-(METHYLTHIO)-4-(TRIFLUOROMETHYL) PHENYL)PIPERIDINE, SPECIFIC POLYMORPHS THEREOF AND METHODS FOR THEIR MANUFACTURE

(71) Applicant: LOPHORA APS, Charlottenlund (DK)

(72) Inventors: Jesper Langgaard Kristensen, Copenhagen N (DK); Emil Märcher-Rørsted, Copenhagen S (DK)

(73) Assignee: LOPHORA APS, Charlottenlund (DK)

( * ) Notice: Subject to any disclaimer, the term of this patent is extended or adjusted under 35 U.S.C. 154(b) by 405 days.

(21) Appl. No.: 18/556,295

(22) PCT Filed: May 5, 2022

(86) PCT No.: PCT/EP2022/062142

§ 371 (c)(1),
(2) Date: Oct. 19, 2023

(87) PCT Pub. No.: WO2022/234010

PCT Pub. Date: Nov. 10, 2022

(65) Prior Publication Data

US 2024/0208903 A1 Jun. 27, 2024

(30) Foreign Application Priority Data

May 6, 2021 (EP) .................................... 21172539

(51) Int. Cl.
*C07D 211/02* (2006.01)
*C07D 211/12* (2006.01)

(52) U.S. Cl.
CPC .......... *C07D 211/02* (2013.01); *C07D 211/12* (2013.01)

(58) Field of Classification Search
CPC ............................ C07D 211/02; C07D 211/12
USPC .......................................................... 546/10
See application file for complete search history.

(56) References Cited

U.S. PATENT DOCUMENTS

2016/0185752 A1 6/2016 Bousba
2021/0032219 A1 2/2021 Yu et al.
2021/0137908 A1 5/2021 Kristensen et al.

*Primary Examiner* — Kahsay Habte

(74) *Attorney, Agent, or Firm* — DUANE MORRIS LLP; Gregory M. Lefkowitz; Brandon A. Chan

(57) ABSTRACT

The present invention relates to certain pharmaceutically acceptable salts of (S)-3-(2,5-dimethoxy-4-(trifluoromethyl) phenyl)piperidine and (S)-3-(2-methoxy-5-(methylthio)-4-(trifluoromethyl) phenyl)piperidine and specific polymorphs thereof. More particularly, the present invention relates to the compounds of Formula (VI) as well as chemical routes for their manufacture.

23 Claims, 3 Drawing Sheets

ACID ADDITION SALTS OF (S)-3-(2,5-DIMETHOXY-4-(TRIFLUOROMETHYL)PHENYL)PIPERIDINE AND (S)-3-(2-METHOXY-5-(METHYLTHIO)-4-(TRIFLUOROMETHYL)PHENYL)PIPERIDINE, SPECIFIC POLYMORPHS THEREOF AND METHODS FOR THEIR MANUFACTURE

CROSS-REFERENCE TO RELATED APPLICATIONS

This application is a § 371 national stage entry of International Application No. PCT/EP2022/062142, filed May 5, 2022, which claims priority to European Application No. 21172539.5, filed May 6, 2021, the entire contents of which are incorporated herein by reference.

FIELD OF THE INVENTION

The present invention relates to certain pharmaceutically acceptable salts of (S)-3-(2,5-dimethoxy-4-(trifluoromethyl)phenyl)piperidine and (S)-3-(2-methoxy-5-(methylthio)-4-(trifluoromethyl) phenyl)piperidine and specific polymorphs thereof that possess e.g. high crystallinity, high solubility, high stability, and good thermal properties. The present invention also relates to new routes for the manufacture of such salts and polymorphs.

BACKGROUND OF THE INVENTION

Recent research efforts (see PCT/EP2020/081357) have shown that a new class of 3-(2,4,5-trisubstituted-phenyl) piperidines, 3-(2,4-disubstituted-phenyl)piperidines or 3-(3,4-disubstituted-phenyl)piperidines acts as 5-$HT_{2A}$ agonists and that this class of compounds holds tremendous potential for the treatment of depression, in particular treatment-resistant depression. Therefore, there is a need to develop these compounds into an active pharmaceutical ingredient (API) that is suitable for use in drug manufacturing. Compound properties, such as solubility, hygroscopicity, crystallinity, and chemical/physical stability are of uttermost importance in drug development in order to obtain a safe and effective drug. Salt formation is a common method for improving e.g. the solubility, dissolution rate, hygroscopicity, crystallinity, stability, and even the toxicity of drugs. Hence, in order to develop a compound into an API for drug manufacturing, salt screening in various solvents is needed to identify suitable salt forms and stable polymorphs (i.e. different crystal lattice) thereof. Polymorphs often show marked differences in solubility, crystallinity, dissolution rate, and stability. Therefore, it is highly important to characterize different salts and specific polymorph forms to ensure that the polymorph is stable both during manufacturing and during the shelf life of the drug. Thus, in one aspect the present invention sets out to solve the problem of providing specific salts and polymorph forms of (S)-3-(2,5-dimethoxy-4-(trifluoromethyl)phenyl)piperidine and (S)-3-(2-methoxy-5-(methylthio)-4-(trifluoromethyl)phenyl) piperidine which are suitable for drug manufacturing.

Medicinal chemistry routes for the synthesis of new compounds often focus on diversity in order to access different analogues fast in small scale. In contrast, process chemistry routes for the manufacture of an API on industrial scale necessitate that factors such as scalability, overall yield, safety, environmental hazards, economy, and overall feasibility of the route be taken into account.

Thus, in another aspect, the present invention solves the problem of providing a scalable and efficient process chemistry route for the manufacture of the specific salts and polymorph forms of (S)-3-(2,5-dimethoxy-4-(trifluoromethyl)phenyl)piperidine and (S)-3-(2-methoxy-5-(methylthio)-4-(trifluoromethyl)phenyl)piperidine disclosed herein.

SUMMARY OF THE INVENTION

In a first aspect, the present invention relates to a method for the manufacture of a compound of Formula (VI) comprising the step of:

a) reacting the compound of Formula (III), wherein PG is an amine protecting group, (III)

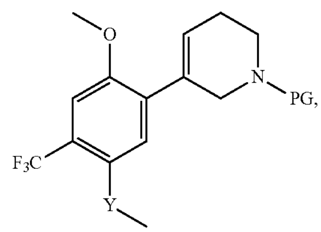

in a solvent with hydrogen gas ($H_2$) in the presence of a transition metal catalyst to obtain a racemic compound of Formula (IVa) or (IVb)

(IVa)

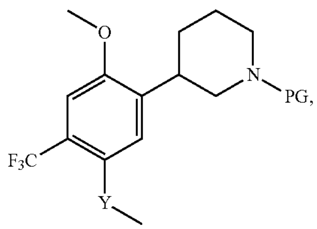

(IVb)

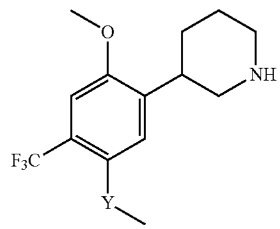

or alternatively, reacting the compound of Formula (III) in a solvent, with a deprotection reagent to obtain a compound of Formula (IIIa), (IIIa)

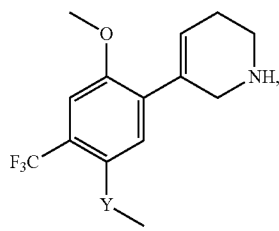

b) reacting the compound of Formula (IVa), if formed in step a), in a solvent with a deprotection reagent to obtain a racemic compound of Formula (IVb), or alternatively, reacting the compound of Formula (IIIa) in a solvent, if formed in step a), with hydrogen gas ($H_2$) in the presence of a transition metal catalyst to obtain a racemic compound of Formula (IVb)

(IVb)

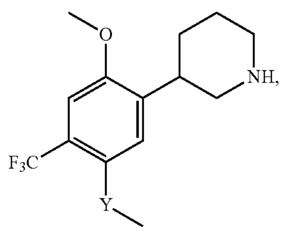

c) reacting a compound of Formula (IVb) with a chiral acid in a solvent to obtain a compound of Formula (V) having an enantiomeric excess (ee) of at least 70%, (V)

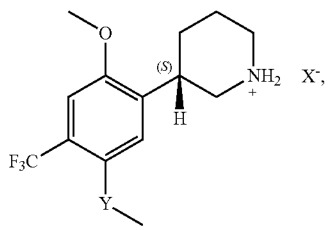

wherein $X^-$ is the conjugate base of the chiral acid, and liberating the salt of Formula (V) to obtain the compound of Formula (S)-(IVb)

(S)-(IVb)

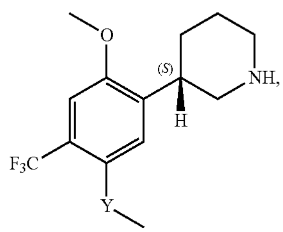

d) reacting the compound of Formula (S)-(IVb) in a solvent with succinic acid, L-tartaric acid, or HCl to obtain a crystalline compound of Formula (VI), (VI)

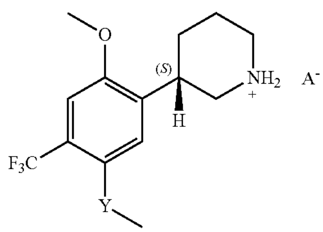

wherein

Y is selected from S or O, $A^-$ is selected as 3-carboxypropanoate, (2R,3R)-3-carboxy-2,3-dihydroxypropanoate or chloride ($Cl^-$).

In a second aspect, the present invention relates to a method for the manufacture of a compound of Formula (VI) comprising the step of:

a) reacting the compound of Formula (III), wherein PG is an amine protecting group, (III)

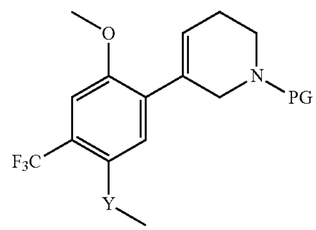

in a solvent with hydrogen gas ($H_2$) in the presence of a transition metal catalyst, and a chiral ligand, to obtain a compound of Formula (S)-(IVa) or (S)-(IVb), having an enantiomeric excess (% ee) of at least 70%, (S)-(IVa)

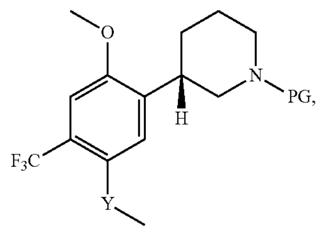

(S)-(IVb)

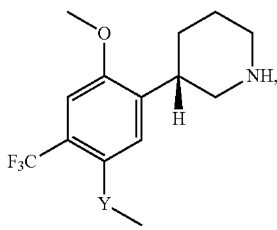

or alternatively, reacting the compound of Formula (III) in a solvent, with a deprotection reagent to obtain a compound of Formula (IIIa)

(IIIa)

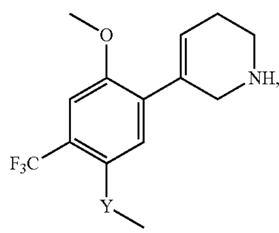

b) reacting the compound of Formula (S)-(IVa), if formed in step a), in a solvent with a deprotection reagent to obtain a compound of Formula (S)-(IVb) having an enantiomeric excess (% ee) of at least 70%, or alternatively, reacting the compound of Formula (IIIa), if formed in step a), in a solvent with hydrogen gas ($H_2$) in the presence of a transition metal catalyst and a chiral ligand, to obtain a compound of Formula (S)-(IVb), having an enantiomeric excess (% ee) of at least 70%, (S)-(IVb)

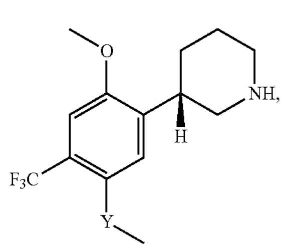

c) reacting the compound of Formula (S)-(IVb) in a solvent with succinic acid, L-tartaric acid, or HCl to obtain a crystalline compound of Formula (VI), (VI)

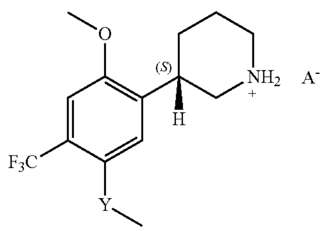

wherein $A^-$ is selected as 3-carboxypropanoate, (2R,3R)-3-carboxy-2,3-dihydroxypropanoate or chloride ($Cl^-$).

In a Third Aspect, the Invention Relates to a Crystalline Compound of Formula (VI), (VI)

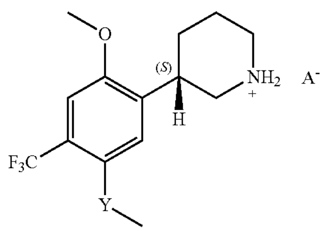

wherein Y is selected from O or S, $A^-$ is selected as 3-carboxypropanoate, (2R,3R)-3-carboxy-2,3-dihydroxypropanoate or $Cl^-$.

In a fourth aspect, the invention relates to intermediates of Formula (III) or (IIIa), (III)

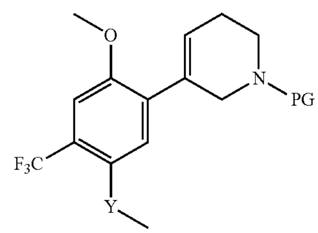

-continued (IIIa)

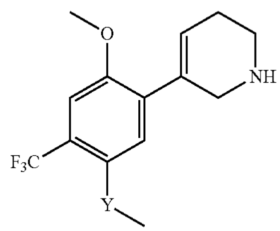

wherein Y is selected from O or S,

PG is an amine protecting group.

In a fifth aspect, the invention relates to the use of intermediates of Formula (III) for the manufacture of compounds of Formula (IVa), (IVb), (IIIa), (S)-(IVa), (S)-(IVb), (V), or (VI) or use of intermediates of Formula (IIIa) for the manufacture of compounds of Formula (IVb), (S)-(IVb), (V), or (VI).

DETAILED DESCRIPTION OF THE INVENTION

Figure 1:
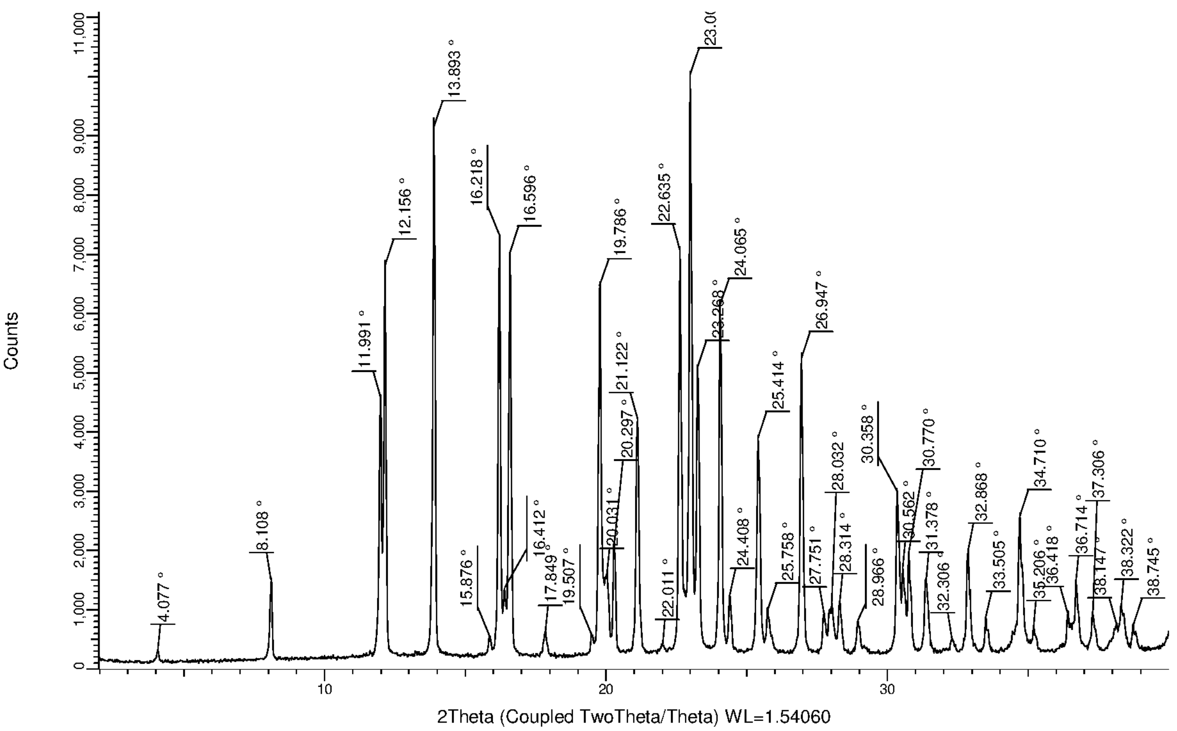
FIG. 1 shows the XPRD spectrum of polymorph A of the compound of Formula (VI), wherein Y is O and wherein $A^-$ is 3-carboxypropanoate (i.e. 1:1 salt formed between (S)-3-(2,5-dimethoxy-4-(trifluoromethyl)phenyl)piperidine and succinic acid).

The present invention relates to certain advantageous pharmaceutically acceptable salts of (S)-3-(2,5-dimethoxy-4-(trifluoromethyl)phenyl)piperidine and (S)-3-(2-methoxy-5-(methylthio)-4-(trifluoromethyl)phenyl)piperidine and specific polymorphs thereof. The present invention also relates to new routes for the manufacture of these salts and polymorphs on large scale.

Particularly, the inventors found that the succinic acid salt of (S)-3-(2,5-dimethoxy-4-(trifluoromethyl)phenyl)piperidine (i.e. the 1:1 salt formed between (S)-3-(2,5-dimethoxy-4-(trifluoromethyl)phenyl)piperidine and succinic acid), the L-tartaric acid salt of (S)-3-(2,5-dimethoxy-4-(trifluoromethyl)phenyl)piperidine (i.e. 1:1 salt formed between (S)-3-(2,5-dimethoxy-4-(trifluoromethyl)phenyl)piperidine and L-tartaric acid) and the HCl salt of (S)-3-(2,5-dimethoxy-4-(trifluoromethyl)phenyl)piperidine showed properties that were improved compared to other salts of (S)-3-(2,5-dimethoxy-4-(trifluoromethyl)phenyl)piperidine and (S)-3-(2,5-dimethoxy-4-(trifluoromethyl)phenyl)piperidine as the free base. Thus, these salts were found to be suitable for the development of an API. In particular, the succinic acid salt of (S)-3-(2,5-dimethoxy-4-(trifluoromethyl)phenyl)piperidine (1:1) and the HCl salt of (S)-3-(2,5-dimethoxy-4-(trifluoromethyl)phenyl)piperidine were found to be promising salt candidates.

Aspect I

In a first aspect, the present invention relates to a method for the manufacture of a compound of Formula (VI) comprising the step of:

a) reacting the compound of Formula (III), wherein PG is an amine protecting group, (III)

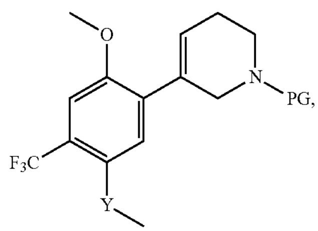

in a solvent with hydrogen gas ($H_2$) in the presence of a transition metal catalyst to obtain a racemic compound of Formula (IVa) or (IVb)

(IVa)

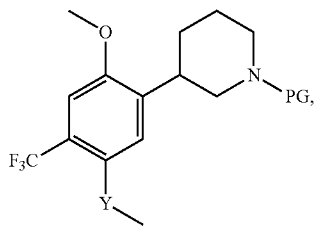

(IVb)

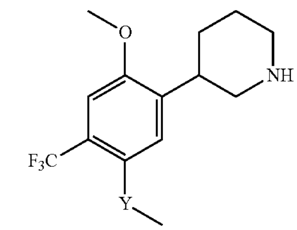

or alternatively, reacting the compound of Formula (III) in a solvent, with a deprotection reagent to obtain a compound of Formula (IIIa), (IIIa)

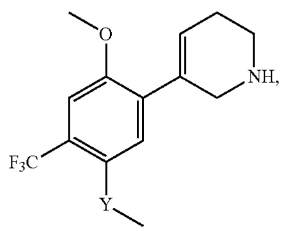

b) reacting the compound of Formula (IVa), if formed in step a), in a solvent with a deprotection reagent to obtain a racemic compound of Formula (IVb), or alternatively, reacting the compound of Formula (IIIa), if formed in step a), in a solvent with hydrogen gas ($H_2$) in the presence of a transition metal catalyst to obtain a racemic compound of Formula (IVb)

(IVb)

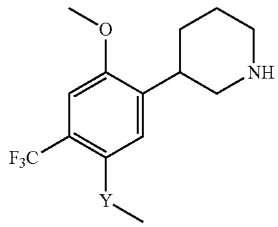

c) reacting a compound of Formula (IVb) with a chiral acid in a solvent to obtain a compound of Formula (V) having an enantiomeric excess (ee) of at least 70%, (V)

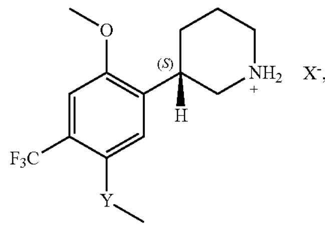

wherein $X^-$ is the conjugate base of the chiral acid, and liberating the salt of Formula (V) to obtain the compound of Formula (S)-(IVb)

(S)-(IVb)

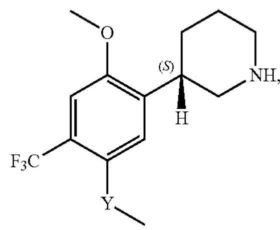

d) reacting the compound of Formula (S)-(IVb) in a solvent with succinic acid, L-tartaric acid, or HCl to obtain a crystalline compound of Formula (VI), (VI)

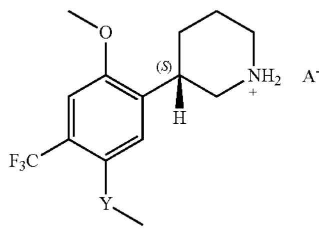

wherein

Y is selected from S or O, $A^-$ is selected as 3-carboxypropanoate, (2R,3R)-3-carboxy-2,3-dihydroxypropanoate or chloride ($Cl^-$).

In an embodiment of the invention, the method further comprises the step a1), prior to step a), of:

a1) reacting a compound of Formula (I) with a compound of Formula (II) in a solvent, (I)

(II)

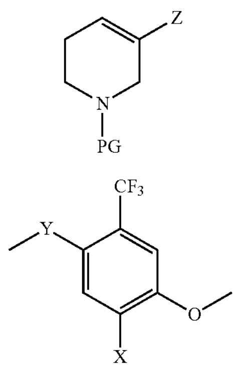

wherein Z is selected from the group consisting of a boronic acid, a trifluoroborate salt and boronic esters, PG is an amine protecting group, Y is selected from S or O, X is selected from Cl, Br, I or OTf, in the presence of a base and a transition metal catalyst to obtain a compound of Formula (III)

(III)

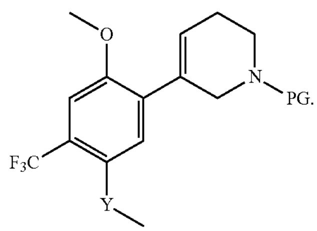

Thus, in a preferred embodiment, the present invention relates to a method for the manufacture of a compound of Formula (VI), comprising the steps of:

a1) reacting a compound of Formula (I) with a compound of Formula (II) in a solvent, (I)

(II)

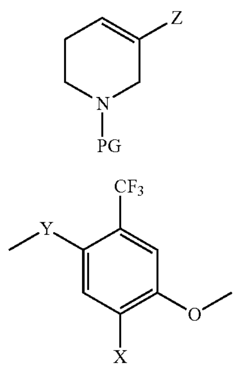

Wherein Z is selected from the group consisting of a boronic acid, a trifluoroborate salt, and boronic esters, PG is an amine protecting group, Y is selected from S or O, X is selected from Cl, Br, I, or OTf, in the presence of a base and a transition metal catalyst to obtain a compound of Formula (III)

(III)

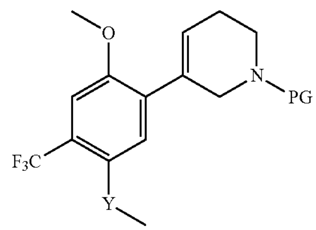

a) reacting the compound of Formula (III) in a solvent with hydrogen gas ($H_2$) in the presence of a transition metal catalyst to obtain a racemic compound of Formula (IVa) or (IVb)

(IVa)

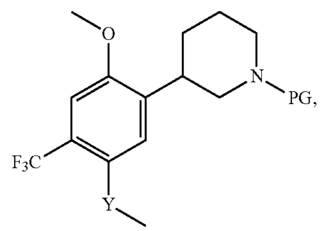

(IVb)

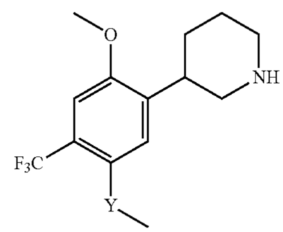

b) reacting the compound of Formula (IVa), if formed in step 1), in a solvent with a deprotection reagent to obtain a compound of Formula (IVb), (IVb)

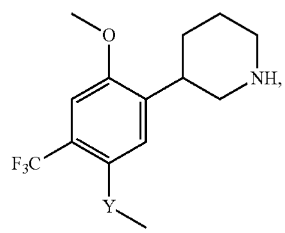

c) reacting a compound of Formula (IVb) in a solvent with a chiral acid to obtain a compound of Formula (V) having an enantiomeric excess (ee) of at least 70%, (V)

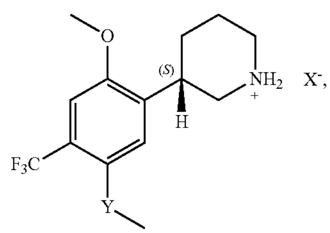

wherein $X^-$ is the conjugate base of the chiral acid, and liberating the salt of Formula (V) to obtain the compound of Formula (S)-(IVb)

(S)-(IVb)

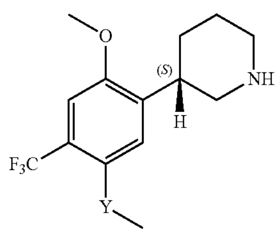

d) reacting the compound of Formula (S)-(IVb) in a solvent with succinic acid, L-tartaric acid, or HCl to obtain a crystalline compound of Formula (VI), (VI)

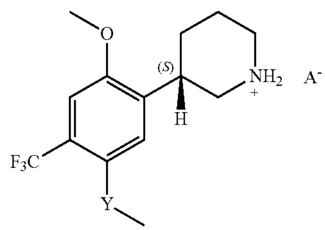

wherein $A^-$ is selected as 3-carboxypropanoate, (2R,3R)-3-carboxy-2,3-dihydroxypropanoate or chloride ($Cl^-$).

The hydrogenation and the deprotection step may be reversed such that the deprotection is performed prior to the hydrogenation.

Thus, in more preferred embodiment, the present invention relates to a method for the manufacture of a compound of Formula (VI) comprising the steps of:

a1) reacting a compound of Formula (I) with a compound of Formula (II) in a solvent, (I)

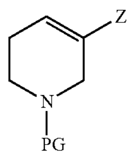

-continued (II)

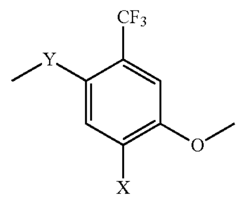

wherein Z is selected from the group consisting of a boronic acid, a trifluoroborate salt and boronic esters, PG is an amine protecting group, Y is selected from S or O, X is selected from Cl, Br, I or OTf, in the presence of a base and a transition metal catalyst to obtain a compound of Formula (III)

(III)

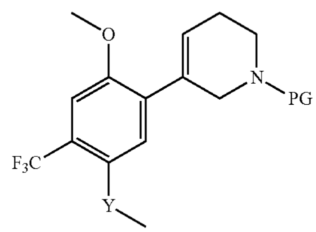

a) reacting the compound of Formula (III) in a solvent, with a deprotection reagent to obtain a compound of Formula (IIIa), (IIIa)

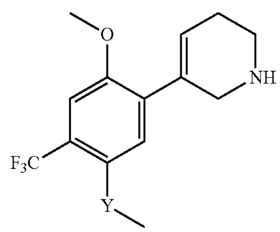

b) reacting the compound of Formula (IIIa) in a solvent with hydrogen gas ($H_2$) in the presence of a transition metal catalyst to obtain a racemic compound of Formula (IVb)

(IVb)

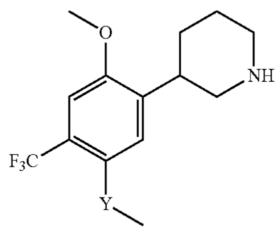

c) reacting a compound of Formula (IVb) in a solvent with a chiral acid to obtain a compound of Formula (V) having an enantiomeric excess (ee) of at least 70%, (V)

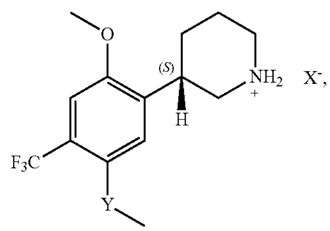

wherein $X^-$ is the conjugate base of the chiral acid, and liberating the salt of Formula (V) to obtain the compound of Formula (S)-(IVb)

(S)-(IVb)

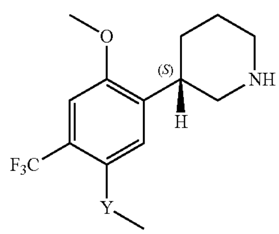

d) reacting the compound of Formula (S)-(IVb) in a solvent with succinic acid, L-tartaric acid, or HCl to obtain the compound of Formula (VI), (VI)

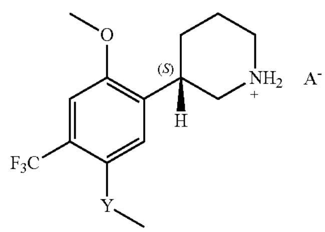

wherein

Y is selected from S or O, $A^-$ is selected as 3-carboxypropanoate, (2R,3R)-3-carboxy-2,3-dihydroxypropanoate or chloride ($Cl^-$).

Step a1). Suzuki-Miyaura Cross-Couplinq (SMC)

Step a1) of the process according to the first aspect is an SMC reaction between a compound of Formula (I) and a compound of Formula (II) in a solvent in the presence of a base and a transition metal catalyst. Other suitable cross-couplings may also be employed in step a1) e.g. Negishi couplings, Stille couplings, or Hiyama couplings by replacing the organoboron (i.e. compound of Formula (I)) with a suitable organozinc, organostannane, or organosilane instead. Organozincs, organostannanes, or organosilanes may be prepared by conventional methods known in the art.

Compound of Formula (I): Boronic acids (R—B(OH)$_2$), trifluoroborate salts (R—BF$_3$K i.e. Molander salts) and various boronic esters (R—B(OR)$_2$), such as pinacol boroates, cathechol boronates, trimethylene glycol boronates, MIDA boronates, and triisopropyl boronates, may be employed in the SMC reaction in step a1). In an embodiment of the invention, Z in Formula (I) is selected from the group consisting of a boronic acid, a trifluoroborate salt, and a boronic ester. In the most preferred embodiment, Z is selected as a pinacol boronate. Various protecting groups may be used for the amine in the compound of Formula (I). Common amine protecting groups include carbamates, such as 9-Fluorenylmethyl carbamate (Fmoc-NR$_2$), t-Butyl carbamate (Boc-NR$_2$), and Benzyl carbamate (Cbz-NR$_2$), amides, such as acetamide (Ac—NR$_2$) and Trifluoroacetamide (CF$_3$CO—NR$_2$); Benzylamines, such as Benzylamine (Bn-NR$_2$) or 4-methoxybenzylamine (PMB-NR$_2$); Triphenylmethylamine (Tr-NR$_2$); Benzylideneamine; and Sulfonamides, such as p-Toluenesulfonamide (Ts-NR$_2$). In an embodiment, the protecting group is a 9-Fluorenylmethyl carbamate (Fmoc-NR$_2$), t-Butyl carbamate (Boc-NR$_2$), or Benzyl carbamate (Cbz-NR$_2$). In another embodiment, the protecting group is an acetamide (Ac—NR$_2$) or trifluoroacetamide (CF$_3$CO—NR$_2$). In yet another embodiment, the protecting group is a benzylamine (Bn-NR$_2$) or 4-methoxybenzylamine (PMB-NR$_2$). In yet another embodiment, the protecting group is a triphenylmethylamine (Tr-NR$_2$). In yet another embodiment, the protecting group is a p-Toluenesulfonamide (Ts-NR$_2$). Standard conditions for protection and deprotection may be found in e.g. Greene's Protective Groups in organic synthesis. Preferably, the protecting group (PG) is a carbamate protecting group, such as Boc (t-Butyloxycarbonyl) or CBz (carboxybenzyl). A Boc protecting group has the benefit that it can be removed under acidic conditions with concomitant salt formation. This may in certain embodiments allow for a one-pot deprotection, precipitation, and isolation of the product. A CBz protecting group has the benefit that deprotection and reduction of the alkene (i.e. the double bond in piperidine) in the compound of Formula (III) may be performed in a single step such that a separate deprotection step (i.e. step a or b) is not needed. In some embodiments, the SMC reaction may be performed without the use of an amine protecting group in the compound of Formula (I) (i.e. a compound of Formula I, wherein PG=H) such that a deprotection step (i.e. step a or b) is not needed. In the most preferred embodiment, the compound of Formula (I) is the compound of Formula (Ia). The compound of Formula (Ia) has previously been described and is commercially available [CAS Number 885693-20-9].

(Ia)

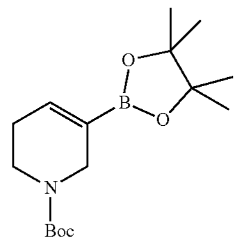

Compound of formula (II): Aryl halides (chloro, bromo or iodo) or pseudohalides (e.g., sulfonates such as triflate, 4-fluorobenzenesulfonate, sulfurofluoridate, mesylate, tosylates, nonaflate, 1H-imidazole-1-sulfonate) may be employed in the SMC reaction in step a1). Thus, in an embodiment of the invention, the compound of Formula (II) is 1-chloro-2,5-dimethoxy-4-(trifluoromethyl)benzene or (5-chloro-4-methoxy-2-(trifluoromethyl)phenyl)(methyl) sulfane. In another embodiment of the invention, the compound of Formula (II) is 1-iodo-2,5-dimethoxy-4-(trifluoromethyl)benzene or (5-iodo-4-methoxy-2-(trifluoromethyl) phenyl)(methyl)sulfane. In the most preferred embodiment of the invention, the compound of Formula (II) is 1-bromo- 2,5-dimethoxy-4-(trifluoromethyl)benzene or (5-bromo-4-methoxy-2-(trifluoromethyl)phenyl)(methyl) sulfane. These compounds are previously described in e.g. Angew. Chem. Volume 50, Issue 8, Feb. 18, 2011, pages 1896-1900, and are commercially available through various vendors or may be prepared in few steps from commercially available starting materials as illustrated herein.

Base: A large number of bases have been successfully employed in the SMC reaction. The base aids in the generation of the more reactive boron-ate complex. Typical bases for SMC include carbonate bases, phosphate bases, alkoxide bases, hydroxide bases, or amine bases. In an embodiment of the invention, the base is selected from a carbonate base, such as $Na_2CO_3$, $K_2CO_3$, $Cs_2CO_3$, $MgCO_3$ or $CaCO_3$, a phosphate base such as $K_3PO_4$, an alkoxide base such as KOtBu, a hydroxide base such as NaOH or KOH, a carboxylate base such as KOAc, or an amine base such as triethylamine. In the most preferred embodiment, the base is $K_2CO_3$. Typically, the base is added in excess, such as from 1.2 eq. to 10 eq. In the most preferred embodiment of the invention, 2 eq. of the base is added.

Catalyst: Various transition metal catalysts have been successful employed in the SMC reaction. Typically, such catalysts rely on the transition metals palladium or nickel. Examples of such palladium catalysts include but are not limited to $Pd(dba)_2$, $Pd(acac)_2$, $Pd(PPh_3)_4$, $Pd(Cl_2)(dppf)$, $Pd(CI)_2$, $Pd(OAc)_2$. The palladium in the catalyst may be present in the required oxidation state (i.e. $Pd^0$ as in e.g. $Pd(dba)_2$) or the palladium may be in present in a higher oxidation state (i.e. $Pd^{+2}$ as in e.g. $Pd(OAc)_2$) and reduced in situ to $Pd^0$ by e.g. the base, aryl boronic acid or phosphine ligand employed. Various phosphine ligands may be added in the SMC reaction to form the active catalyst. Such phosphine ligands include but are not limited to phosphine ligands selected from the list consisting of $PPh_3$, $PCy_3$, $P(o\text{-tolyl})_3$, $P(iPr)_3$, $P(O—Pr\text{-}i)_3$, n-BuP(1-Ad)$_2$, P(t-Bu)$_2$(p-NMe$_2$-Ph), DavePhos, JophnPhos, SPhos, XPhos, RuPhos, DPPF, DPPE and DPPP. Likewise, a range of nickel catalysts may be employed. Such catalysts include but are not limited to the list consisting of $Ni(acac)_2$, $Ni(COD)_2$, $Ni(dppf)Cl_2$, $NiCl_2$ optionally in the presence of the phosphine ligands mentioned above. Further examples of suitable Pd/Ni catalysts and suitable ligands for the SMC reaction may be found in e.g. the textbook Suzuki-Miyaura Cross-Coupling Reaction and Potential Applications, 2018 (ISBN: 3038425567, 9783038425564). In the most preferred embodiment, the catalyst is $Pd(dppf)Cl_2$. Catalyst loadings in the SMC is typically employed in the range of 0.15-0.001 eq., such as in the range of 0.10-0.005 eq., preferably in the range of 0.07-0.01 eq., more preferably 0.05-0.02 eq. In the most preferred embodiment, the catalyst is $Pd(dppf)Cl_2$, and most preferably, the catalyst loading is 0.03 eq. (based on the compound of Formula (II)).

Solvent: Various solvents may be used in the SMC reaction. Such solvents typically include but are not limited to solvents selected from the list consisting of ACN, THF, 2-Me-THF, DMF, NMP, toluene, $H_2O$, dioxane, acetone, MeOH, EtOH, iPrOH and nBuOH. Water is necessary, in at least trace amounts, for nearly all SMC reactions. Water hydrolyses boronates to the active boronic acid and likely plays a role in transmetallation. Water may arise from biphasic conditions or adventitious water in the solvent or base. In some embodiments of the invention, mixtures of solvents may be used, such as e.g. dioxane/$H_2O$ mixtures or DMF/$H_2O$ mixtures. In the most preferred embodiment of the invention, the solvent is ACN. The inventors found that the addition of a small amount of aqueous NaBr increased the catalyst activity and/or stability. Thus, in the most preferred embodiment, aqueous NaBr is added to the solvent, preferably to ACN as solvent. Various conditions for the SMC reaction were investigated. The most preferred conditions found were $K_2CO_3$ (2.0 eq), $Pd(dppf)Cl_2$ (0.03 eq), ACN (6 V) at 80-85° C.

Step a) or b). Hydrogenation

The hydrogenation may be performed in either step a) or step b). Thus, the hydrogenation may be performed in step a) on a compound of Formula (III) to obtain a racemic compound of formula (IVa) or (IVb). Alternatively, the hydrogenation may be performed in step b), on the compound of Formula (IIIa), to obtain a racemic compound of formula (IVb). Hydrogenation may, in addition to reducing the alkene in the compound of Formula (III), also effect cleavage of the protecting group (PG) when e.g. a benzyl carbamate, such as a Cbz, is used as PG. The inventors found that the hydrogenation was faster on the compound of Formula (IIIa) compared to the compound of Formula (III). Thus, in the most preferred embodiment, deprotection of Formula (III) is performed in step a) and hydrogenation is performed in step b).

Catalyst: A range of catalysts that can be employed for the hydrogenation reaction. Such catalysts include but are not limited to e.g. palladium/charcoal (Pd/C), $PtO_2$, palladium complexes, rhodium complexes (e.g. Wilkinson's catalyst), ruthenium complexes, or iridium complexes. In the most preferred embodiment, the catalyst is Pd/C. Typical catalyst loadings range from 1-20 wt % on process scale. In the most preferred embodiment, the catalyst loading is approximately 10 wt % Pd/C.

Solvent: A range of solvents may be used in the hydrogenation reaction. Such solvents include but are not limited to EtOAc, THF, 2-Me-THF, DMF, toluene, $H_2O$, dioxane, MeOH, EtOH, iPrOH, and nBuOH. In the most preferred embodiment, the solvent is EtOAc.

Pressure: The hydrogenation may be performed at various hydrogen pressures. Typically, the pressure is between 1-5 bars depending on the desired reaction time. In some embodiments, the hydrogenation is performed at atmospheric pressure without the need for pressurized reactors. In the most preferred embodiment, the reaction is performed at approximately 3.5 bars (50 psi) to shorten the reaction time.

Various conditions for the hydrogenation reaction were investigated. The most optimal conditions found were Pd/C (10 wt %), $H_2$ (50 psi), EtOAc (6 V) at 25-30° C.

Step a) or b). Deprotection

A deprotection of the protecting group (PG) may be performed in either step a) or step b). When the compound of Formula (IVa) is formed in step a), the deprotection of the amine protecting group (PG), preferably the carbamate PG, more preferably the Boc PG, is performed in step b) to obtain a compound of Formula (IVb). Alternatively, the deprotection may performed in step a) on the compound of Formula (III) to obtain a compound of formula (IIIa). Most preferably the deprotection is performed in step a) to obtain a compound of Formula (IIIa). Various deprotection conditions may be employed depending on the amine PG chosen. Suitable deprotection conditions for the different amine protecting groups can be found in e.g. Greene's Protective Groups in organic synthesis. Preferably, the protecting group is selected from a list consisting of a carbamate protecting group, an amide protecting group, a benzylamine protecting group, and a sulphonamide protecting group. In a more preferred embodiment, the protecting group is selected from a list consisting of 9-Fluorenylmethyl carbamate (Fmoc-$NR_2$), t-Butyl carbamate (Boc-$NR_2$), Benzyl carbamate (Cbz-$NR_2$), acetamide (Ac—$NR_2$), Trifluoroacetamide ($CF_3CO$—$NR_2$), Benzylamine (Bn-$NR_2$), 4-methoxybenzylamine (PMB-$NR_2$), Triphenylmethylamine (Tr-$NR_2$), and p-Toluenesulfonamide (Ts-$NR_2$). Preferably, the deprotection is performed by reacting the product of Formula (IVa), if formed in step a), in a solvent with an acid to remove the PG to obtain a compound of Formula (IVb). Preferably, the deprotection is performed by reacting the product of Formula (III), if formed in step a), in a solvent with an acid to remove the PG to obtain a compound of Formula (IIIa).

Deprotection reagents: Examples of deprotection reagents for amine protecting groups may be found in e.g. Greene's Protective Groups in organic synthesis, for amine protecting groups. Preferably, the deprotection reagent is an acid which may be employed for the deprotection of an amine protecting group, such as a t-Butyl carbamate (Boc-$NR_2$). Such acids include but are not limited to the list consisting of HCl, HBr, $H_2SO_4$, TFA, and TfOH. In the most preferred embodiment, the acid is HCl.

Solvent: Various solvents may be used in the deprotection reaction. Such solvents include but are not limited to e.g $H_2O$, ACN, EtOAc, THF, 2-Me-THF, DMF, toluene, dioxane, MeOH, EtOH, iPrOH and nBuOH. In some embodiments, the solvent may be a mixture of several solvents. In the embodiments wherein hydrogenation is performed prior to deprotection, the same solvent is preferably used in the deprotection (step b) as in the hydrogenation (step a) to avoid solvent switch, thereby simplifying the overall process. If the same solvent is used in steps a) and b), a simple filtration may be performed to remove the hydrogenation catalyst followed by deprotection. Thus, in these embodiments most preferably, EtOAc is used as solvent in both the hydrogenation and deprotection. Most, preferably the solvent is EtOAc and the deprotection reagent is HCl. In the embodiments wherein deprotection is performed prior to hydrogenation, MeTHF is preferably used in the deprotection step, preferably with HCl as deprotection reagent and preferably EtOAc is used in the hydrogenation.

When an acid is used in the deprotection, the protonated piperidine intermediate (i.e. the protonated compound of Formula (IVb)) or the protonated 1,2,3,6-tetrahydropyridine (i.e. the protonated compound of Formula (IIIa)) obtained under the acidic deprotection conditions may be liberated to obtain the compound of Formula (IVb) by conventional techniques known in the art, such as by partitioning the compound between an organic phase (e.g. EtOAc) and an aqueous basic phase (e.g. aqueous 20% $Na_2CO_3$ or an aqueous saturated $NaHCO_3$).

Step c). Chiral Resolution

Step c) is a chiral resolution to obtain the (S)-enantiomers in high enantiomeric excess (% ee). In an embodiment of the invention, the enantiomeric excess is at least 60% ee, such as at least 70% ee, such as at least 75% ee, such as at least 80% ee, such as at least 85% ee, preferably at least 90% ee, more preferably at least 95% ee. Most preferably, the enantiomeric excess is at least 75% such that the final crystalline salts can be obtained in high enantiomeric excess, preferably without the need for recrystallization. In some embodiments, the enantiomeric excess may be further improved by performing a crystallization/recrystallization in a suitable solvent. The chiral resolution may be performed by derivatization of the racemic compound of Formula (IVb) with an optically pure acid forming pairs of diastereomers which can be separated by conventional techniques such as crystallization. The two diastereomeric salts formed possess different solubility which allows for a selective precipitation of one diastereomeric salt over the other. Alternatively, the enantiomers may be separated by e.g. chiral continuous chromatographic separation.

Chiral acids: A large number of chiral acids are commercially available, inexpensive, and thereby suitable for use in a process chemistry route that is performed on large scale (e.g. kg scale). Such chiral acids include e.g. chiral amino acids, (1S)-(−)-Camphanic acid, L-(+)-Mandelic acid, D-(−)-Tartaric acid or L-(+)-Tartaric acid and derivatives thereof.

In an embodiment of the invention, the chiral resolution is performed by reacting the compound of Formula (VIb) with an chiral acid selected from (−)—O,O'-Di-p-toluoyl-L-tartaric acid or (−)-Di-p-anisoyl-L-tartaric acid, preferably (−)-Di-p-anisoyl-L-tartaric acid, to form pairs of diastereomers, wherein the diastereomeric salt between (S)-3-(2,5-dimethoxy-4-(trifluoromethyl)phenyl)piperidine or (S)-3-(2-methoxy-5-(methylthio)-4-(trifluoromethyl) phenyl) piperidine and the chiral acid has a lower solubility than the diastereomeric salt formed between (R)-3-(2,5-dimethoxy-4-(trifluoromethyl)phenyl)piperidine or (R)-3-(2-methoxy-5-(methylthio)-4-(trifluoromethyl) phenyl) piperidine and the chiral acid. The precipitated diastereomeric salt may be separated by conventional filtration.

Solvents: Various solvents can be used for the chiral resolution. Such solvents include but are not limited to e.g. 2-Me-THF, THF, MeOH, EtOH, ACN, IPA, MTBE, DCM or Acetone. In some embodiments, water may be added as a co-solvent.

Various conditions were tested for the selective precipitation of the compound of Formula (V). The solvents ACN, IPA, THF, and MTBE were tested with the chiral acids (−)-Di-p-anisoyl-L-tartarid acid, (+)-Dipivaloyl-D-tartaric Acid, (−)—O,O'-Di-p-toluoyl-L-tartaric acid, (1S)-(−)-Camphanic acid, (S)-2-Acetoxy-2-phenylacetic acid, L-Glutamic acid, N-Acetyl-L-Isoleucine, D-(−)-Tartaric acid. The solvents ACN, IPA and THF were used with water as co-solvent (15 vol. solvent: 3 vol. $H_2O$). MTBE was used with water as co-solvent (20 vol. MTBE: 5 vol. $H_2O$). The most optimal conditions were found to be (−)-Di-p-anisoyl-L-tartaric acid (1 eq.) in a mixture of THF/$H_2O$. Table 1 shows some representative examples of the % ee obtained.

TABLE 1

Optimization results of chiral resolution

| Entry | Chiral acid | Solvent | % ee (Formula (S)-(IVb)) | % ee of ML |
|---|---|---|---|---|
| 1 | (—)-Di-p-anisoyl-L-tartaric acid | THF/$H_2O$ | 95.2% | −76.6% |
| 2 | (—)-O,O'-Di-p-toluoyl-L-tartaric acid | THF/$H_2O$ | 89.6% | −68.1% |
| 3 | (—)-Di-p-anisoyl-L-tartaric acid | IPA/$H_2O$ | 86.3% | −92.3% |
| 4 | (—)-O,O'-Di-p-toluoyl-L-tartaric acid | IPA/$H_2O$ | 87.6% | −82.7% |

TABLE 1-continued

| Optimization results of chiral resolution | | | | |
|---|---|---|---|---|
| Entry | Chiral acid | Solvent | % ee (Formula (S)-(IVb)) | % ee of ML |
| 5 | (—)-O,O'-Di-p-toluoyl-L-tartaric acid | Acetone/$H_2O$ | 75.0% | −86.4% |
| 6 | Dibenzoyl-L-Tartaric acid | ACN/$H_2O$ | 92.9% | −16.6% |

The solubility of the (−)-Di-p-anisoyl-L-tartaric acid salt of (S)-3-(2,5-dimethoxy-4-(trifluoromethyl) phenyl)piperidine (1:1) and the (−)-Di-p-anisoyl-L-tartaric acid salt of (R)-3-(2,5-dimethoxy-4-(trifluoromethyl)phenyl)piperidine (1:1) were examined as shown in the Table 1a. The data suggests that DCM may be an even better solvent than THF/1$H_2O$ providing even higher enantiomeric excess. Thus, in another highly preferred embodiment, DCM is used in step c).

TABLE 1a

| Solubility of diastereomeric salts | | |
|---|---|---|
| | Solubility @ 20-30° C. (mg/ml) | |
| Solvent | 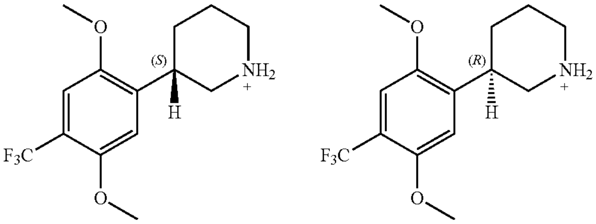 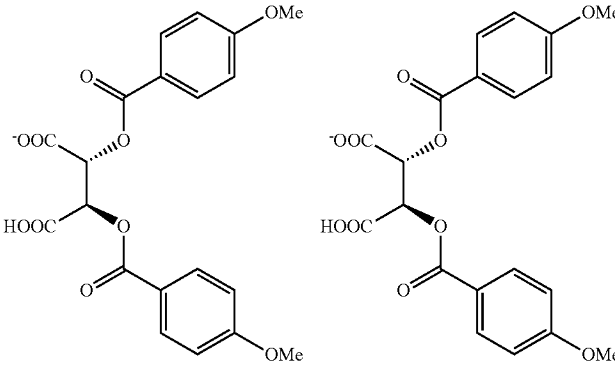 | |
| Water | <5 | <5 |
| MeOH | 30 | 40 |
| EtOH | 12 | 25 |
| IPA | <10 | <10 |
| THF | 50 | 45 |
| MTBE | <10 | <10 |
| 2-MeTHF | 50 | 20 |
| Acetone | <10 | <10 |
| MEK | <10 | <10 |
| IPAC | <10 | <10 |
| EtOAc | <10 | <10 |
| DCM | <10 | >400 |
| ACN | 12 | 20 |
| Toluene | <10 | <10 |
| Heptane | <10 | <10 |

The precipitated enantioenriched salt of Formula (V) may be liberated to the compound of Formula (S)-(IVb) by conventional techniques known in the art, such as by partitioning the compound between an organic phase (e.g. EtOAc) and an aqueous basic phase (e.g. aqueous 20% $Na_2CO_3$ or an aqueous saturated $NaHCO_3$). The majority of the compound of Formula (S)-(IVb) will remain in the organic phase whereas the salts remain in the aqueous phase.

Step d). Preparation of Final Salts

Step d) is the precipitation of the compound of Formula (S)-(IVb) with succinic acid, L-tartaric acid, or HCl to obtain a crystalline compound of Formula (VI).

As shown in the experimental section below, the inventors found that HCl salt (polymorph A), the L-tartrate salt (polymorph B, 1:1 salt of acid:base), and the succinate salt (polymorph A, 1:1 of acid:base) of (S)-3-(2,5-dimethoxy-4-(trifluoromethyl)phenyl)piperidine possessed overall good properties in terms of e.g. crystallinity, thermal properties, stability, solubility, and hygroscopicity. In particular, the HCl salt (polymorph A) and the succinate salt (polymorph A, 1:1 salt) possessed the overall superior properties.

Succinic acid and L-tartaric acid are both diprotic acids. Thus, these acids may form salts with the compound of Formula (S)-(IVb) in a 1:1 ratio (acid:base) or in a 0.5:1 ratio (acid:base). As shown in examples 3 and 4, the inventors surprisingly found that the superior properties of the succinic acid salt and the L-tartaric acid salt were obtained when the salts were formed in a 1:1 ratio (acid:base). These salts resulted in a single stable polymorph as anhydrates in the screened solvents, whereas the hemi L-tartrate salt and the hemi succinate salt (0.5:1 ratio acid:base) resulted in hydrates that underwent dehydration, were less crystalline and/or hygroscopic. Thus, in a highly preferred embodiment, 1 eq. of the compound of Formula (S)-(IVb) is precipitated with 1 eq. succinic acid or 1 eq. of HCl to form the salt in a 1:1 ratio (i.e. a compound of Formula (VI)). In the most preferred embodiment of the invention, 1 eq. of the compound of Formula (S)-(IVb) is precipitated with 1 eq. succinic acid to form the salt in a 1:1 ratio (i.e. a compound of Formula (VI)). Any of the solvents ACN, EtOH or Acetone were found to be suitable for the crystallization as all the solvents provided the same stable polymorph (polymorph A). Example 5 (Table 10) suggests that a wide range of other solvents may also be used as the same polymorph was obtained under solvent mediated equilibration. In the most preferred embodiment, the solvent is EtOH. The compound of Formula (VI) may be isolated by simple filtration.

Aspect II

The inventors further found that the process route could be performed without the need for chiral resolution (i.e. step c). Thus, in a second aspect, the desired (S)-enantiomer may be obtained by enantioselective synthesis using an asymmetric hydrogenation in order to avoid the chiral resolution. Thus, in a second aspect, the method comprises the inclusion of a chiral catalyst in step a) or b) of aspect I in order to perform an enantioselective reduction (i.e. hydrogenation) of the alkene in compound of Formula (III) or (IIIa). The benefit of asymmetric hydrogenation is an overall shorter API-route that makes chiral resolution (i.e. step c) in aspect I) with chiral derivatising agents redundant.

Thus, in a second aspect, the present invention relates to a method for the manufacture of a compound of Formula (VI) comprising the steps of:

a) reacting the compound of Formula (III), wherein PG is an amine protecting group, (III)

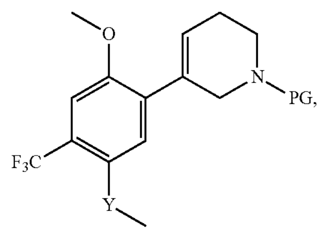

in a solvent with hydrogen gas ($H_2$) in the presence of a transition metal catalyst, and a chiral ligand, to obtain a compound of Formula (S)-(IVa) or (S)-(IVb), having an enantiomeric excess (% ee) of at least 70%, (S)-(IVa)

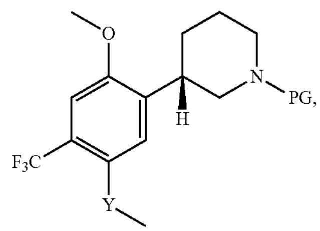

(S)-(IVb)

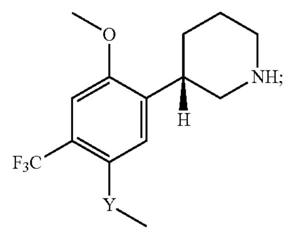

or alternatively, reacting the compound of Formula (III) in a solvent, with a deprotection reagent to obtain a compound of Formula (IIIa), (IIIa)

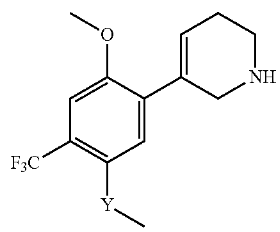

b) reacting the compound of Formula (S)-(IVa), if formed in step a), in a solvent with a deprotection reagent to obtain a compound of Formula (S)-(IVb) having an enantiomeric excess (% ee) of at least 70%, or alternatively, reacting the compound of Formula (IIIa), if formed in step a), in a solvent with hydrogen gas ($H_2$) in the presence of a transition metal catalyst, and a chiral ligand, to obtain a compound of Formula (S)-(IVb), having an enantiomeric excess (% ee) of at least 70%, (S)-(IVb)

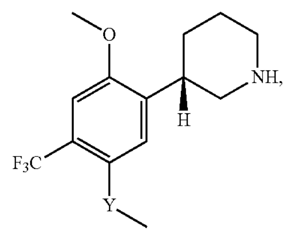

c) reacting the compound of Formula (S)-(IVb) in a solvent with succinic acid, L-tartaric acid, or HCl to obtain a crystalline compound of Formula (VI), (VI)

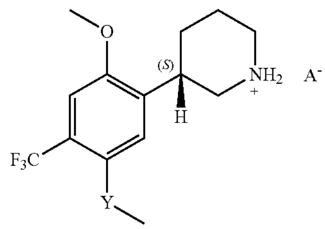

wherein $A^-$ is selected as 3-carboxypropanoate, (2R,3R)-3-carboxy-2,3-dihydroxypropanoate or chloride (C).

Step a) or b). Asymmetric Hydrogenation

In an embodiment of the second aspect, the hydrogenation is performed on the compound of Formula (IIIa) (i.e. step b) in the presence of a chiral catalyst to provide a compound of Formula (S)-(IVb) (i.e. the desired (S)-enantiomer) in an enantiomeric excess (ee). In a preferred embodiment of the second aspect, the hydrogenation is performed on the compound of Formula (III) (i.e. step a) in the presence of a chiral catalyst to provide a compound of Formula (S)-(IVa) or (S)-(IVb) (i.e. the desired (S)-enantiomer) in an enantiomeric excess (ee). Most preferably, the asymmetric hydrogenation is performed on the compound of Formula (III) (i.e. step a), as the protecting group improved enantiomeric excess compared to the deprotected compound of Formula (IIIa). Preferably, the enantiomeric excess in the asymmetric hydrogenation is at least 60% ee, such as at least 70% ee, such as at least 75% ee, preferably at least 80% ee, such as at least 85% ee, more preferably at least 90% ee, such as at least 92% ee, even more preferably at least 94% ee. such as at least 96% ee, yet more preferably at least 97% ee, such as at least 98% ee, most preferably the enantiomeric excess is >99% ee. The enantiomeric excess obtained may be verified with methods commonly used in the art, such as chiral HPLC. Most preferably, the asymmetric hydrogenation provides the (S)-enantiomer in a such high enantiomeric excess that no chiral resolution is needed. In the case where only a moderate enantiomeric excess is achieved in the asymmetric hydrogenation (e.g. at least 70% ee), the enantiomeric excess can be further increased in the final precipitation step to obtain a compound of Formula (VI) in high enantiomeric excess (e.g. >95% ee). This is because the (S)-enantiomer is present in a higher excess than the (R)-enantiomer and due to the fact that enantiomers possess the same solubility (i.e. the (S)-enantiomer precipitates out first). In the event that final precipitation to form a compound of Formula (VI) does not provide a desired enantiomeric excess, the compound of Formula (VI) may be recrystallized one or more times until the desired enantiomeric excess is reached, such as at least 97% ee, preferably at least 98% ee, most preferably at least 99% ee. The conditions described for the hydrogenation (i.e. step a) or b) in aspect I) apply equally for the asymmetric hydrogenation but require the presence of a chiral ligand.

Chiral Ligand

A range of chiral ligands can be employed for asymmetric hydrogenation. Such chiral ligands include e.g. phosphine ligands based on BINAP, SYNPHOS, DIOP, DuPhos, Josiphos, BDPP, BIBOP, Mandyphos or phosphoramidites, such as e.g. MONOPHOS. Most preferably the chiral ligand is (R,R)-i-Pr-DuPhos. The asymmetric reduction circumvents the need for chiral resolution with a chiral acid. Thus, step d) (i.e. chiral resolution with a chiral acid) is not necessary when asymmetric hydrogenation is used. However, the remaining steps (i.e. step a) SMC coupling, step b or c) deprotection and step d) preparation of final salts) may be performed in the same way as described herein. Thus, the embodiments described herein for the remaining steps apply mutatis mutandis to the embodiments using asymmetric hydrogenation. For the asymmetric hydrogenation, the best conditions were found to be $Rh(NBD)BF_4$ as catalyst, (R,R)-i-Pr-DuPhos as chiral ligand and EtOH as solvent, preferably with premixing of catalyst and chiral ligand. Table 2 shows some representative examples of the % ee obtained.

TABLE 2

Results of asymmetric hydrogenation

| Entry | Catalyst (2 mol %) | Chiral ligand | Solvent | % ee (Formula (S)-(IVb)) | Catalyst and Chiral ligand premixed (t) |
|---|---|---|---|---|---|
| 1 | $Rh(NBD)BF_4$ | 2 mol % (R,R)-i-Pr-DuPhos | EtOH | 73.8 | — |
| 2 | $Rh(NBD)BF_4$ | 2 mol % (R,R)-i-Pr-DuPhos | EtOH | 86.4 | 2 min |
| 3 | $Rh(NBD)BF_4$ | 2.2 mol % (R,R)-i-Pr-DuPhos | EtOH | 83.3 | 2 min |
| 4 | $Rh(NBD)BF_4$ | 4 mol % (R,R)-i-Pr-DuPhos | EtOH | 85.0 | 1 hour |
| 5 | $Rh(NBD)BF_4$ | 2.2 mol % (R,R)-i-Pr-DuPhos | EtOH | 79.2 | 1 hour |

Step a) or b). Deprotection

The deprotection in step a) or b) in aspect II is performed in the same way as the deprotection in step a) or b) in aspect I. Thus, the description and the embodiments of the deprotection of aspect I apply equally to aspect II.

Step c). Preparation of Final Salts

Step c) of aspect II is the preparation of the final crystalline salts and the specific polymorphs thereof and is performed in the same way as the preparation of final salts in aspect I. Thus, the description and embodiments of the preparation of the final salts in aspect I apply equally to aspect II.

In an embodiment of aspect II, the method further comprises the step a1), prior to step a), of:

a1) reacting a compound of Formula (I) with a compound of Formula (II) in a solvent, (I)

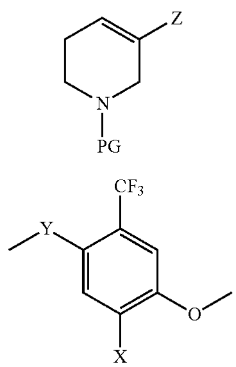

(II)

wherein Z is selected from the group consisting of a boronic acid, a trifluoroborate salt and boronic esters, PG is an amine protecting group, Y is selected from S or O, X is selected from Cl, Br, I or OTf, in the presence of a base and a transition metal catalyst to obtain a compound of Formula (III)

(III)

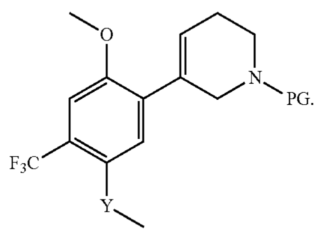

Step a1). Suzuki-Miyaura Cross-Coupling (SMC)

Step a1) in aspect II is identical to step at) in aspect I. Thus, the description and embodiments described for the SMC reaction in aspect I apply equally to aspect II.

Thus, in a highly preferred embodiment of aspect II, the present invention relates to a method for the manufacture of a compound of Formula (VI) comprising the steps of:

a1) reacting a compound of Formula (I) with a compound of Formula (II) in a solvent, (I)

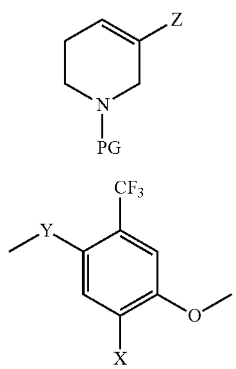

(II)

wherein Z is selected from the group consisting of a boronic acid, a trifluoroborate salt and boronic esters, PG is an amine protecting group, Y is selected from S or O, X is selected from Cl, Br, I or OTf, in the presence of a base and a transition metal catalyst to obtain a compound of Formula (III)

(III)

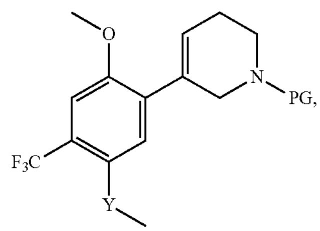

a) reacting the compound of Formula (III) with hydrogen gas ($H_2$) in the presence of a transition metal catalyst and a chiral ligand to obtain a compound of Formula (S)-(IVa) or (S)-(IVb) having an enantiomeric excess (% ee) of at least 70%, (S)-(IVa)

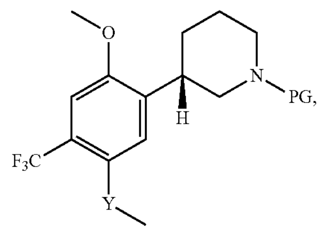

(S)-(IVb)

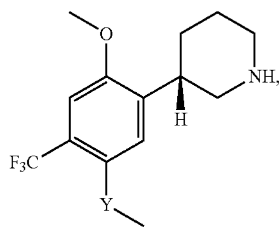

or alternatively, reacting the compound of Formula (III) in a solvent with a deprotection reagent to obtain a compound of Formula (IIIa)

(IIIa)

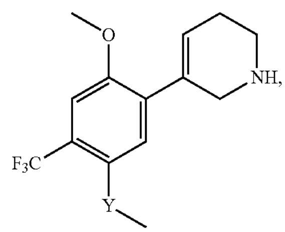

b) reacting the compound of Formula (S)-(IVa), if formed in step a), in a solvent with a deprotection reagent to obtain a compound of Formula (S)-(IVb) having an enantiomeric excess (% ee) of at least 70%, or alternatively, reacting the compound of Formula (IIIa), if formed in step a), in a solvent with hydrogen gas ($H_2$) in the presence of a transition metal catalyst and a chiral ligand, to obtain a compound of Formula (S)-(IVb), having an enantiomeric excess (% ee) of at least 70%, (S)-(IVb)

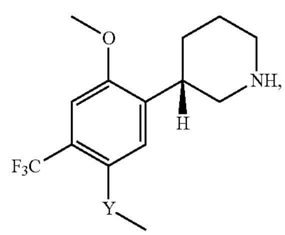

c) reacting the compound of Formula (S)-(IVb) in a solvent with succinic acid, L-tartaric acid, or HCl to obtain a crystalline compound of Formula (VI), (VI)

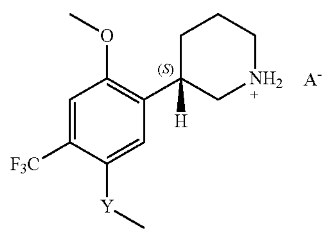

wherein $A^-$ is selected as 3-carboxypropanoate, (2R,3R)-3-carboxy-2,3-dihydroxypropanoate or chloride ($Cl^-$).

Most preferably the asymmetric hydrogenation is performed on the compound of Formula (III) (i.e. the protected intermediate).

Preparation of compound of Formula (II)

In order to obtain a compound of Formula (II), for use in step a), in large quantities at lower costs, the inventors developed a two-step scalable process chemistry route to 1-bromo-2,5-dimethoxy-4-(trifluoromethyl)benzene starting from the less expensive precursor 4-methoxy-3-(trifluoromethyl)phenol (Formula IIa).

Thus, in some embodiments of the invention, the process according to the first and second aspects comprises further steps, prior to step a1), of reacting a compound of Formula (IIa) in a solvent, (IIa)

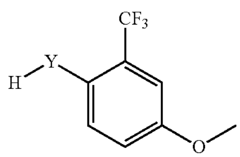

wherein, Y is O or S, with a halogenating agent in the presence of an acid to obtain a compound of Formula (IIb)

(IIb)

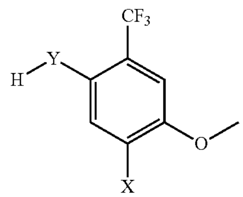

wherein X is selected from Cl, Br or I, and reacting the compound of Formula (IIb) in a solvent with a methylating agent in the presence of a base to obtain a compound of Formula (II)

(II)

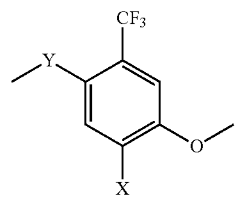

Halogenation:

Halogenating agents Various halogenating agents are suitable for the installation of a chlorine, bromine, or iodine atom in the compound of Formula (IIa). Suitable chlorinating agents include but are not limited to the list consisting of cyanuric chloride, N-Chlorosuccimide, N-Chlorophthalimide, 1,3-Dichloro-5,5-dimethylhydantoin, sodium dichloroisocyanurate, trichloroisocyanuric acid, N-Chlorosaccharin, Chloramine B Hydrate, o-Chloramine T Dihydrate, Chloramine T Trihydrate, Dichloramine B, Dichloramine T, Benzyltrimethylammonium Tetrachloroiodate. Suitable brominating reagents may include but are not limited to $Br_2$, $CBr_4$, Tetrabutylammonium Tribromide, Trimethylphenylammonium Tribromide, Benzyltrimethylammonium Tribromide, Pyridinium Bromide Perbromide, 4-Dimethylaminopyridinium Bromide Perbromide, 1-Butyl-3-methylimidazolium Tribromid, 1,8-Diazabicyclo[5.4.0]-7-undecene Hydrogen Tribromide, N-Bromosuccinimide, N-Bromophthalimide, N-Bromosaccharin, N-Bromoacetamide, 2-Bromo-2-cyano-N,N-dimethyl-acetamide, 1,3-Dibromo5,5-dimethylhydantoin, Dibromoisocyanuric Acid, Monosodium Bromoisocyanurate Hydrate, $PBr_3$, Bromodimethylsulfonium Bromide, 5,5-Dibromomeldrum's Acid, 2,4,4,6-Tetrabromo2,5-cyclohexadienone, Bis(2,4,6-trimethylpyridine)-bromonium Hexafluoro-phosphate. Various iodinating agents include but are not limited to the list consisting of $I_2$, HI, $CI_4$, N-Iodosuccinimide, N-Iodosaccharin, 1,3-Diiodo-5,5-dimethylhydantoin, Pyridine Iodine Monochloride, Tetramethylammonium Dichloroiodate, Benzyltrimethylammonium Dichloroiodate and Bis(pyridine)iodonium Tetrafluoroborate. In a preferred embodiment of the invention, the halogenating reagent is a brominating reagent, most preferably Pyridinium Bromide Perbromide ($PyHBr_3$).

Acids Several acids are suitable for use in the halogenation reaction of compound of Formula (IIa). Such acids include both Lewis acids, and Brønsted acids. Suitable acids may include but are not limited to acids selected from the list consisting of pTsOH, MsOH, HCl, and TfOH.

So/vents. Several solvents are suitable for the halogenation reaction of compound of Formula (IIa). Such solvents include e.g. MTBE, THF, ACN, DMF, 2-MeTHF, EtOAc, EtOH, toluene, acetone, or MeOH.

The inventors investigated various conditions for the halogenation. The most preferred conditions found were Pyridinium Bromide Perbromide ($PyHBr_3$, 1 eq.), TfOH (2.0 eq), DCM (6 V) at 0-10° C.

Alkylation:

Alkylating reagents: Various methylating agents are suitable for the methylation of the compound of Formula (IIb). Such reagents include but are not limited to methylating agents selected from the list consisting of MeI, Methyl fluorosulfonate, Methyl methanesulfonate, Dimethyl carbonate and Dimethyl sulfate. In the most preferred embodiment of the invention, the methylating agent is MeI.

Bases: Various bases may be used in the methylation of the compound of Formula (IIb). Such bases include but are not limited to e.g. alkali carbonate bases such as $Na_2CO_3$, $K_2CO_3$, $Cs_2CO_3$, alkaline earth metal bases such as $MgCO_3$ or $CaCO_3$ or hydride bases such as NaH.

The inventors investigated various conditions for the alkylation. The most optimal conditions found were MeI (1.1 eq.), $K_2CO_3$ (1.5 eq.), Acetone (6 V) at 50-55° C.

Aspect III

As shown in examples 3 and 4, the inventors found that the HCl salt (polymorph A), the succinate salt (i.e. polymorph A, 1:1 ratio of acid:base), and the L-tartrate salt (i.e. polymorph B, 1:1 ratio of acid:base) possessed good overall properties compared to the other salts in the salt screen. In particular, these salts were anhydrates that showed high crystallinity, high melting points, good thermal properties, little or no hygroscopicity, good solubility, good bulk stability, and formed a single stable polymorph in the solvents screened. On the contrary, the hemi-succinate and hemi-L-tartrate (i.e. 1:0.5 ratio of acid:base) resulted in hydrates that underwent dehydration as determined by Differential Scanning Calorimetric (DSC), were more hygroscopic, and/or formed different polymorphs from the solvents tested. Furthermore, the succinate salt (i.e. polymorph A, 1:1 ratio of acid:base) and the HCl salt (polymorph A) showed considerably higher solubility than the L-tartrate salt (i.e. polymorph B, 1:1 ratio of acid:base) in water. Therefore, the succinate salt (i.e. polymorph A, 1:1 ratio of acid:base, FIG. 1) and the HCl salt (polymorph A, FIG. 2), most preferably the succinate salt (1:1 ratio), were/was identified as the best salt(s) for developing an API for drug manufacturing.

Thus, in a third aspect, the invention relates to a crystalline compound of Formula (VI)

(VI)

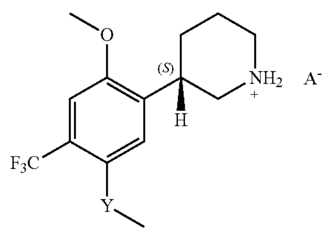

wherein Y is selected from O or S;

$A^-$ is selected as 3-carboxypropanoate, (2R,3R)-3-carboxy-2,3-dihydroxypropanoate or chloride ($Cl^-$).

In a preferred embodiment, Y is selected as O. In another preferred embodiment, Y is selected as S. In yet a preferred embodiment, Y is selected from O or S; $A^-$ is selected as 3-carboxypropanoate or $Cl^-$, more preferably as 3-carboxypropanoate. In another preferred embodiment, Y is selected as S; $A^-$ is selected 3-carboxypropanoate or $Cl^-$, most preferably 3-carboxypropanoate. In a more preferred embodiment, Y is selected as 0; $A^-$ is selected 3-carboxypropanoate or $Cl^-$, most preferably 3-carboxypropanoate.

Amorphous and crystalline compounds can easily be distinguished using e.g. microscopy. The best way to differentiate between amorphous and crystalline materials is to measure XRD patterns. Crystalline material always exhibits sharp diffraction peaks while amorphous material does not. Likewise, different polymorphs of a crystalline material may be identified due to different XRD patterns. Moreover, the crystallinity of the materials can be confirmed from selected area electron diffraction (SAED) patterns using transmission electron microscope (TEM micrograph).

Figure 3:
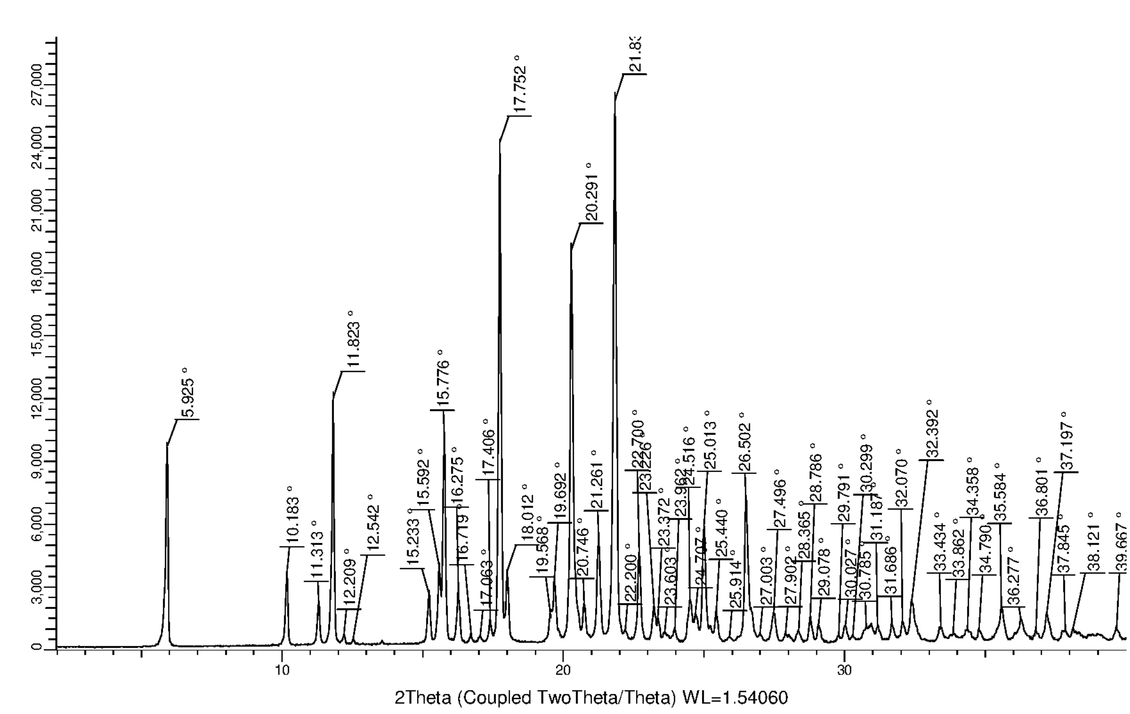
FIG. 3 shows the XPRD spectrum of the polymorph B of the compound of Formula (VI), wherein Y is O and wherein $A^-$ is (2R,3R)-3-carboxy-2,3-dihydroxypropanoate (i.e. 1:1 salt formed between (S)-3-(2,5-dimethoxy-4-(trifluoromethyl)phenyl)piperidine and L-tartaric acid). Embodiments of the invention will be described in more detail in the following with regard to the accompanying figures.

In an embodiment, Y is selected as 0; $A^-$ is selected as (2R,3R)-3-carboxy-2,3-dihydroxypropanoate and the salt is the polymorph with the XRPD spectrum having 28 peaks 5.925°, 10.183°, 11.313°, 11.823°, 12.209°, 12.542°, 15.233°, 15.592°, 15.776°, 16.275°, 16.719°, 17.063°, 17.406°, 17.752°, 18.012°, 19.568°, 19.692°, 20.291°, 20.746°, 21.261°, 21.839°, 22.200°, 22.700°, 23.226°, 23.372°, 23.603°, 23.962°, 24.516°, 24.707°, 25.013°, 25.440°, 25.914°, 26.502°, 27.003°, 27.496°, 27.902°, 28.365°, 28.786°, 29.078°, 29.791°, 30.027°, 30.299°, 30.785°, 31.187°, 31.686°, 32.070°, 32.392°, 33.434°, 33.862°, 34.358°, 34.790°, 35.584°, 36.277°, 36.801°, 37.197°, 38.121° and 39.667° as shown in FIG. 3.

Figure 2:
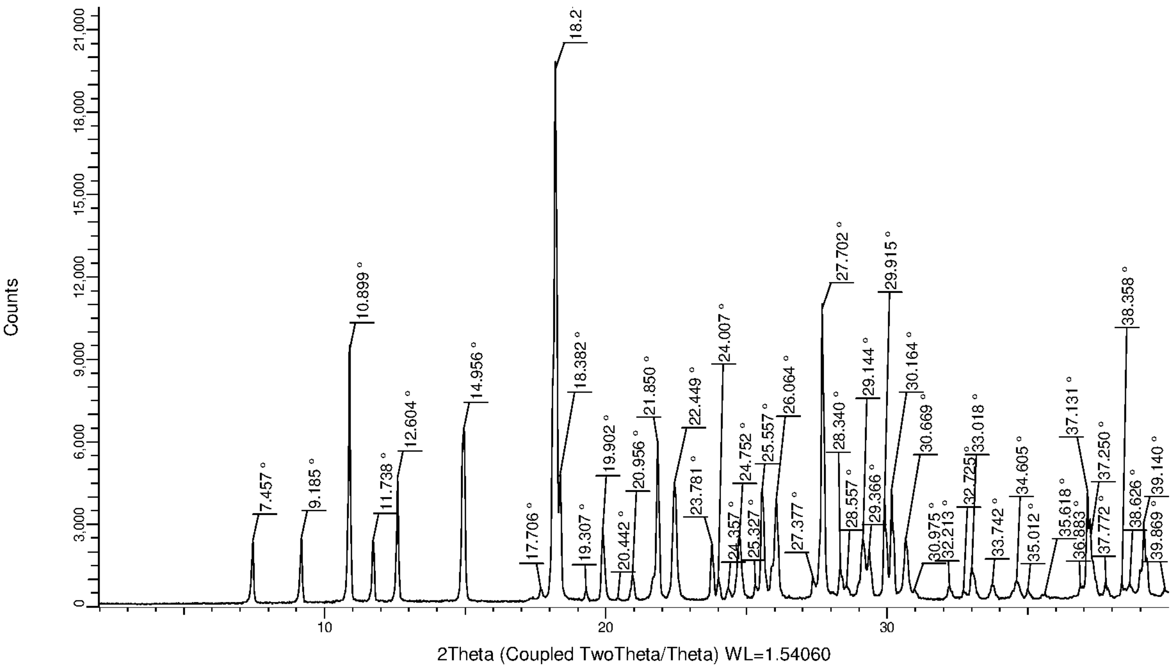
FIG. 2 shows the XPRD spectrum of the polymorph A of the compound of Formula (VI), wherein Y is O and wherein $A^-$ is chloride ($Cl^-$) (i.e. 1:1 salt formed between (S)-3-(2,5-dimethoxy-4-(trifluoromethyl)phenyl)piperidine and HCl).

In a highly preferred embodiment, Y is selected as 0; $A^-$ is selected as chloride ($Cl^-$) and the salt is the polymorph with the XRPD spectrum having 28 peaks 7.457°, 9.185°, 10.899°, 11.738°, 12.604°, 14.956°, 17.706°, 18.215°, 18.382°, 19.307°, 19.902°, 20.442°, 20.956°, 21.850°, 22.449°, 23.781°, 24.007°, 24.357°, 24.752°, 25.327°, 25.557°. 26.064°, 27.377°, 27.702°, 28.340°, 28.557°, 29.144°, 29.366°, 29.915°, 30.164°, 30.669°, 30.975°, 32.213°, 32.725°, 33.018°, 33.742°, 34.605°, 35.012°, 35.618°, 36.883°, 37.131°, 37.250°, 37.772°, 38.358°, 38.626°, 39.140°, 39.869° as shown in FIG. 2.

In the most preferred embodiment, Y is selected as 0; $A^-$ is selected as 3-carboxypropanoate and the salt is the polymorph with the XRPD spectrum having 28 peaks 4.0770, 8.108°, 11.991°, 12.156°, 13.893°, 15.876°, 16.218°, 16.412, 16.596°, 17.849°, 19.507°, 19.786°, 20.031°, 20.297°, 21.122°, 22.011°, 22.635°, 23.000°, 23.268°, 24.065°, 24.408°, 25.414°, 25.758°, 26.947°, 27.751°, 28.032°, 28.314°, 29.966°, 30.358°, 30.562°, 30.770°, 31.378°, 32.306°, 32.868°, 33.505°, 34.710°, 35.206°, 36.418°, 36.714°, 37.306°, 38.147°, 38.322°, 38.745° as shown in FIG. 1.

In the present context, it should be understood that the XRPD spectra (i.e. the 2θ peaks given) are obtained using the X-ray Powder Diffractometer and method disclosed in general instrumental methods.

Aspect IV

In a fourth aspect the invention relates to intermediates of Formula (III) or (IIIa), (III)

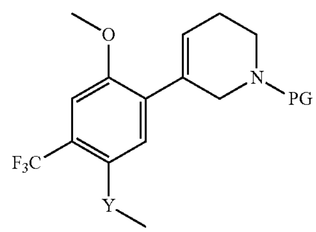

-continued (IIIa)

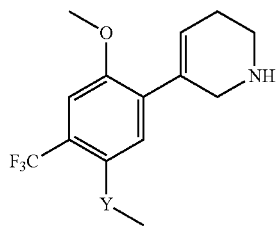

wherein Y is selected from O or S,

PG is an amine protecting group.

Common amine protecting groups include carbamates such as 9-Fluorenylmethyl carbamate (Fmoc-$NR_2$), t-Butyl carbamate (Boc-$NR_2$) and Benzyl carbamate (Cbz-$NR_2$), amides such as acetamide (Ac—$NR_2$) and Trifluoroacetamide ($CF_3CO$—$NR_2$); Benzylamines such as Benzylamine (Bn-$NR_2$) or 4-methoxybenzylamine (PMB-$NR_2$); Triphenylmethylamine (Tr-$NR_2$); Sulfonamides such as p-Toluenesulfonamide (Ts-$NR_2$). Thus, in an embodiment of the invention, the protecting group PG is selected from a list consisting of a carbamate, an amide, a benzylamine, or a sulphonamide. In a preferred embodiment, the PG is selected from a list consisting of 9-Fluorenylmethyl carbamate (Fmoc-$NR_2$), t-Butyl carbamate (Boc-$NR_2$), Benzyl carbamate (Cbz-$NR_2$), acetamide (Ac—$NR_2$), Trifluoroacetamide ($CF_3CO$—$NR_2$), Benzylamine (Bn-$NR_2$), 4-methoxybenzylamine (PMB-$NR_2$), Triphenylmethylamine (Tr-$NR_2$), and p-Toluenesulfonamide (Ts-$NR_2$).

More preferably, the protecting group (PG) is a carbamate protecting group such as Boc (t-Butyloxycarbonyl) or CBz (carboxybenzyl). A Boc protecting group has the benefit that it may be removed under acidic conditions with concomitant salt formation. This may in certain embodiments allow for a one-pot deprotection, precipitation and isolation of the product. E.g. a CBz protecting group has the benefit that the cleavage of the protecting group and the reduction of the alkene (i.e. double bond in the piperidine) in the compound of Formula (III) may be performed in a single step such that a separate deprotection step (i.e. step c) is not needed. The skilled person is well aware of suitable protecting groups for amines, the protection conditions used to install them, as well as their deprotection (i.e. cleavage) conditions, which can be found in e.g. Greene's Protective Groups in organic synthesis. Thus, the protecting group may be changed to other suitable amine protecting groups not explicitly mentioned herein.

In a preferred embodiment, PG is a carbamate protecting group. In a highly preferred embodiment, the carbamate is selected from Boc or Cbz. In the most preferred embodiment, the carbamate protecting group is a Boc group. Most preferably, Y is O.

Aspect V

In a fifth aspect, the invention relates to the use of intermediate of Formula (III)

(III)

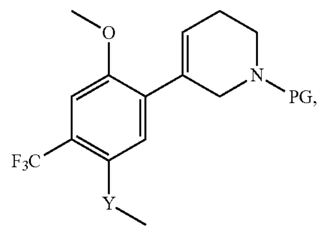

wherein Y is selected from O or S,

PG is an amine protecting group, for the manufacture of compounds of Formula (IVa), (IVb), (IIIa), (S)-(IVa), (S)-(IVb), (V), or (VI);

or the use of intermediate of Formula (IIIa)

(IIIa)

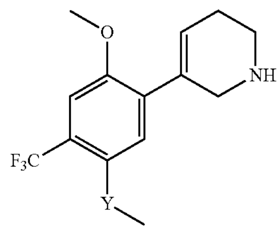

wherein Y is selected from 0 or S, for the manufacture of compounds of Formula (IVb), (S)-(IVb), (V), or (VI).

Suitable amine PG can be found in e.g. Greene's Protective Groups in organic synthesis or in the list mentioned under aspect IV, which equally apply to aspect V. In a preferred embodiment, PG is a carbamate protecting group. In a highly preferred embodiment, the carbamate protecting group is selected from Boc or Cbz. In the most preferred embodiment, the carbamate protecting group is a Boc group. Most preferably, Y is O.

EXPERIMENTAL

General Instrumental Methods

| X-ray Powder Diffractometer (XRPD) | |
|---|---|
| Instrument | Bruker D8 Advance<br>XRPD method 1 (About 10 min) |
| Detector | LYNXEYE_XE_T(1D mode) |
| Open angle | 2.94° |
| Scan mode | Continuous PSD fast |
| Radiation | Cu/K-Alpha1 (λ = 1.5418Å) |
| X-ray generator power | 40 kV, 40 mA |
| Step size | 0.02° |
| Time per step | 0.3 second per step |
| Scan range | 2° to 40° |
| Primary beam path slits | Twin_Primary motorized slit 10.0 mm by sample length; SollerMount axial soller 2.5° |

-continued

| | |
|---|---|
| Secondary beam path slits | Detector OpticsMount soller slit 2.5°; Twin_Secondary motorized slit 5.2 mm |
| Sample rotation speed | 15 rpm |
| XRPD method 2 (About 4 min, for stability samples, solubility samples and hygroscopicity samples) | |
| Detector | LYNXEYE_XE_T(1D mode) |
| Open angle | 2.94° |
| Scan mode | Continuous PSD fast |
| Radiation | Cu/K-Alpha1 (λ = 1.5418Å) |
| X-ray generator power | 40 kV, 40 mA |
| Step size | 0.02° |
| Time per step | 0.12 second per step |
| Scan range | 2° to 40° |
| Primary beam path slits | Twin_Primary motorized slit 10.0 mm by sample length; SollerMount axial soller 2.5° |
| Secondary beam path slits | Detector OpticsMount soller slit 2.5°; Twin_Secondary motorized slit 5.2 mm |
| Sample rotation speed | 15 rpm |
| XRPD method 3 (About 2 min, for salt screening samples) | |
| Detector | LYNXEYE_XE_T(1D mode) |
| Open angle | 2.94° |
| Scan mode | Continuous PSD fast |
| Radiation | Cu/K-Alpha1 (λ = 1.5418Å) |
| X-ray generator power | 40 kV, 40 mA |
| Step size | 0.02° |
| Time per step | 0.06 second per step |
| Scan range | 3° to 40° |
| Primary beam path slits | Twin_Primary motorized slit 10.0 mm by sample length; SollerMount axial soller 2.5° |
| Secondary beam path slits | Detector OpticsMount soller slit 2.5°; Twin_Secondary motorized slit 5.2 mm |
| Sample rotation speed | 15 rpm |
| Differential Scanning Calorimetric (DSC) | |
| Instrument | TA Discovery 2500 or Q2000 |
| Sample pan | Tzero pan and Tzero hermetic lid with a pin hole |
| Temperature range | 30 to 250° C. or 30 to 300° C. or before decomposition |
| Heating rate | 10° C./min |
| Nitrogen flow | 50 mL/min |
| Sample mass | ~0.5-2 mg |
| Thermal Gravimetric Analysis (TGA) | |
| Instrument | Discovery 5500 or Q5000 |
| Sample pan | Aluminum, open |
| Nitrogen flow | Balance 10 mL/min; sample 25 mL/min |
| Start temperature | Ambient condition (below 35° C.) |
| Final temperature | 300° C. or abort next segment if weight <80% (w/w) (The weight loss of the compound is no more than 20% (w/w)) |
| Heating rate | 10° C./min |
| Sample mass | ~2-10 mg |
| Dynamic Vapor Sorption (DVS) Method 1 (for HCl salt Pattern A, L-tartrtate salt Pattern B and succinate salt Pattern A) | |
| Instrument | Intrinsic, Advantage |
| Total gas flow | 200 sccm |
| Oven temperature | 25° C. |
| Solvent | Water |
| Method | Cycle: 40-0-95-0-40% RH<br>Stage Step: 10%<br>Equilibrium: 0.002 dm/dt (%/min)<br>Minimum dm/dt stability duration: 60 min<br>Maximum dm/dt stage time: 360 min |
| Method 2 (for free form Pattern B) | |
| Instrument | Intrinsic |
| Total gas flow | 200 sccm |
| Oven temperature | 25° C. |
| Solvent | Water |
| Method | Cycle: 40-95-0-95-40% RH<br>Stage Step: 10%<br>Equilibrium: 0.002 dm/dt (%/min)<br>Minimum dm/dt stability duration: 60 min<br>Maximum dm/dt stage time: 360 min |

-continued

| Karl Fischer | |
|---|---|
| Instrument | Mettler Toledo Coulometric KF Titrator C30 |
| Method | Coulometric |

| Polarized Light Microscope (PLM) | |
|---|---|
| Instrument | Olympus BX53LED |
| Method | Crossed polarizer, silicone oil added |

| Nuclear Magnetic Resonance (NMR) | |
|---|---|
| Instrument | Bruker Avance-AV 400M |
| Frequency | 400 MHz |
| Probe | 5 mm PABBO BB-1H/D |
| Number of scan | 8 |
| Temperature | 297.6 K |
| Relaxation delay | 1 second |

| Ion chromatograph (IC) method | |
|---|---|
| Instrument | Metrohm 940 professional IC |
| Sample center | 889 IC |
| Detector | Conductivity detector |
| Eluent (anion) | 3.2 mmol/L $Na_2CO_3$ + 1.0 mmol/L $NaHCO_3$ |
| Eluent (cation) | 2.5 mmol/L MSA |
| Column: | Anion A SUPP 5-150 or Cation Column C4-150 |
| Column temperature: | 30° C. |
| Flow rate: | 0.9 mL/min (cation) or 0.7 mL/min (anion) |
| Injection volume: | 20 μL |

| High Performance Liquid Chromatograph (HPLC) | |
|---|---|
| Instrument | 1260 Infinityl Bibary Pump |
| HPLC method 1 (for solubility experiments) | Wave length: 232<br>Column: Zorbax SB-C 18, 150 × 4.6 mm, 3.5 μm<br>Detector: DAD<br>Column temperature: 40° C.<br>Flow rate: 1.2 mL/min<br>Mobile phase A: 0.1% TFA in water<br>Mobile phase B: ACN<br>Diluent: ACN/H2O (1/1,V/V)<br>Injection volume: 5 μL<br>Gradient: |

| | Time (min) | Mobile Phase A (%) | Mobile Phase B (%) |
|---|---|---|---|
| | 0.00 | 95 | 5 |
| | 9.00 | 5 | 95 |
| | 13.00 | 5 | 95 |
| | 13.01 | 95 | 5 |
| | 17.00 | 95 | 5 |

| | |
|---|---|
| HPLC method 2 (for stability experiments) | Wavelength: 230 nm<br>Column: Water Xselect CSH C18, 150 × 4.6 mm, 2.5 μm<br>Detector: DAD<br>Column temperature: 35° C.<br>Flow rate: 1.0 mL/min<br>Mobile phase A: 0.05% TFA in water<br>Mobile phase B: 0.05% TFA in ACN<br>Diluent: MeOH/H2O (1/1, V/V)<br>Injection volume: 6 μL<br>Gradient: |

| | Time (min) | Mobile Phase A (%) | Mobile Phase B (%) |
|---|---|---|---|
| | 0.00 | 85 | 15 |
| | 15.00 | 45 | 55 |
| | 20.00 | 10 | 90 |
| | 23.00 | 10 | 90 |
| | 23.01 | 85 | 15 |
| | 30.00 | 85 | 15 |

Example 1—Synthesis of Compound of Formula (VI)

Reaction scheme 1 below illustrates the overall route developed for the synthesis of compounds of Formula (VI).

Reaction scheme 1

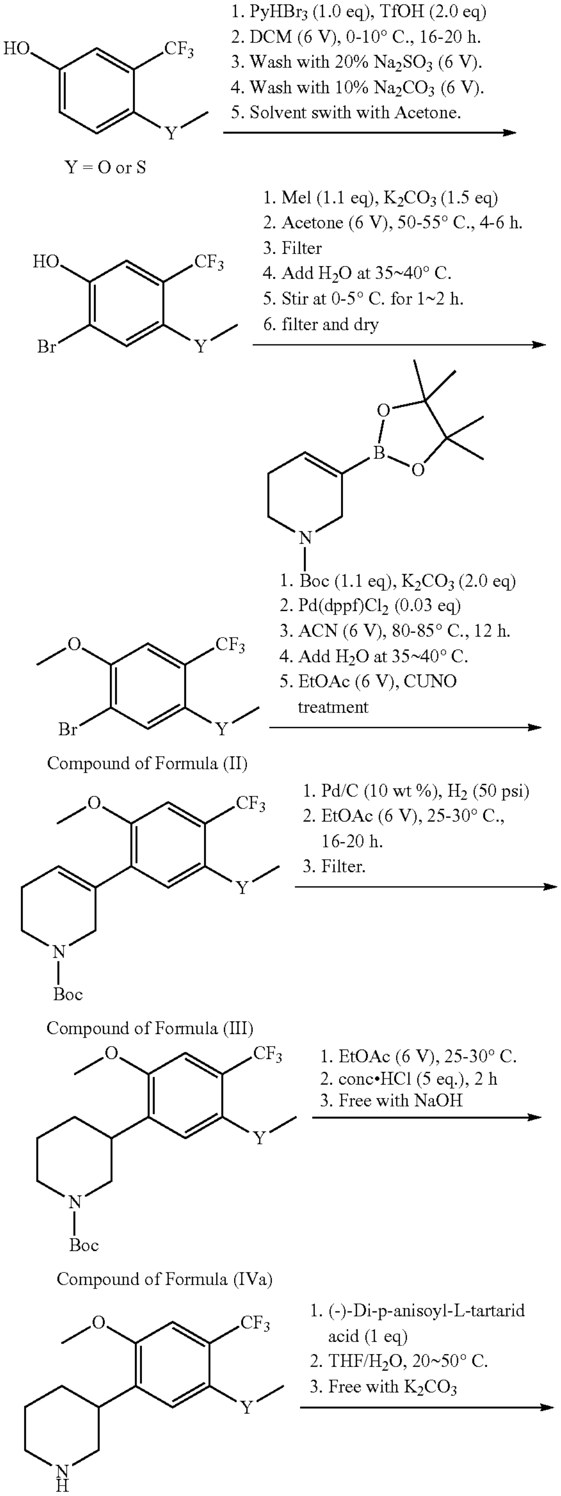

-continued

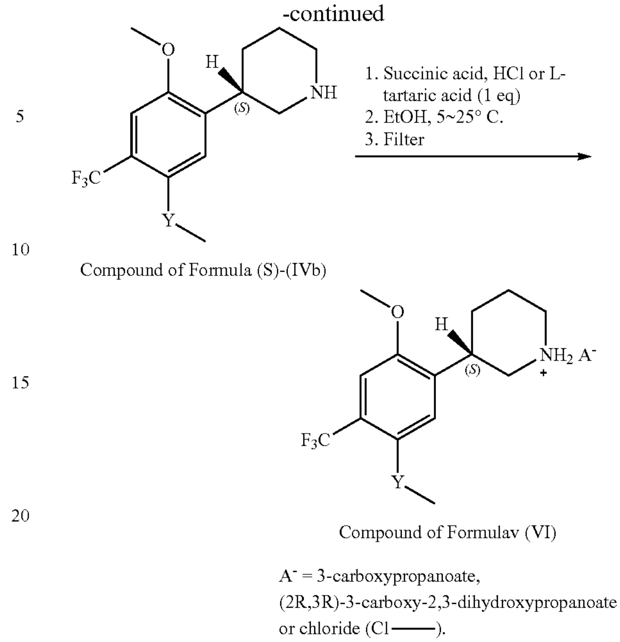

Synthesis of 2-bromo-4-methoxy-5-(trifluoromethyl)phenol (2)

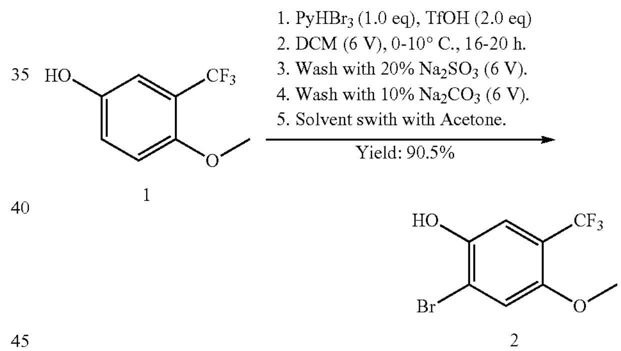

1. Set up a 2 L jacket flask equipped with an overhead stirrer. 2. Charge 1 (100 g, 1.0±0.05×) into R1 under N2. 3. Charge DCM (750~850 g, 7.5~8.5×, 6V) into R1 under $N_2$. 4. Adjust R1 to 0-10° C. 5. Add TfOH (156.2 g, 1.56-1.60×, 2.0 eq) into R1 over 1 hrs at 0-10° C. 6. Add $PyHBr_3$ (166.5 g, 1.66-1.68×, 1.0 eq) into R1 over 1 hrs at 0-10° C. 7. Stir R1 for 16~20 hrs at 0-10° C. 8. Add $PyHBr_3$ (8 g, 0.05-0.20×, 0.05 eq) into R1 at 0-10° C. 9. Stir R1 for 6-12 hrs at 0-10° C. 10. Add 20% $Na_2SO_3$ (550~650 g, 5.5~6.5×, 6 V) over 1 hrs under 0-10° C. 11. Adjust R1 to 15-25° C. 12. Stir R1 at 15-25° C. for 1-2 hrs. 13. Stand R1 for 1-2 hrs. 14. Separate the bottom layer and remove the upper layer. 15. Add 7% $NaHCO_3$ (950~1150 g, 8.5~11.5×, 10 V) to adjust PH=7-9 under 15-25° C. 16. Stir R1 at 15-25° C. for 1-2 hrs. 17. Stand R1 for 1-2 hrs. 18. Separate the bottom layer and remove the upper layer. 19. Charge DCM (600-700 g, 6.0-7.0×, 5V) under 15-25° C. 20. Stand R1 for 1-2 hrs. 21. Separate the bottom layer and remove the upper layer. 22. Charge sat. NaCl (550~650 g, 5.5~6.5×, 6V) under 15-25° C. 23. Stir R1 at 15-25° C. for 1-2 hrs. 23. Stand R1 for 1-2 hrs. 24. Separate the bottom layer and remove the upper layer. 25. Concentrate R1 to 1-3× below 40° C. under vacuum. 26. Charge acetone (468 g, 4.5-5.0×, 6V) into R1. 26. Concentrate R1 to 1-3× below 40° C. under vacuum. 27. Charge acetone (468 g, 4.5-5.0×, 6V) into R1. Compound 2 is obtained as a solution in acetone. Lab yield: ~90%. 1. $^1$H NMR: 400 MHz, $CDCl_3$ δ 7.20 (s, 1H), 7.10 (s, 1H), 3.87 (s, 3H)

Synthesis of 1-bromo-2,5-dimethoxy-4-(trifluoromethyl)benzene (3)

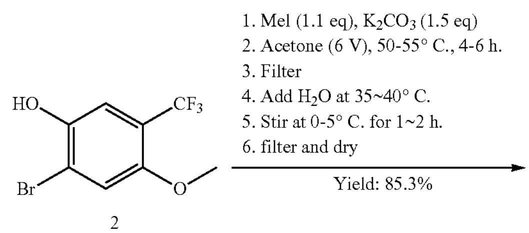

2

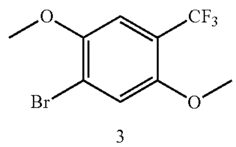

3

1. Set up a 2 L jacket flask equipped with an overhead stirrer. 2. Charge acetone solution of 2 (100 g, 1.0× (0.98-1.02×), 1.0 eq.) into R1. 3. Charge $K_2CO_3$ (76.5 g, 0.77× (0.72-0.80×), 1.52 eq.) into R1. 4. Charge MeI (62.45 g, 0.62×(0.59-0.65×), 1.20 eq.) into R1. 5. Adjust R1 to 30° C. (25~35° C.) under $N_2$ flow. 6. Stir R1 for 18 h (16~20 h) at 30° C. (25~35° C.). 7. Charge MeI (7.9 g, 0.08×(0.06-0.10×), 0.15 eq.) into R1. 8. Stir R1 for 8 h (6~10 h) at 30° C. (25~35° C.). 9. Filter the suspension and transfer the liquor into R2. 10. Rinse wet cake with Acetone (158 g, 1.58× (1.50-1.66×), 2V (1.90-2.10 V)). 11. Rinse wet cake with Acetone (158 g, 1.58× (1.50-1.66×), 2V (1.90-2.10 V)). IPC: Residual MeI in $K_2CO_3$ cake: 5100 ppm. 12 Concentrate R2 to 3-4 V below 45° C. under vacuum. 13. Adjust R2 to 30-35° C. 14. Charge process water (600 g, 5.9~6.1×) into R1 at 30~35° C. under $N_2$ over 40 min. 15. Stir R2 for 1-2 h at 30-35° C. 16. Adjust R2 to 10-15° C. over 1 hr. 17. Stir R2 for 12-16 h at 10-15° C. 18. Filter the mixture. 19. Wash the cake with (140 g, 1.3-1.5×) solution (acetone/H2O=1/2,V/V). 20. Dry the wet cake at 50-55° C. for 16-24 hr. Compound 3 is obtained as a solid. Lab yield: ~85%. $^1$HNMR: 400 MHz, $CDCl_3$δ 7.23 (s, 1H), 7.09 (s, 1H), 3.97 (s, 3H), 3.88 (s, 3H).

Synthesis of tert-butyl 5-(2,5-dimethoxy-4-(trifluoromethyl)phenyl)-3,6-dihydropyridine-1(2H)-carboxylate (4)

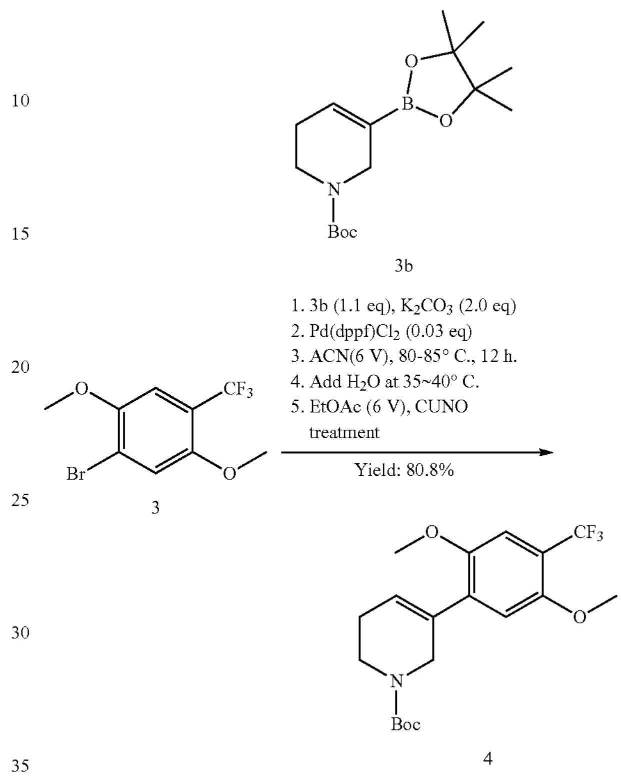

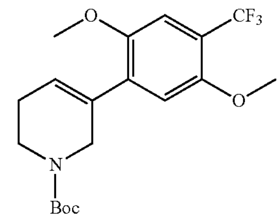

4

1. Set up a 2 L jacket flask equipped with an overhead stirrer. 2. Charge 3 (100 g, 1.0±0.02×) into R1 under $N_2$. 3. Charge 3b (116~120 g, 1.19~1.21×) into R1 under $N_2$. 4. Charge ACN (450~550 g, 4.5~5.5×, 6V) into R1. 5 Charge NaBr aqueous solution (27~30 g, 0.27~0.30×, 0.2V). 6 Charge $K_2CO_3$ (95~98 g, 0.95~1.00×) into R1. 7. Purge R1 with $N_2$ three times. 8. Charge $Pd(dppf)Cl_2·CH_2Cl_2$ (8.4~8.6 g, 0.084~0.086×) into R1. 9. Charge ACN (50-100 g, 0.5~1.0×) into R1. 10. Purge R1 with $N_2$ three times. 11. Adjust R1 to 75-85° C. 12. Stir R1 for 16~24 hrs at 75-85° C. 13. Adjust R1 to 45-55° C. 14. Adjust R1 to 20-40° C. 15. Charge $Pd(dppf)Cl_2·CH_2Cl_2$ (1~3 g, 0.01~0.03×) into R1. 15. Purge R1 with $N_2$ three times. 16. Adjust R1 to 75-85° C. 17. Stir R1 for 6~10 hrs at 75-85° C. 18. Adjust R1 to 45-55° C. 19. Filter the mixture at 45-55° C. 20. Rinse cake with ACN (150-200 g, 1.5-2.0×, 2V). 21. Rinse cake with ACN (150-200 g, 1.5-2.0×, 2V). 22. Charge organic phase into R1. 23. Add process water (800-1200 g, 8.0-12.0×, 8V) over 3 hrs under 45-55° C. 24. Adjust R1 to 0-10° C. over 2 hrs. 25. Stir R1 at 0-10° C. for 4-8 hrs. 26. Filter and wash cake with ACN:H2O=1:3 (V/V) (100-200 g, 1.0-2.0×, 2V). 27. Charge wet cake into R1. 28. Charge ACN (300-400 g, 3.0-4.0×, 4V). 29. Adjust R1 to 45-55° C. 30. Add process water (400-500 g, 4.0-5.0×, 4V) over 3 hrs under 45-55° C. 31. Adjust R1 to 0-10° C. over 2 hrs. 32. Stir the mixture at 0-10° C. for 1-2 hrs. 33. Filter and wash cake with ACN: H2O=1:3(V/V)(100-200 g, 1.0-2.0×, 2V). 34. Charge wet cake into R1.35. Charge EtOAc (900-1000 g, 9.0-10.0×) into R1. 36. Charge silicathiol (10-15 g, 0.1-0.15×,) into R1. 37. Charge EtOAc (300-400 g, 3.0-4.0×) into R1. 38. Adjust R1 to 45-55° C. 39. Stir R1 at 45-55° C. for 12-18 hrs. 40. Adjust R1 to 15-25° C. 41. Stir R1 at 15-25° C. for 1-3 hrs. 42. Filter and wash the cake with EtOAc (90-150 g, 0.9-1.5×, 1V). 43. Decolor organic layer in R1 by CUNO (CUNO Equipment; Supplier: 3M; Model: Zetacarbon; Zeta Plus Activated Carbon, Supplier: 3M; Grade: R55SP; Carbon content: 1.4 g; Gross weight: 3 g; Size: 47*6 mm) at 25-35° C. for 10-16 hrs. 44. Wash the CUNO with EtOAc (200-400 g, 2.0-4.0×, 3V) for 2-4 hrs. 45. Wash the CUNO with EtOAc (200-400 g, 2.0-4.0×, 3V) for 2-4 hrs. 46. Wash CUNO with EtOAc (200-400 g, 2.0-4.0×, 3V) for 3-6 hrs. 47. Concentrate R1 to 2-3× below 40° C. under vacuum. 48. Charge EtOAc (600-700 g, 6.0-7.0×) into R1. Lab yield: ~80%. The compound 4 is obtained as an off-white solid, which is confirmed by 1H-NMR. $^1$H-NMR: 400 MHz, $CDCl_3$ δ 7.07 (s, 1H), 6.85 (s, 1H), 5.95 (m, 1H), 4.22 (m, 2H), δ 3.89 (s, 3H), 3.82 (s, 3H), 3.61-3.58 (t, J=5.6 Hz, 3H), 2.33 (m, 2H), 1.50 (s, 9H).

Synthesis of 3-(2,5-dimethoxy-4-(trifluoromethyl)phenyl)piperidine (6)

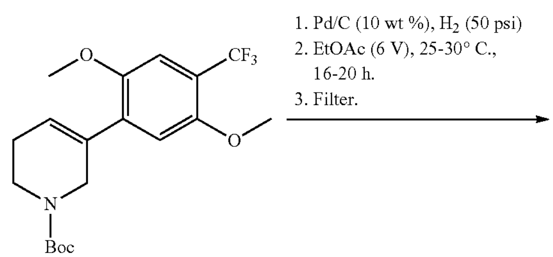

4

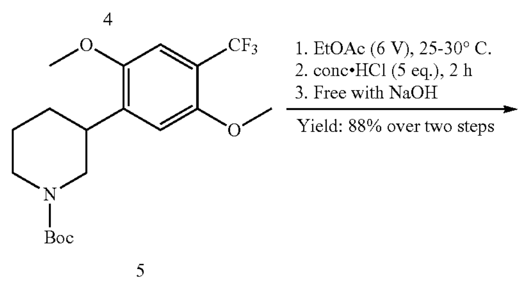

5

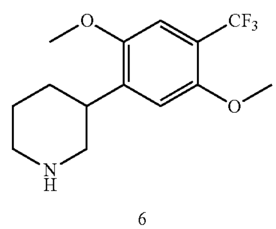

6

1. Set up a 2 L jacket flask equipped with an overhead stirrer. 2. Charge EtOAc solution of 4 (net: 100 g, 1.0×, 1.0 eq.) into R1 under $N_2$. 3. Charge EtOAc (890 g, 8.9×, 10 V) into R1 under N2. 4. Charge Wet Pd/C (10.0 g, 0.1×) into R1 under $N_2$. 5. Purge R1 with H2 under 0.5-1 Mpa three times. 6. Adjust R1 to 0.5-1 Mpa under H2 flow. 7. Adjust R1 to 25-35° C. 8. Stir R1 for 20~24 h at 25-35° C. 9. Charge Wet Pd/C (2.5 g, 0.025×) into R1 under $N_2$. 10. Purge R1 with H2 under 0.5-1 Mpa three times. 11. Adjust R1 to 0.5-1 Mpa under $H_2$ flow. 12. Adjust R1 to 25-35° C. 13. Stir R1 for 20~24 h at 25-35° C. 14. Filter the mixture with a diatomite (0.5×-2.0×) pad. 15. Wash the pad with EtOAc (160-240 g, 1.6-2.4×). 16. Combine the EtOAc solution and transfer to R2. 17. Concentrate the organic phase to 7-9V below 50° C. Compound 5 is obtained as a solid. $^1$H-NMR for 5. δ 7.04 (s, 1H), 6.85 (s, 1H), 4.17-4.14 (d, J=12.0 Hz, 1H), 3.86 (s, 3H), 3.83 (s, 3H), 3.13-3.10 (m, 1H), 2.79 (s, 1H), 1.96-1.94 (d, J=9.20 Hz, 1H), 1.75 (s, 1H), 1.69-1.61 (m, 3H), 1.47 (s, 9H). 18. Adjust R2 to 10-15° C. 19. Add Conc. HCl (135 g, 1.30-1.40×, 5.0 eq) into R2 over 1 h at 10-15° C. 20. Adjust R2 to 25-30° C. 21. Stir R2 for 16~20 h at 25-35° C. 22. Adjust R2 to 10-15° C. 23. Add Conc. HCl (26 g, 0.2-0.3×, 1.0 eq) into R2 over 1 h at 10-15° C. 24. Stir R2 for 8~10 h at 25-35° C. 25. Add 2N NaOH aq. (650-900 g, 6.5-9.0×) into R2 to adjust pH to 8-9 at 10-30° C. 26. Stir R2 at 15-25° C. for 1-2 h. 27. Stand R2 for 1-2 h. 28. Separate the water phase. 29. Transfer the aqueous layer into R2. 30. Charge EtOAc (160-240 g, 1.6-2.4×) into R2. 31. Stir R2 at 15-25° C. for 1-2 hrs. 32. Let R2 stand for 1-2 hrs. 33. Separate the water phase. 34. Combine the organic phases. 35. Wash the combined organic phase with 10% NaCl aq. (500~700 g, 5.0~7.0×). 36. Stir R2 at 15-25° C. for 1-2 hrs. 37. Let R2 stand for 1-2 hrs. 38. Separate the water phase. 39. Concentrate the organic phase to 5-6V below 50° C. Lab yield: ~88% over two steps. Compound 6 (130 g, crude) is obtained as an off-white solid, which is confirmed by 1H NMR. $^1$H NMR: 400 MHz, MeOD δ 7.14 (s, 1H), 7.04 (s, 1H), 3.89 (s, 3H), 3.86 (s, 3H), 3.34-3.32 (m, 2H), 3.25-3.22 (m, 2H) 2.88-2.81 (m, 2H), 1.97-1.94 (m, 2H), 1.85-1.79 (m, 2H).

Synthesis of 3-(2,5-dimethoxy-4-(trifluoromethyl)phenyl)piperidine (8)

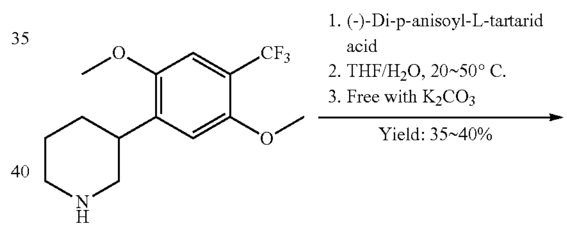

6

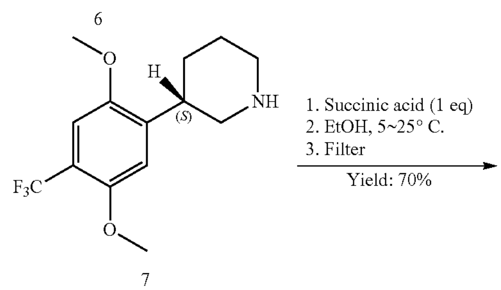

7

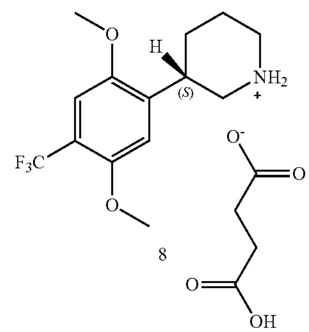

8

1. Set up a 3 L jacket flask equipped with an overhead stirrer. 2. Charge 6 (100 g, 1.0±0.02×) into R1 under $N_2$. 3. Charge THF (850~950 g, 8.5~9.5×, 10 V) into R1. 4. Charge process water (90~110 g, 2.8~3.2×, 1V). 5. Adjust R1 to 25-35° C. 5. Charge (2R,3R)-2,3-bis[(4-methoxybenzoyl) oxy]butanedioic acid (144~146 g, 1.44~1.46×) into R1. 6. Adjust R1 to 45-55° C.

Stir R1 for 10-16 hrs at 45-55° C. 7. Adjust R1 to 30-40° C. 8. Concentrate R1 to 2-4V under 40° C. under vacuum. 9. Charge DCM (900-1000 g, 9.0-10.0×, 7V). 10. Concentrate R1 to 2-4V under 40° C. under vacuum. 11. Charge DCM (900-1000 g, 9.0-10.0×, 7V). 12. Stir R1 for 3~6 hrs at 35-45° C. 13. Adjust R1 to 20-30° C. 14. Stir R1 for 10~16 hrs at 20-30° C. 15. Filter the mixture. IPC: ee % of 7 (as di-anisoyl-tartrate salt) in wet cake≥98.0%. 16. Charge wet cake into R1. 17. Charge DCM (1300~1400 g, 13.0~14.0×, 10 V) into R1. 18. Adjust R1 to 35-45° C. 19. Stir R1 for 1~3 hrs at 35-45° C. 20. Adjust R1 to 20-30° C. 21. Stir R1 for 3~6 hrs at 20-30° C. 22. Filter the mixture. 23. IPC: ee % of 7 (as di-anisoyl-tartrate salt) in wet cake≥98.0%. 7 (as di-anisoyl-tartrate salt)$^1$H NMR: 400 MHz, MeOD δ 8.09-8.06 (m, 4H), 7.15 (s, 1H), 7.02-6.97 (m, 5H), 5.88 (s, 2H), 3.88-3.84 (m, 12H), 3.34-3.32 (m, 3H), 3.09-3.03 (t, J=12.0 Hz, 1H), 2.97 (m, 1H), 2.00 (m, 1H), 1.91-1.87 (m, 3H). 24. Charge wet cake into R1. 25. Charge EtOAc (450-500 g, 4.5-5.0×, 5V) into R1. 26. Charge 20% $Na_2CO_3$ (450-500 g, 4.5-5.0 V, 5V) aqueous phase into R1. 27. Stir R1 for 2~4 hrs at 20-30° C. 28. Let R1 settle for 1-2 hrs. 29. Separate the upper layer and remove the bottom layer. 30. Charge 20% $Na_2CO_3$ (450-500 g, 4.5-5.0 V, 5V) aqueous phase into R1. 31. Stir R1 for 1~3 hrs at 20-30° C. 32. Settle R1 for 1-2 hrs. 33. Separate the upper layer and remove the bottom layer. 34. Concentrate R1 to 2-3V under 40° C. under vacuum. Lab yield of 7: 35-40%. $^1$H-NMR: 400 MHz, MeOD δ 7.14 (s, 1H), 6.99 (s, 1H), 3.86-3.84 (d, 6H), 3.21 (m, 1H), 3.08-3.05 (m, 2H), 2.65-2.58 (m, 2H), 1.90-1.64 (m, 4H). 35. Charge EtOH (450-500 g, 4.5-5.0×, 5V) into R1. 36. Concentrate R1 to 2-3V under 40° C. under vacuum. 37. Charge EtOH (50-300 g, 0.5-3.0×, 2V) into R1. 38. Charge succinic acid (15-25 g, 0.15-0.25×) into R1. 39. Adjust R1 to 45-55° C. 40. Stir R1 for 3~6 hrs at 45-55° C. 41. Adjust R1 to 20-30° C. over 3 hrs. 42. Stir R1 for 16~20 hrs at 20-30° C. 43. Filter the mixture. 44. Dry the wet cake at 35-45° C. for 18-24 hrs. Lab yield of 8: ~70%. $^1$H-NMR: 400 MHz, MeOD δ 7.16 (s, 1H), 7.08 (s, 1H), 3.89 (d, 6H), 3.46-3.43 (m, 3H), 3.15-3.02 (m, 2H), 2.53 (s, 4H), 2.08-1.89 (m, 4H).

The same procedure described above may be used for the synthesis of compounds of Formula (VI), when Y is S, by using a compound of Formula (II) shown below wherein X is Cl, Br, or I.

(II)

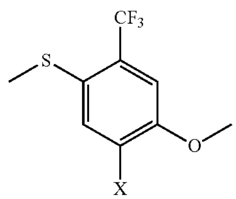

A compound of Formula (II), wherein Y is S, may also be prepared as illustrated in the reaction scheme below from commercially available 4-fluoro-3-(trifluoromethyl)phenol. The brominating agent may be substituted with a chlorinating agent, or an iodinating agent disclosed herein to obtain (5-chloro-4-methoxy-2-(trifluoromethyl)phenyl)(methyl) sulfane or (5-iodo-4-methoxy-2-(trifluoro methyl)phenyl) (methyl)sulfane, respectively, if desired.

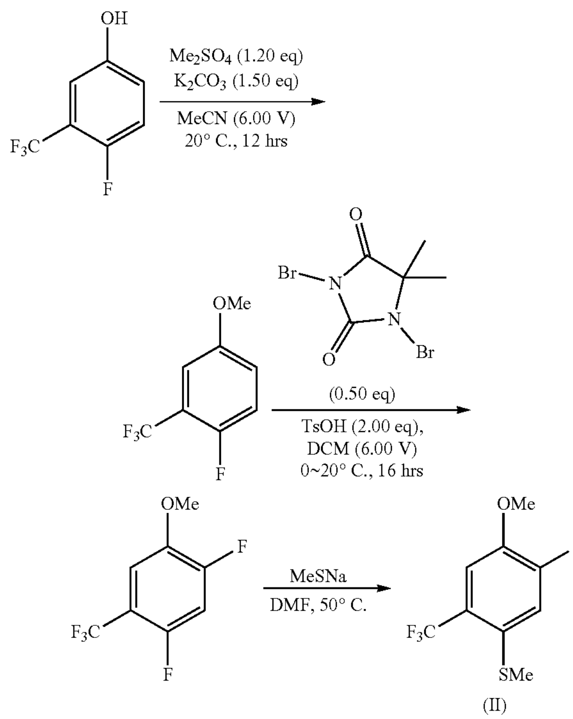

(II)

Example 1A—Synthesis of Compound of Formula (VI)

Reaction scheme 1A below illustrates the alternative route for the synthesis of compounds of Formula (VI), wherein the deprotection is performed prior to hydrogenation.

Reaction scheme 1A

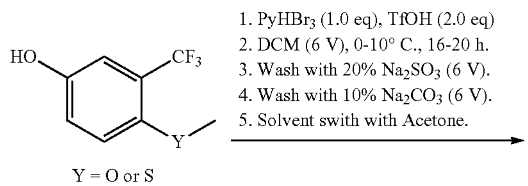

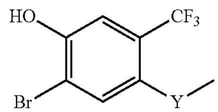

1. MeI (1.1 eq), $K_2CO_3$ (1.5 eq)
2. Acetone (6 V), 50-55° C., 4-6 h.
3. Filter
4. Add $H_2O$ at 35~40° C.
5. Stir at 0-5° C. for 1~2 h.
6. filter and dry -continued

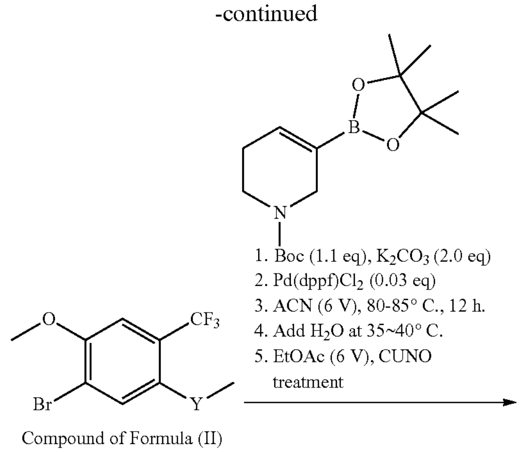

Compound of Formula (II)

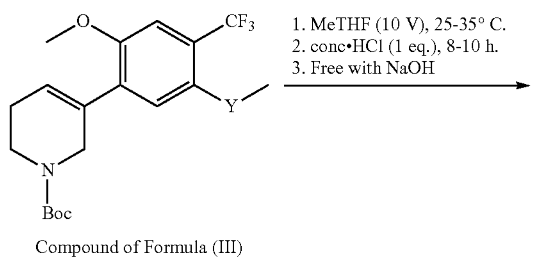

Compound of Formula (III)

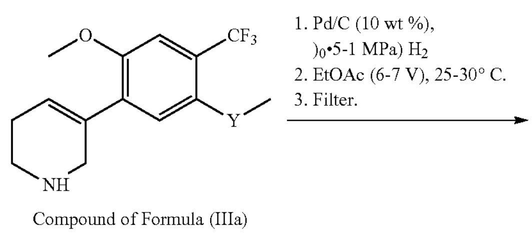

Compound of Formula (IIIa)

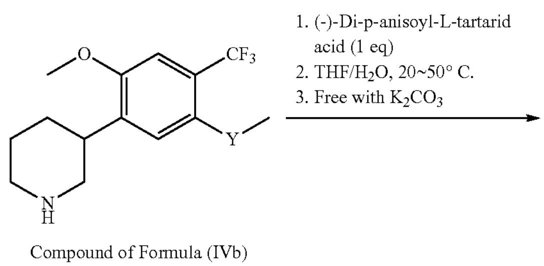

Compound of Formula (IVb)

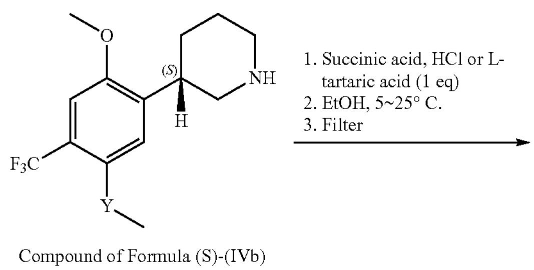

Compound of Formula (S)-(IVb)

-continued

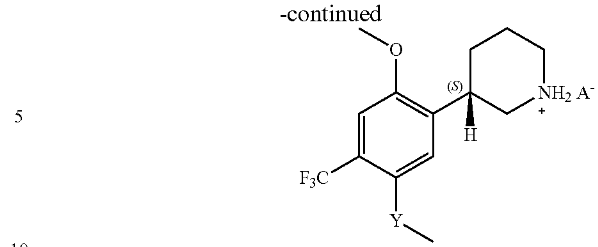

Compound of Formulav (VI)

$A^-$ = 3-carboxypropanoate, (2R,3R)-3-carboxy-2,3-dihydroxypropanoate or chloride (Cl——).

Synthesis of 2-bromo-4-methoxy-5-(trifluoromethyl)phenol (2)

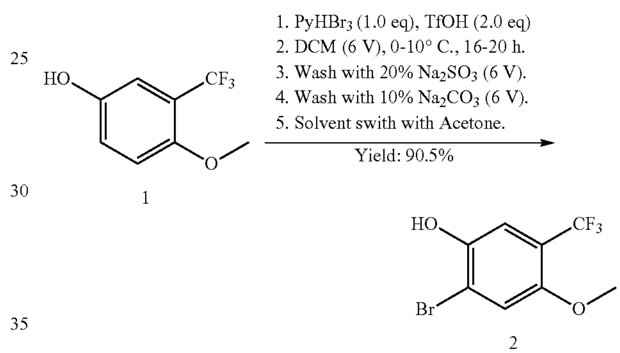

1

2

1. Set up a 2 L jacket flask equipped with an overhead stirrer. 2. Charge 1 (100 g, 1.0±0.05×) into R1 under N2. 3. Charge DCM (750~850 g, 7.5~8.5×, 6V) into R1 under $N_2$. 4. Adjust R1 to 0-10° C. 5. Add $PyHBr_3$ (166.5 g, 1.66-1.68×, 1.0 eq) into R1 at 0-10° C. 6. Add TfOH (156.2 g, 1.56-1.60×, 2.0 eq) into R1 over 2 hrs at 0-10° C. 7. Stir R1 for 16~20 hrs at 0-10° C. 8. Add $PyHBr_3$ (8 g, 0.05-0.20×, 0.05 eq) into R1 at 0-10° C. 9. Stir R1 for 6-12 hrs at 0-10° C. 10. Add 20% $Na_2SO_3$ (550~700 g, 5.5~7.0×, 6 V) over 4 hrs under 0-10° C. 11. Adjust R1 to 15-25° C. 12. Stir R1 at 15-25° C. for 1-2 hrs. 13. Stand R1 for 1-2 hrs. 14. Separate the bottom layer and remove the upper layer. 15. Add 7% $NaHCO_3$ (950~1150 g, 8.5~11.5×, 10 V) to adjust PH=7-9 under 15-25° C. 16. Stir R1 at 15-25° C. for 1-2 hrs. 17. Stand R1 for 1-2 hrs. 18. Separate the bottom layer and remove the upper layer. 19. Charge DCM (600-700 g, 6.0-7.0×, 5V) under 15-25° C. 20. Stand R1 for 1-2 hrs. 21. Separate the bottom layer and remove the upper layer. 22. Charge sat. NaCl (550~650 g, 5.5~6.5×, 6V) under 15-25° C. 23. Stir R1 at 15-25° C. for 1-2 hrs. 23. Stand R1 for 1-2 hrs. 24. Separate the bottom layer and remove the upper layer. 25. Concentrate R1 to 1-3× below 40° C. under vacuum. 26. Charge acetone (468 g, 4.5-5.0×, 6V) into R1. 26. Concentrate R1 to 1-3× below 40° C. under vacuum. 27. Charge acetone (468 g, 4.5-5.0×, 6V) into R1. Compound 2 is obtained as a solution in acetone. Lab yield: ~90%. $^1H$ NMR: 400 MHz, $CDCl_3$ δ 7.26 (s, 1H), 7.14 (s, 1H), 5.94 (broad s, 1H), 3.87 (s, 3H)

Synthesis of 1-bromo-2,5-dimethoxy-4-(trifluoromethyl)benzene (3)

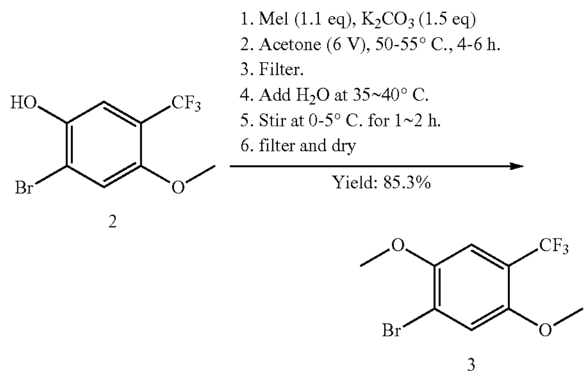

2

3

1. Set up a 2 L jacket flask equipped with an overhead stirrer. 2. Charge acetone solution of 2 (100 g, 1.0× (0.98-1.02×), 1.0 eq.) into R1. 3. Charge $K_2CO_3$ (76.5 g, 0.77× (0.72-0.80×), 1.5 eq.) into R1. 4. Charge MeI (62.45 g, 0.62× (0.59-0.65×), 1.20 eq.) into R1. 5. Adjust R1 to 30° C. (25~35° C.) under $N_2$ flow. 6. Stir R1 for 18 h (16~20 h) at 30° C. (25~35° C.). 7. Charge MeI (7.9 g, 0.08×(0.06-0.10×), 0.15 eq.) into R1. 8. Stir R1 for 8 h (6~10 h) at 30° C. (25~35° C.). 9. Filter the suspension and transfer the liquor into R2. 10. Rinse wet cake with Acetone (158 g, 1.58× (1.50-1.66×), 2V (1.90-2.10 V)). 11. Adjust R2 to 25-35° C. 12. Charge process water (1600 g, 15.0~18.0×) into R1 at 25~35° C. under $N_2$ over 40 min. 13. Stir R2 for 1-2 h at 25-35° C. 14. Adjust R2 to 5-15° C. over 1 hr. 15. Stir R2 for 12-16 h at 5-15° C. 16. Filter the mixture. 17. Wash the cake with (150 g, 1.0-2.0×) solution (acetone/H2O=1/2,V/V). 18. Dry the wet cake at 45-55° C. for 16-24 hr. Compound 3 is obtained as a solid. Lab yield: ~85%. 1HNMR: 400 MHz, $CDCl_3$ δ 7.24 (s, 1H), 7.10 (s, 1H), 3.89 (s, 3H), 3.88 (s, 3H).

Synthesis of tert-butyl 5-(2,5-dimethoxy-4-(trifluoromethyl)phenyl)-3,6-dihydropyridine-1(2H)-carboxylate (4)

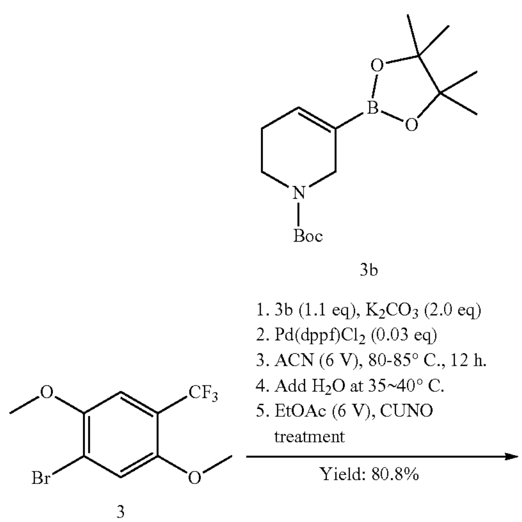

3b

3

-continued

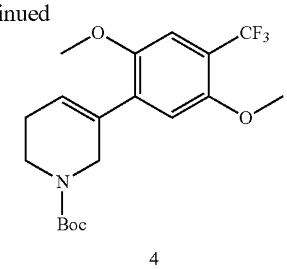

4

1. Set up a 2 L jacket flask equipped with an overhead stirrer. 2. Charge 3 (100 g, 1.0±0.02×) into R1 under $N_2$. 3. Charge 3b (116~120 g, 1.19~1.21×) into R1 under $N_2$. 4. Charge ACN (450~550 g, 4.5~5.5×, 6V) into R1. 5 Charge NaBr aqueous solution (27~30 g, 0.27~0.30×, 0.2V). 6 Charge $K_2CO_3$ (95~98 g, 0.95~1.00×) into R1. 7. Purge R1 with $N_2$ three times. 8. Charge $Pd(dppf)Cl_2{\cdot}CH_2Cl_2$ (8.4~8.6 g, 0.084~0.086×) into R1. 9. Charge ACN (50-100 g, 0.5~1.0×) into R1. 10. Purge R1 with $N_2$ three times. 11. Adjust R1 to 75-85° C. 12. Stir R1 for 16~24 hrs at 75-85° C. 13. Adjust R1 to 45-55° C. 14. Adjust R1 to 20-40° C. 15. Charge $Pd(dppf)Cl_2{\cdot}CH_2Cl_2$ (1~3 g, 0.01~0.03×) into R1. 15. Purge R1 with $N_2$ three times. 16. Adjust R1 to 75-85° C. 17. Stir R1 for 6~10 hrs at 75-85° C. 18. Adjust R1 to 45-55° C. 19. Filter the mixture at 45-55° C. 20. Rinse cake with ACN (150-200 g, 1.5-2.0×, 2V). 21. Charge organic phase into R1. 22. Charge silicathiol (10-15 g, 0.1-0.15×) into R1. 23. Adjust R1 to 45-55° C. 24. Stir R1 at 45-55° C. for 12-18 hrs. 25. Filter and wash cake with ACN (100-200 g, 1.0-2.0×, 2V). 26. Charge the organic phase into R1. 27. Add process water (1000-1500 g, 10.0-15.0×, 11V) over 3 hrs under 45-55° C. 28. Adjust R1 to 0-10° C. over 2 hrs. 29. Stir R1 at 0-10° C. for 4-8 hrs. 26. Filter and wash cake with ACN:H2O=1:3(V/V)(100-200 g, 1.0-2.0×, 2V). 27. Dry the wet cake at 35-45° C. over 10-16 hrs. Lab yield: ~80%. The compound 4 is obtained as an off-white solid, which is confirmed by 1H-NMR. $^1$H-NMR: 400 MHz, $CDCl_3$ δ 7.07 (s, 1H), 6.85 (s, 1H), 5.94 (m, 1H), 4.22 (m, 2H), δ 3.89 (s, 3H), 3.83 (s, 3H), 3.61-3.58 (t, J=5.6 Hz, 3H), 2.33 (m, 2H), 1.54 (s, 9H).

Synthesis of 3-(2,5-dimethoxy-4-(trifluoromethylphenyl)piperidine (6)

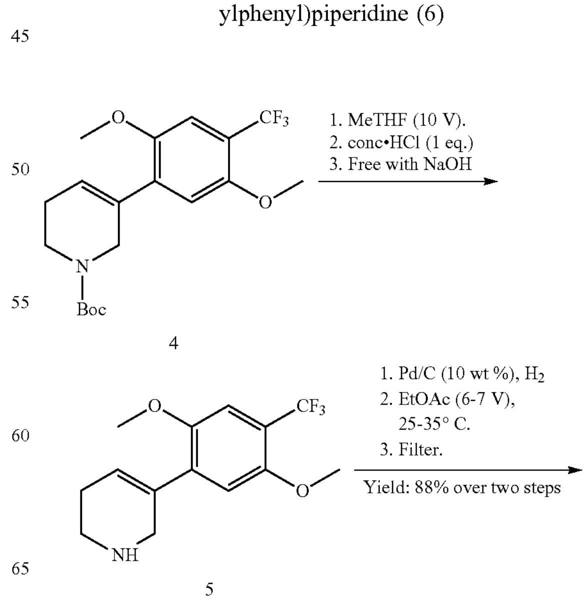

4

5

-continued

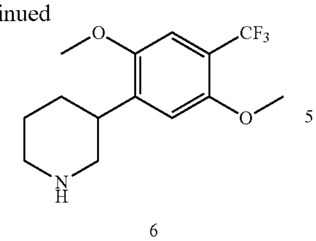

6

1. Set up a 2 L jacket flask equipped with an overhead stirrer. 2. Charge 4 (net: 100 g, 1.0×, 1.0 eq.) into R1 under $N_2$. 3. Charge 2.-MeTHF (860 g, 8.0-9.0×, 10 V) into R1 under N2. 4. Add Conc. HCl (135 g, 1.30-1.40×, 5.0 eq) into R1 over 1 h at 5-15° C. 5. Adjust R1 to 25-35° C. 6. Stir R1 for 16~20 h at 25-35° C. 7. Adjust R1 to 5-15° C. 8. Add Conc. HCl (26 g, 0.2-0.3×, 1.0 eq) into R1 over 1 h at 5-15° C. 9. Stir R1 for 8~10 h at 25-35° C. 10. Adjust R1 to 0-10° C. 11. Add 3N NaOH aq. (800-1500 g, 8.0-15.0×) into R1 to adjust pH to 10-13 at 0-25° C. 12. Stir R1 at 15-25° C. for 1-3 h. 13. Stand R1 for 1-2 h. 14. Separate the water phase. 15. Add 3N NaOH aq. (500-700 g, 5.0-7.0×) into R1 to at 0-25° C. 16. Stir R1 at 15-25° C. for 1-3 h. 17. Stand R1 for 1-2 h. 18. Separate the water phase. 19. Charge 20% NaCl aq. (500-700 g, 5.0-7.0 V) into R1 at 15-25° C. 20. Stir R1 at 15-25° C. for 1-3 h. 21. Stand R1 for 1-2 h. 22. Separate the water phase. 23. Concentrate the organic phase to 2-3V below 40° C. under vacuum. 24. Charge EtOAc (630 g, 6.0-7.0 V) into R1. 25. Concentrate the organic phase to 2-3V below 40° C. under vacuum. 26. Charge EtOAc (630 g, 6.0-7.0 V) into R1. Compound 5 is obtained as a solution in EtOAc. 27. Charge Wet Pd/C (8.0 g, 0.07-0.09×) into R2 under $N_2$. 28. Charge organic phase into R2. 29. Purge R2 with $N_2$ under 0.5-1 Mpa three times. 30. Purge R2 with $H_2$ under 0.5-1 Mpa three times. 31. Adjust R2 to 0.5-1 Mpa under $H_2$ flow. 32. Adjust R2 to 25-35° C. 33. Stir R2 for 20~24 h at 25-35° C. 34. Charge Wet Pd/C (2.5 g, 0.025×) into R2 under $N_2$. 35. Purge R2 with $N_2$ under 0.5-1 Mpa three times. 36. Purge R2 with $H_2$ under 0.5-1 Mpa three times.37. Adjust R2 to 0.5-1 Mpa under $H_2$ flow. 38. Adjust R2 to 25-35° C. 39. Stir R2 for 10~16 h at 25-35° C. 40. Filter the mixture with a diatomite (0.5×-2.0×) pad. 41. Wash the pad with EtOAc (200-300 g, 2.0-3.0×). 42. Combine the EtOAc solution.

Lab yield: ~88% over two steps. Compound 6 (130 g, crude) is obtained as an off-white solid, which is confirmed by 1H NMR. $^1$H NMR: 400 MHz, MeOD δ 7.11 (s, 1H), 7.02 (s, 1H), 3.86 (s, 3H), 3.84 (s, 3H), 3.34-3.32 (m, 1H), 3.22-3.20 (m, 2H) 2.86-2.77 (m, 2H), 1.94-1.91 (m, 2H), 1.83-1.77 (m, 2H).

Synthesis of 3-(2,5-dimethoxy-4-(trifluoromethylphenyl)piperidine (8)

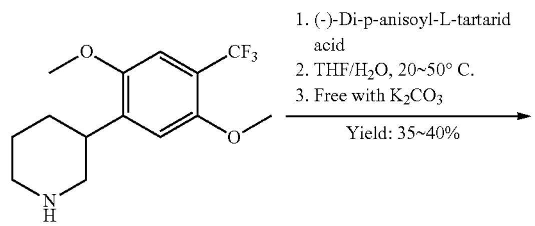

6

-continued

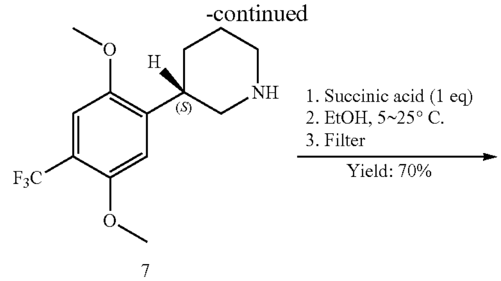

7

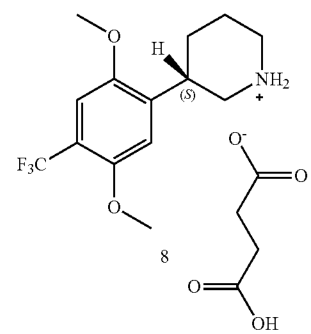

8

1. Set up a 3 L jacket flask equipped with an overhead stirrer. 2. Charge the solution of 6 in EtOAc (100 g, 1.0±0.02×) into R1 under $N_2$. 3. Concentrate R1 to 2-3× below 40° C. under vacuum. 4. Charge THF (850~950 g, 8.5~9.5×, 10 V) into R1. 5. Charge process water (90~110 g, 0.9-1.1×, 1V). 6. Adjust R1 to 25-35° C. 6. Charge (2R,3R)-2,3-bis[(4-methoxybenzoyl)oxy]butanedioic acid (144~146 g, 1.44~1.46×) into R1. 7. Adjust R1 to 45-55° C. 8. Stir R1 for 10-16 hrs at 45-55° C. 9. Adjust R1 to 30-40° C. 10. Concentrate R1 to 2-4V under 40° C. under vacuum. 11. Charge DCM (900-1000 g, 9.0-10.0×, 7V). 12. Concentrate R1 to 2-4V under 40° C. under vacuum. 13. Charge DCM (900-1000 g, 9.0-10.0×, 7V). 14. Stir R1 for 4-8 hrs at 35-45° C. 15. Adjust R1 to 20-30° C. 16. Stir R1 for 4-8 hrs at 20-30° C. 17. Filter the mixture. IPC: ee % of 7 (as di-anisoyl-tartrate salt) in wet cake≥98.0%. 18. Charge wet cake into R1. 19. Charge DCM (1300~1400 g, 13.0~14.0×, 10V) into R1. 20. Adjust R1 to 30-45° C. 21. Stir R1 for 4-6 hrs at 30-45° C. 22. Filter the mixture. 23. IPC: ee % of 7 (as di-anisoyl-tartrate salt) in wet cake≥98.0%. 7 (as di-anisoyl-tartrate salt) 1H NMR: 400 MHz, MeOD δ 8.10-8.06 (m, 4H), 7.15 (s, 1H), 7.02-6.97 (m, 5H), 5.88 (s, 2H), 3.88-3.85 (m, 12H), 3.33-3.32 (m, 3H), 3.09-3.03 (t, J=12.0 Hz, 1H), 2.98-2.97 (m, 1H), 2.00 (m, 1H), 1.91-1.87 (m, 3H). 24. Charge wet cake into R1. 25. Charge EtOAc (450-500 g, 4.5-5.0×, 5V) into R1. 26. Charge 20% $Na_2CO_3$ (550-700 g, 5.5-7.5V, 5V) aqueous solution into R1. 27. Stir R1 for 2~4 hrs at 20-30° C. 28. Let R1 settle for 1-2 hrs. 29. Separate the upper layer and remove the bottom layer. 30. Charge aqueous phase into R1. 31. Charge EtOAc (450-500 g, 4.5-5.0 V, 5V) into R1. 32. Stir R1 for 1~2 hrs at 20-30° C. 33. Settle R1 for 1-2 hrs. 34. Separate the upper layer and remove the bottom layer. 35. Combine the organic phases. 36. Concentrate R1 to 5-6V under 40° C. under vacuum. 37. Charge process water (400-600 g, 4.0-6.0×) into R1. 38. Stir R1 for 1-2 hrs. at 20-30° C. 39. Settle R1 for 1-3 hrs. 40. Separate the upper layer and remove the bottom layer. 41. Charge process water (400-600 g, 4.0-6.0×) into R1. 42. Stir R1 for 1-3 hrs. at 20-30° C. 39. Settle R1 for 1-2 hrs. 43. Separate the upper layer and remove the bottom layer. 44. Concentrate R1 to 2-3V under 40° C. under vacuum. 45. Charge EtOH (450-500 g, 4.5-5.0×). 46. Concentrate R1 to 2-3V under 40° C. under vacuum. 47. Charge EtOH (450-500 g, 4.5-5.0×). Lab yield of 7 in EtOH solution: 35-40%. $^1$H-NMR: 400 MHz, MeOD δ 7.14 (s, 1H), 6.99 (s, 1H), 3.87 (s, 3H), 3.83 (s, 3H), 3.22 (m, 1H), 3.08-3.05 (m, 2H), 2.65-2.59 (m, 2H), 1.90-1.64 (m, 4H). 48. Charge EtOH solution of 7 into R1. 49. Charge succinic acid (15-25 g, 0.15-0.25×) into R1. 39. Adjust R1 to 45-55° C. 40. Stir R1 for 3~6 hrs at 45-55° C. 41. Adjust R1 to 20-30° C. over 3 hrs. 42. Stir R1 for 16~20 hrs at 20-30° C. 43. Filter the mixture. 44. Dry the wet cake at 35-45° C. for 18-24 hrs. Lab yield of 8: ~70%. $^1$H-NMR: 400 MHz, MeOD δ 7.17 (s, 1H), 7.08 (s, 1H), 3.90 (s, 3H), 3.88 (s, 3H), 3.46-3.44 (m, 3H), 3.34-3.32 (m, 1H), 3.16-3.03 (m, 2H), 2.53 (s, 4H), 2.00-1.90 (m, 4H).

Example 2—Synthesis of Compound of Formula (VI)

The compounds of Formula (VI), when Y is S, may also be prepared as illustrated in the reaction scheme below. The chiral resolution may be performed using any of the chiral acids disclosed herein, preferably the chiral acids shown in Table 1.

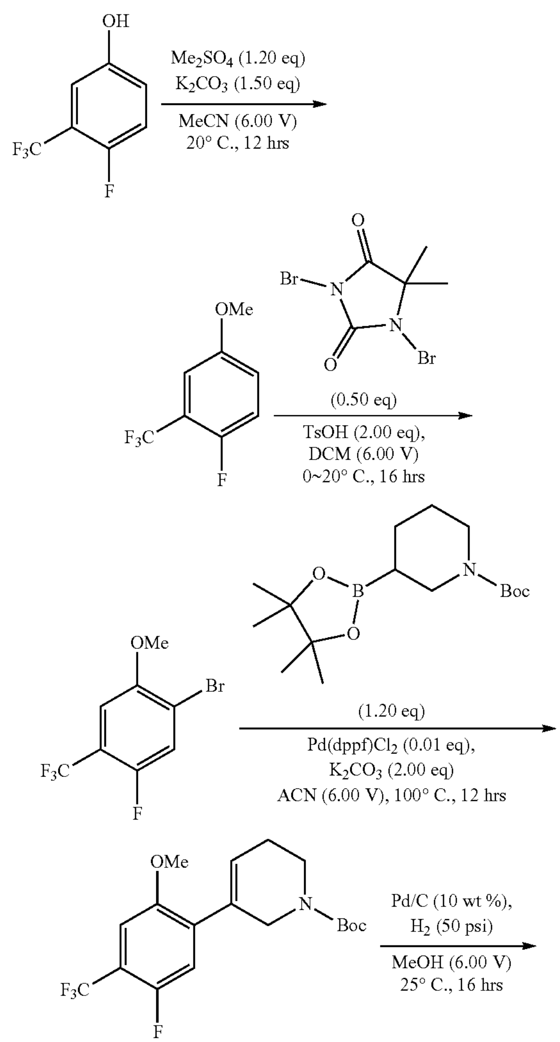

-continued

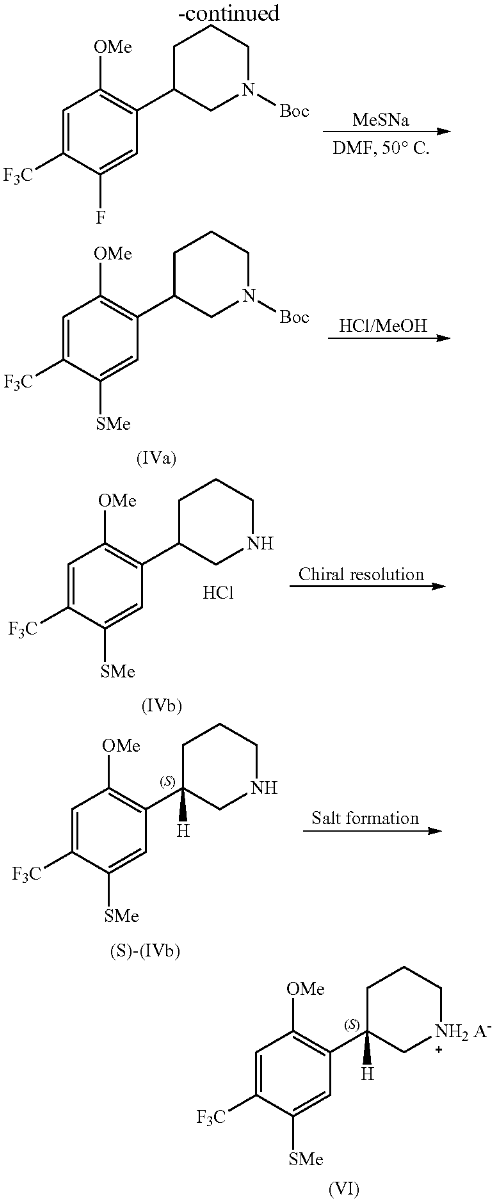

(IVa)

(IVb)

(S)-(IVb)

(VI)

A⁻ = 3-carboxypropanoate, (2R,3R)-3-carboxy-2,3-dihydroxypropanoate or chloride (Cl——).

Example 3: Salt Screening 15 acids were selected as salt-forming agents (see Table 3) with (S)-3-(2,5-dimethoxy-4-(trifluoromethyl)phenyl)piperidine. About 45 mg was added to a suitable solvent and different equivalents of acids were added under stirring at 50° C. for about 2 hours and then at 25° C. for at least 32 hours. Ethanol, acetone, and ACN were used as screening solvents. When no precipitation was obtained or only a few solids were obtained, the solutions were placed at 5° C. for crystallization.

Obtained suspensions were taken out and centrifuged. Solids obtained was analysed by XRPD. Salt screening results are summarized in Table 4. Salts with high or medium crystallinity were further characterized (see Table 5).

TABLE 3

| Acids used for salt screening | | | | |
|---|---|---|---|---|
| Counter ions | pKa(s) | M.W. | Class | Equivalents |
| HCl | −6.1 | 36.46 | I | 1 eq. |
| Sulfuric acid | −3, 1.92 | 98.08 | I | 1 eq. |
| Phosphoric acid | 1.96, 7.12, 12.32 | 98 | I | 1 eq. |
| L-malic acid | 3.4, 5.09 | 134.09 | I | 1 eq. |
| L-tartaric acid | 3.02, 4.36 | 150.09 | I | 0.5 or 1 eq. |
| Citric acid | 3.12, 4.76, 6.39 | 192.13 | I | 1 eq. |
| Fumaric acid | 3.03, 4.38 | 116.08 | I | 0.5 or 1 eq. |
| L-aspartic acid | 1.88, 3.65, 9.60(B) | 133.11 | I | 1 eq. |

TABLE 3-continued

| Acids used for salt screening | | | | |
|---|---|---|---|---|
| Counter ions | pKa(s) | M.W. | Class | Equivalents |
| Succinic acid | 4.2, 5.63 | 118.09 | I | 0.5 or 1 eq. |
| Adipic acid | 4.44, 5.44 | 146.14 | I | 1 eq. |
| Acetic acid | 4.76 | 60.05 | I | 1 eq. |
| L-glutamic acid | 2.19, 4.25, 9.67(B) | 147.13 | I | 1 eq. |
| Gentisic acid | 2.93 | 154.12 | II | 1 eq. |
| L-lactic acid | 3.86 | 90.08 | I | 1 eq. |
| D-lactic acid | 3.86 | 90.08 | I | 1 eq. |

TABLE 4

| Salt screening results (slurry crystallization) | | | |
|---|---|---|---|
| Counter ions | A EtOH | B Acetone | C ACN |
| Free form | Clear solution | Clear solution | Clear solution |
| HCl | +(Polymorph A) | +(Polymorph A) | +(Polymorph A) |
| Sulfuric acid | +(Polymorph A) | +(Polymorph A) | +(Polymorph A) |
| Phosphoric acid | Clear solution | +(Polymorph A) | Hazy solution |
| L-malic acid | +(Polymorph A) | +(Polymorph A) | +(Polymorph A) |
| 0.5 equiv. L-tartaric acid | +(Polymorph A) | +(Polymorph A) | +(Polymorph A) |
| 1.0 equiv. L-tartaric acid | +(Polymorph B) | +(Polymorph B) | +(Polymorph B) |
| Citric acid | Clear solution | Clear solution | Clear solution |
| 0.5 equiv. fumaric acid | +(Polymorph A) | +(Polymorph A) | +(Polymorph B) |
| 1.0 equiv. fumaric acid | +(Polymorph C) | +(Polymorph C) | +(Polymorph C) |
| L-aspartic acid | +(Polymorph A) | −(Polymorph A + seven obvious peaks at 2theta 7.4°; 11.1°; 16.1°; 21.7°; 23.6°; 28.7°; 31.4°) | +(Polymorph A) |
| 0.5 equiv. succinic acid | +(Polymorph A) | +(Polymorph A) | +(Polymorph A) |
| 1.0 equiv. succinic acid | +(Polymorph A) | +(Polymorph A) | +(Polymorph A) |
| Adipic acid | Clear solution | +(Polymorph A) | +(Polymorph A) |
| Acetic acid | Clear solution | +(Polymorph A) | +(Polymorph A) |
| Glutamic acid | +(Polymorph A) | +(Polymorph B (low crystallinity)) | +(Polymorph C) |
| Gentisic acid | Clear solution | Clear solution | Clear solution |
| L-lactic acid | Clear solution | Thin suspension | +(Polymorph A) |
| D-lactic acid | +(Polymorph A) | Thin suspension | Clear solution |

(+) shows that a crystalline salt was formed. Polymorph (A, B, C) shows if the different solvents resulted in the same polymorph. (−) physical mixtures.

Example 4: Characterization of Crystalline Hits

According to the salt screening results (see Table 4), totally 19 potential salt hits were identified. All the potential salt hits were further investigated by Differential Scanning Calorimetry (DSC), Thermogravimetric analysis (TGA), H-NMR, Ion chromatography (IC), Karl Fischer titration (KF), and Polarized Light Microscopy (PLM) to confirm their identity and evaluate their physicochemical properties as shown in Table 5 below.

TABLE 5

| Physicochemical properties of salts | | | | | | | | |
|---|---|---|---|---|---|---|---|---|
| | Crystal-linity | Melting onset (° C.) | Enthalpy (J/g) | Weight loss (%) | Stoichiometric ratio (base:acid) | Residual solvent (% w/w) | Water content (% w/w) | Hygroscopicity (water uptake % w/w) |
| Free base Polymorph B | High | Dehydration: 53.4; Melting: 80.0 | Dehydration 180; Melting enthalpy 68 | 8.0% at 100° C. | // | None | 8% | // |

TABLE 5-continued

Physicochemical properties of salts

| | Crystal-linity | Melting onset (° C.) | Enthalpy (J/g) | Weight loss (%) | Stoichiometric ratio (base:acid) | Residual solvent (% w/w) | Water content (% w/w) | Hygroscopicity (water uptake % w/w) |
|---|---|---|---|---|---|---|---|---|
| HCl salt Polymorph A from EtOH (anhydrate) | High | Melting: 233.7 | Decomp. upon melting | 0.08% at 180° C. | 1:0.94 | None | // | None |
| Sulfate salt Polymorph A from EtOH (solvate) | High | Endothermic: 40.4, 138.0 Melting: 188.4 | Endothermic: 111.9 Decomp. upon melting | 8.2% at 130° C. | 1:1.2 | 5.2% EtOH | // | // |
| Phosphate salt Polymorph A from Acetone (anhydrate) | Medium | Melting: 214.1 | Decomp. upon melting | 0.7% at 200° C. | // | None | // | // |
| L-malate salt Polymorph A from EtOH (hydrate) | High | Dehydration 36.9; Melting: 149.5 | Dehydration 12; Decomp. upon melting | 2.3% at 148° C. | 1:1.2 | None | 5.9% | Slightly hygroscopic (~0.3%) |
| Hemi L-tartrate salt Polymorph A from EtOH (monohydrate) | Medium | Dehydration 62.7; Melting: 203.2 | Dehydration 70; Decomp. upon melting | 4.0% at 130° C. | 1:0.62 | None | 4.6% | // |
| L-tartrate salt Polymorph B from EtOH (anhydrate) | High | Melting: 206.6 | Decomp. upon melting | 0.9% at 170° C. | 1:1.03 | 0.4% EtOH | // | None |
| Hemi-fumarate salt Polymorph A (monohydrate) | Medium | Dehydration 43.1; Melting: 167.7 | Dehydration 55; Decomp. upon melting | 4.8% at 120° C. | 1:0.54 | None | 5.5% | // |
| Hemi-fumarate salt Polymorph B from EtOH (dihydrate) | Medium | Dehydration 56.4; Melting: 162.2 | Dehydration 186; Decomp. upon melting | 9.4% at 100° C. | 1:0.51 | None | 9.3% | // |
| Mono-fumarate salt Polymorph C from EtOH (anhydrate) | Medium | Melting: 199.5 | Decomp. upon melting | 0.6% at 150° C. | 1:0.93 | None | // | Slightly hygroscopic (~0.2%) |
| L-aspartate salt Polymorph A from EtOH (hydrate) | High | Dehydration 79.5; Melting: 159.2 | Dehydration 104; Decomp. upon melting | 3.9% at 110° C. | 1:0.95 | None | 7.0% | Hygroscopic (~4.3%) |
| Succinate salt Polymorph A from EtOH (anhydrate) | Medium/High | Melting: 165.4 | Decomp. upon melting | 2.1% at 135° C. | 1:0.97 | None | // | Slightly hygroscopic (~0.7%) |
| Hemi-succinate salt Polymorph B from ACN (hydrate) | Medium | Dehydration: 61.7, 97.8 Melting: 135.8 | Dehydration: 107 Decomp. upon melting | 4.8% at 90° C. | 1:0.57 | None | 6.1% | Hygroscopic (~1.8%) |
| Hemi-adipate salt Polymorph A from EtOH (hydrate) | High | Dehydration: 45.5 Melting: 159.2 | Dehydration: 112 Decomp. upon melting | 5.0% at 120° C. | 1:0.63 | None | // | None |
| Acetate salt Polymorph A from EtOH (anhydrate) | High | Melting: 144.3 | Decomp. upon melting | 0.2% at 80° C. | 1:0.92 | None | // | None |

TABLE 5-continued

| Physicochemical properties of salts | | | | | | | | |
|---|---|---|---|---|---|---|---|---|
| | Crystal-linity | Melting onset (° C.) | Enthalpy (J/g) | Weight loss (%) | Stoichiometric ratio (base:acid) | Residual solvent (% w/w) | Water content (% w/w) | Hygroscopicity (water uptake % w/w) |
| L-glutamate salt Polymorph A from EtOH (hydrate) | Low | Multiple thermal events | Multiple thermal events | 4.8% at 100° C. | 1:0.92 | None | 8.6% | // |
| L-glutamate salt Polymorph B from Acetone (dihydrate) | Medium | Multiple thermal events | Multiple thermal events | 6.6% at 100° C. | 1:1.01 | 0.5% Acetone | 6.9% | // |
| L-glutamate salt Polymorph C from ACN (dihydrate) | High | Multiple thermal events | Multiple thermal events | 6.3% at 100° C. | 1:0.98 | None | 8.7% | // |
| L-lactate salt Polymorph A from ACN (monohydrate) | High | Dehydration: 68.4 Melting: 152.4 | Dehydration 168 Decomp. upon melting | 4.9% at 100° C. | 1:1.18 | None | 5.1% | None |
| D-lactate salt Polymorph A from EtOH (anhydrate) | High | Melting: 154.2 | Decomp. upon melting | // | 1:1.14 | None | // | // |

Explanation"//": Not carried out.

Amongst the salts tested in Table 5, hydrochloride salt (polymorph A), L-tartrate salt (polymorph B) and succinate salt (polymorph A) performed overall better than the other salts and showed good physicochemical characteristics including high crystallinity, high melting point, reasonable stoichiometry and good counter ion safety. Therefore, these three salts were selected as candidates.

HCl salt (polymorph A) preparation. 1600 mg of free base (Polymorph B) was weighed into a 20 mL glass vial and 4.2 mL ethanol was added into the vial under stirring at 50° C. for about 5 min. (Clear solution) 2. 1.79 mL (~1.05 equiv.) HCl solution (mixture of 0.2 mL HCl and 1.8 mL ethanol) was added into the solution slowly (Clear solution). 3. About 22.7 mg seeds were added to the solution and kept stirring at 50° C. for about 2 hours (suspension); 4. Cooled naturally to 25° C., then kept stirring at 25° C. for about 4 days and stirring at 5° C. for about 5 hours. 5. The solids were collected by centrifugal filtration and dried at 50° C. for about 16 hours. 6. 461 mg hydrochloride salt (Polymorph A) was obtained as an off-white solid in a yield of 74%. $^1$H NMR: 400 MHz, MeOD δ 7.15 (s, 1H), 7.08 (s, 1H), 3.88 (s, 3H), 3.86 (s, 3H), 3.50-3.42 (m, 3H), 3.40-3.30 (m, 1H), 3.10-3.06 (m, 1H), 2.10-2.06 (m, 1H), 1.98-1.91 (m, 3H).

L-tartrate salt (Polymorph B) preparation. 1600 mg of free base (Polymorph B) and 338 mg L-tartaric acid (~1.05 equiv.) was weighed into a 20 mL glass vial. Then 2 mL ethanol was added into the vial under stirring at 50° C. (thin suspension). After stirring for about 3 min, solids precipitated. 2.4 mL ethanol was added into the solution (suspension); 2. About 36.8 mg seeds were added to the solution and kept stirring at 50° C. for about 2 hours (suspension); 3. Cooled naturally to 25° C., then kept stirring at 25° C. for about 4 days and stirring at 5° C. for about 5 hours. 4. The solids were collected by centrifugal filtration and dried at 50° C. for about 16 hours. 5. 780 mg L-tartrate salt (Polymorph B) was obtained as an off-white solid in a yield of 80%. 1H NMR: 400 MHz, DMSO δ 7.17 (s, 1H), 7.16 (s, 1H), 3.86-3.83 (m, 8H), 3.31-3.28 (m, 1H), 3.23-3.20 (m, 1H), 3.10-3.06 (m, 1H), 2.85 (m, 1H), 1.90-1.81 (m, 1H), 1.79-1.74 (m, 3H).

Succinate salt (Polymorph A) preparation. 1600 mg of free base (Polymorph B) and 268 mg succinic acid (~1.05 equiv.) was weighed into a 20 mL glass vial. Then 2 mL ethanol was added into the vial under stirring at 50° C. (thin suspension). After stirring for about 3 min, solids precipitated. 2.0 mL ethanol was added into the solution (suspension); 2. About 23.7 mg seeds were added to the suspension. Then 1.2 mL ethanol was added and kept stirring at 50° C. for about 2 hours (suspension); 3. Cooled naturally to 25° C., then kept stirring at 25° C. for about 4 days and stirring at 5° C. for about 5 hours. 4. The solids were collected by centrifugal filtration and dried at 50° C. for about 16 hours. 5. 625 mg succinate salt (Polymorph A) was obtained as an off-white solid in a yield of 70%. 1H NMR: 400 MHz, MeOD δ 7.16 (s, 1H), 7.08 (s, 1H), 3.89 (d, 6H), 3.46-3.43 (m, 3H), 3.15-3.02 (m, 2H), 2.53 (s, 4H), 2.08-1.89 (m, 4H)

Salt Candidate Evaluation

Hydrochloride salt (polymorph A), L-tartrate salt (polymorph B) and succinate salt (Polymorph A) of (S)-3-(2,5-dimethoxy-4-(trifluoromethyl)phenyl)piperide were scaled up and fully evaluated in comparison with the free base (S)-3-(2,5-dimethoxy-4-(trifluoromethyl)phenyl)piperidine (Polymorph B). The scale up batches are the same polymorphs as those of the screening samples. The three salt candidates were evaluated in comparison with free form Polymorph B (i.e. 3-(2,5-dimethoxy-4-(trifluoromethyl) phenyl)piperidine) in terms of physicochemical properties, stability, solubility, hygroscopicity and polymorphic behaviours as shown in Tables 6-10.

TABLE 6

Physicochemical properties of HCl salt (polymorph A), L-tartrate salt (polymorph B), and succinate salt (Polymorph A) on large scale batch

| | Chemical purity (%) | Crystal-linity | Dehydration onset/ Melting onset (° C.) | Dehydration enthalpy/ Melting enthalpy (J/g) | Weight loss (%) at Temperature (° C.) | Stoichiometric ratio | Residual solvent (% w/w) | Water content (% w/w) | Morphology |
|---|---|---|---|---|---|---|---|---|---|
| Free base (Polymorph B) | 98.7 | High | 53.4/ 80.0 | 180/68 | 8.0 at 100 | // | None | 8.0% | Plate-like crystals |
| Hydrochloride salt (Polymorph A, anhydrate) | 99.8 | High | None/ 233.2 | Decomp. upon melting | 0.3 at 160 | 1:0.99 | None | // | Aggregated fine crystals |
| L-tartrate salt (Polymorph B, anhydrate) | 99.5 | High | None/ 203.1 | Decomp. upon melting | 0.4 at 170 | 1:1.00 | None | // | Aggregated fine crystals |
| Succinate salt Polymorph A (anhydrate) | 99.9 | High | None/ 166.4 | Decomp. upon melting | 0.2 at 135 | 1:1.01 | None | // | Rod-like crystals |

Crystallinity and thermal properties: The free base (polymorph B) is a monohydrate containing about 8% water (1.3 equivalent by molar ratio) by Karl Fisher. It is of high crystallinity. DSC shows a dehydration peak at $T_{onset}$ of 53.4° C. with an enthalpy of about 180 J/g, followed by a melting peak at T onset of 80.0° C. with an enthalpy of about 68 J/g. TGA shows about 8% weight loss at about 100° C. No residual solvent was detected by 1H-NMR. The hydrochloride salt (polymorph A) is an anhydrate. It is of high crystallinity. Stoichiometric ratio of free form to hydrochloric acid is 1:0.99 by IC. DSC shows a melting peak at $T_{onset}$ of 233.2° C. Decomposition occurred upon melting. TGA shows about 0.3% weight loss at about 160° C. No residual solvent was detected. The L-tartrate salt Polymorph B is an anhydrate. It is of high crystallinity. Stoichiometric ratio of free form to L-tartaric acid is 1:1.00 based on 1H-NMR. DSC shows a melting peak at $T_{onset}$ of 203.1° C. Decomposition occurred upon melting. TGA shows about 0.4% weight loss at about 170° C. No residual solvent was detected. The succinate salt Polymorph A is an anhydrate. It is of high crystallinity. Stoichiometric ratio of free form to succinic acid is 1:1.01 based on 1H-NMR. DSC shows a melting peak at $T_{onset}$ of 166.4° C. Decomposition occurred upon melting. TGA shows about 0.2% weight loss at about 135° C. No residual solvent was detected.

Stability

The bulk stability of the free base (polymorph B) and the 3 salt candidates were investigated at 25° C./92% RH in an open container, at 40° C./75% RH in an open container and at 60° C. in a tight container over 1 week as shown in Table 7 below.

TABLE 7

Stability of HCl salt (polymorph A), L-tartrate salt (polymorph B), and succinate salt (polymorph A)

| | Initial chemical | Solid state, 25° C./92% RH, open container, 1 week | | Solid state, 40° C./75% RH, open container, 1 week | | Solid state, 60° C., tight container, 1 week | |
|---|---|---|---|---|---|---|---|
| | purity (%) | chemical purity (%) | XPRD | chemical purity (%) | XPRD | chemical purity (%) | XPRD |
| Free base (Polymorph B) | 98.7 | 98.7 | No change | 98.8 | No change | 98.5 | Change to polymorph A |
| Hydrochloride salt (Polymorph A, anhydrate) | 99.8 | 99.8 | No change | 99.8 | No change | 99.8 | No change |
| L-tartrate salt (Polymorph B, anhydrate) | 99.5 | 99.5 | No change | 99.5 | No change | 99.5 | No change |
| Succinate salt Polymorph A (anhydrate) | 99.9 | 99.9 | No change | 99.9 | No change | 99.9 | No change |

Initial chemical purity. The free base (Polymorph B), the hydrochloride salt (Polymorph A), the L-tartrate salt (Polymorph B), and the succinate salt (Polymorph A) have high chemical purity of 98.7%, 99.8%, 99.5% and 99.9%, respectively. The salt formation showed a purification effect.

Bulk stability. The hydrochloride salt (Polymorph A), the L-tartrate salt (Polymorph B), and the succinate salt (Polymorph A) are chemically and physically stable under the stressed conditions.

The free form (Polymorph B) is chemically stable in these conditions, but physically unstable at 60° C. It converted to free base (Polymorph A). Based on this parameter alone, the candidate salts cannot be discriminated.

Solubility

The solubility of the free base (Polymorph B) and the 3 salt candidates were tested in 4 pH buffers (pH 1.2 HCl buffer, pH 4.5 acetate buffer, pH 6.8 phosphate buffer and water) and 3 bio-relevant media (SGF, FaSSIF-V1 and FeSSIF-Vi) at 37° C. for 2 h and 24 h as shown below in Table 8. The solubility was tested up 2 mg/mL.

TABLE 8

Solubility of HCl salt (polymorph A), L-tartrate salt (polymorph B), and succinate salt (Polymorph A) at 37° C. in various buffers and bio-media.

| | pH 1.2 (0.1N HCl) | | pH 4.5 (50 mM) acetate buffer | | pH 6.8 (50 mM) phosphate buffer | | Water | | FeSSIF-V1, pH 5.0 | | FaSSIF-V1, pH 6.5 | | SGF, pH 2.0 | |
|---|---|---|---|---|---|---|---|---|---|---|---|---|---|---|
| Sample | Solubility 2 h (mg/mL) | Solubility 24 h (mg/mL) | Solubility 2 h (mg/mL) | Solubility 24 h (mg/mL) | Solubility 2 h (mg/mL) | Solubility 24 h (mg/mL) | Solubility 2 h (mg/mL) | Solubility 24 h (mg/mL) | Solubility 2 h (mg/mL) | Solubility 24 h (mg/mL) | Solubility 2 h (mg/mL) | Solubility 24 h (mg/mL) | Solubility 2 h (mg/mL) | Solubility 24 h (mg/mL) |
| Free base (Polymorph B) | >2 | >2 | >2 | >2 | 1.54 | 1.58 | 0.11 | 0.14 | >2 | >2 | >2 | >2 | >2 | >2 |
| Hydrochloride salt (Polymorph A, anhydrate) | >2 | >2 | >2 | >2 | 1.52 | 1.50 | >2 | >2 | >2 | >2 | >2 | >2 | >2 | >2 |
| L-tartrate salt (Polymorph B, anhydrate) | >2 | >2 | >2 | >2 | >2 | >2 | >2 | >2 | >2 | >2 | >2 | >2 | >2 | >2 |
| Succinate salt Polymorph A (anhydrate) | >2 | >2 | >2 | >2 | 1.80 | 1.68 | >2 | >2 | >2 | >2 | >2 | >2 | >2 | >2 |

The free base and the three salt candidates showed overall good solubility. Their solubility is >2 mg/ml in most pH buffers and bio-relevant fluids, except in pH 6.8 phosphate buffer. In this buffer, the solubility was ranked as L-tartrate salt (polymorph B)>succinate salt (polymorph A)>HCl salt.

TABLE 9

Solubility of HCl salt (polymorph A), L-tartrate salt (polymorph B), and succinate salt (Polymorph A) at 25° C. in water.

| | | Solubility* (mg/mL) at 25° C. | | | Final |
|---|---|---|---|---|---|
| Sample | Media | 2 hours | 24 hours | 7 days | pH |
| Free base (API) ** | Water | 0.11 | 0.14 | — | 9.06 |
| Succinate salt | | 17.2 | 17.4 | 16.8 | 4.74 |
| HCl salt | | 17.1 | 18.7 | 17.1 | 7.36 |
| L-tartrate salt | | — | — | 6.2 | 4.92 |

*The solubility result is based on the free base in the salt.

The three salt candidates showed overall good solubility in water as shown in Table 9. In water, the solubility was ranked as HCl salt (polymorph A)>succinate salt (polymorph A)>L-tartrate salt (polymorph B). The L-tartrate salt and the succinate salt (1:1) have the benefit of providing increased buffer capacity compared to salts formed from monoprotic acids, such as the HCl salt. Thus, from the solubility data, the succinate salt (polymorph A) appears the most promising salt candidate.

Hygroscopicity

Hygroscopicity of the free base (polymorph B) and the three salt candidates were evaluated by dynamic vapor sorption (DVS) test at 25° C. as shown in Table 10.

TABLE 10

DVS test at 25° C. of HCl salt (polymorph A), L-tartrate salt (polymorph B) and succinate salt (Polymorph A).

| | Free base (Polymorph B) | | | | Hydrochloride salt (Polymorph A, anhydrate) | | L-tartrate salt (Polymorph B, anhydrate) | | Succinate salt Polymorph A (anhydrate) | |
|---|---|---|---|---|---|---|---|---|---|---|
| | $1^{st}$ Sorp. (%) | $1^{st}$ Desorp. (%) | $2^{nd}$ Sorp. (%) | $2^{nd}$ Desorp. (%) | Sorp. (%) | Desorp. (%) | Sorp. (%) | Desorp. (%) | Sorp. (%) | Desorp. (%) |
| 0% | // | 0.02 | 0.02 | // | 0.00 | 0.01 | 0.04 | 0.01 | 0.06 | 0.00 |
| 10% | // | 0.20 | 0.002 | // | 0.01 | 0.01 | 0.06 | 0.03 | 0.06 | 0.01 |

TABLE 10-continued

DVS test at 25° C. of HCl salt (polymorph A), L-tartrate salt (polymorph B) and succinate salt (Polymorph A).

| | Free base (Polymorph B) | | | | Hydrochloride salt (Polymorph A, anhydrate) | | L-tartrate salt (Polymorph B, anhydrate) | | Succinate salt Polymorph A (anhydrate) | |
|---|---|---|---|---|---|---|---|---|---|---|
| | $1^{st}$ | $1^{st}$ | $2^{nd}$ | $2^{nd}$ | | | | | | |
| | Sorp. (%) | Desorp. (%) | Sorp. (%) | Desorp. (%) | Sorp. (%) | Desorp. (%) | Sorp. (%) | Desorp. (%) | Sorp. (%) | Desorp. (%) |
| 20% | // | 6.07 | 0.007 | // | 0.01 | 0.012 | 0.08 | 0.07 | 0.07 | 0.01 |
| 30% | // | 6.29 | 0.02 | // | 0.01 | 0.03 | 0.10 | 0.10 | 0.07 | 0.02 |
| 40% | 8.34 | 8.54 | 0.02 | 8.23 | 0.01 | 0.03 | 0.12 | 0.13 | 0.07 | 0.02 |
| 50% | 8.83 | 8.90 | 0.04 | 8.76 | 0.01 | 0.04 | 0.13 | 0.19 | 0.09 | 0.02 |
| 60% | 8.90 | 8.90 | 0.06 | 8.79 | 0.02 | 0.04 | 0.15 | 0.29 | 0.08 | 0.03 |
| 70% | 8.96 | 8.97 | 0.12 | 8.87 | 0.03 | 0.04 | 0.19 | 0.48 | 0.09 | 0.10 |
| 80% | 9.02 | 9.03 | 3.80 | 8.95 | 0.05 | 0.07 | 0.66 | 0.67 | 0.10 | 0.11 |
| 90% | 9.11 | 9.13 | 9.00 | 9.06 | 0.12 | 0.12 | 1.00 | 1.18 | 0.14 | 0.16 |
| 95% | 9.21 | 9.21 | 9.14 | 9.14 | 0.19 | 0.19 | 1.60 | 1.60 | 0.29 | 0.29 |
| Hygroscopicity | Polymorph B is slightly hygroscopic but undergoes dehydration below 40% RH at 25° C. | | | | Non-hygroscopic | | Slightly hygroscopic | | Non-hygroscopic | |
| XRPD after DVS test | No form and crystallinity change | | | | No form and crystallinity change | | No form and crystallinity change | | No form and crystallinity change | |

The free base (Polymorph B) is stable from 40% RH to 95% RH. However, it undergoes dehydration when relative humidity is below 40% and converts to a potential anhydrate (polymorph A) after the dehydration. The dehydration product is stable from 0% RH to 70% RH. When RH>70%, the dehydration product absorbs water and restores water content in 90% RH. As a result, it converts back to free base (polymorph B). The hydrochloride salt (polymorph A) is non-hygroscopic. It absorbs about 0.17% water from 40% RH to 95% RH at 25° C. No form changes after the DVS test. The L-tartrate salt (polymorph B) is slightly hygroscopic. It absorbs about 1.5% water from 40% RH to 95% RH at 25° C. No form changes after the DVS test. The succinate salt (Polymorph A) is non-hygroscopic. It absorbs about 0.21% water from 40% RH to 95% RH at 25° C. No form changes after the DVS test. Thus, the HCl salt (polymorph A) and the succinate salt (polymorph A) appear to be most promising salt candidates based on hygroscopicity.

Morphic Properties

The free base (polymorph B) consists of plate shaped crystals with particle size ranging from ~10 to ~100 μm. The hydrochloride salt (polymorph A) consists of aggregated tiny crystals with particle size ranging from ~2 to ~30 μm. The L-tartrate (polymorph B) consists of aggregated tiny crystals with particle size ranging from ~2 to ~20 μm. The succinate salt (polymorph A) consists of rod-like crystals with particle sizes ranging from ~5 to ~50 μm.

Polymorphism

In the salt screening, two polymorphs of the L-tartrate salt (polymorph A and polymorph B) were identified; one polymorph of the succinate salt (polymorph A) was identified. One polymorph of the hydrochloride salt (polymorph A) was identified. Thus, from the number of polymorphs identified, the succinate salt and the HCl salt appear the most promising salt candidates based on the formation of a single polymorph from the screened solvents.

Conclusion

Above all, the free base has some drawbacks in its technical developability, including a very low melting point and physical instability under stress conditions. The three salt candidates well solved these developability issues of the free base. They are of high crystallinity and in high melting points. They are chemically and physically stable and non- or slightly, hygroscopic. All the three salts show good solubility in pH buffers and bio-relevant fluids. It was also found that the salt formation provided a purification effect. Based on these, all the three salts have better developability than the free base. In overall properties, the succinate and HCl salts were the most promising salt candidates. The succinate salt may offer some additional benefits over the HCl salt in terms of formulation due to the free additional carboxylic acid that may provide increased buffer capacity in aqueous solutions.

Example 5: Screening for Other Polymorph Forms of the Mono-Succinate Salt of (5)-3-(2,5-dimethoxy-4-(trifluoromethyl)phenyl)piperidine Equilibration with Solvents Solvent mediated equilibration is an accepted form of generating new polymorphs. Based on approximate solubility results, about 50 mg of succinate salt (Polymorph A) of (S)-3-(2,5-dimethoxy-4-(trifluoromethyl)phenyl)piperidine was equilibrated in solvents at 25° C. for 2 weeks, 50° C. for 1 week or under a temperature cycle between 5° C. to 50° C. at a heating/cooling rate of 0.1° C./min for 10 cycles with a stirring bar on a magnetic stirring plate at a rate of 400 rpm. Obtained suspensions were filtered through a 0.45 μm nylon membrane filter by centrifugation at 14,000 rpm. Solid parts (wet cakes) were investigated by XRPD.

TABLE 11

| Solvent mediated equilibration succinate salt (Polymorph A) of (S)-3-(2,5-dimethoxy-4-(trifluoromethyl)phenyl)piperidine. | | | |
|---|---|---|---|
| Solvents | Polymorph 25° C. (2 weeks) | Polymorph 50° C. (1 week) | Polymorph 5° C. to 50° C. |
| Water | A | A | A |
| Methanol | A | A | A |
| Ethanol | A | A | A |
| 2-Propanol | A | A | A |
| Acetone | A | A | A |
| Methyl ethyl ketone | A | A | A |
| Acetonitrile | A | A | A |
| Ethyl acetate | A | A | A |
| Isopropyl acetate | A | A | A |
| t-Butyl methyl ether | A | A | A |
| 1,4-Dioxane | A | A | A |
| Tetrahydrofuran | A | A | A |
| Toluene | A | A | A |
| Dichloromethane | A | A | A |
| Ethanol/water (80:20, v/v) | A | A | A |
| IPA/water (85:15, v/v) | A | A | A |
| Acetone/water (35:65, v/v) | A | A | A |
| Acetonitrile/water (50:50, v/v) | A | A | A |
| Tetrahydrofuran/water (87:13, v/v) | A | A | A |
| 1,4-Dioxane/water (84:16, v/v) | A | A | A |

Crystallization at Room Temperature by Slow or Fast Evaporation

Based on approximate solubility results, about 30 mg of the succinate salt (Polymorph A) of (S)-3-(2,5-dimethoxy-4-(trifluoromethyl)phenyl)piperidine was dissolved in the solvents shown in Table 12. Obtained solutions were filtered through a 0.45 μm nylon membrane. Obtained clear solutions were slowly evaporated in ambient condition (about 25° C., 50% RH), fast evaporated at room temperature under a dry nitrogen flow. Solid residues were investigated by XRPD.

TABLE 12

| Crystallization solvents and isolated polymorph. | | |
|---|---|---|
| Solvents | Polymorph (Slow evaporation rt.) | Polymorph (Fast evaporation rt.) |
| Water | A | A |
| Methanol | A | A |
| Ethanol | A | A |
| 2-Propanol | A | A |
| Acetone/water (20:1, v/v) | A | A |
| Acetonitrile/water (20:1, v/v) | A | A |

TABLE 12-continued

| Crystallization solvents and isolated polymorph. | | |
|---|---|---|
| Solvents | Polymorph (Slow evaporation rt.) | Polymorph (Fast evaporation rt.) |
| Tetrahydrofuran | Not performed (oil) | A |
| Ethyl acetate/DCM (1:1, v/v) | A | A |
| EtOH/DCM (1:1, v/v) | A | A |
| MeOH/DCM (1:1, v/v) | A | A |
| Acetone/DCM (1:1, v/v) | Not performed (gel) | A |

Crystallization from Hot Saturated Solutions by Slow or Fast Cooling

Based on approximate solubility results, about 50 mg of the succinate salt (Polymorph A) of (M)-3-(2,5-dimethoxy-4-(trifluoromethyl)phenyl)piperidine was dissolved in the minimal amount of selected solvents shown in Table 13 at 50° C. Obtained solutions were filtered through a 0.45 μm nylon membrane. The obtained clear solutions were cooled to 5° C. at 0.1° C./min (slow cooling) or the obtained clear solutions were put into a 0° C. ice bath and agitated (fast cooling). Precipitates were collected by centrifugation filtration through a 0.45 μm nylon membrane filter at 14,000 rpm at 5° C. Solid parts (wet cakes) were be investigated by XRPD.

TABLE 13

| Crystallization solvents and isolated polymorph. | | |
|---|---|---|
| Solvents | Polymorph (Slow cooling) | Polymorph (Fast cooling) |
| Methanol | A | A |
| Ethanol | A | A |
| MeOH/DCM (1:1, v/v) | A | A |
| EtOH/DCM (1:1, v/v) | A | A |
| MeOH/ACN (2:1, v/v) | A | A |
| Acetone/water (20:1, v/v) | A | A |
| ACN/water (20:1, v/v) | A | A |
| THF | A | A |
| EtOH/EA (3:1, v/v) | A | A |

Crystallization by Addition of Anti-Solvent

Based on approximate solubility results, about 50 mg of the succinate salt (Polymorph A) of (S)-3-(2,5-dimethoxy-4-(trifluoromethyl)phenyl)piperidine was dissolved in the minimal amount of selected good solvents at ambient temperature (about 25° C.). 2-4 folds of anti-solvent was added into the obtained clear solutions slowly until a large amount of solids precipitated out. Precipitates were collected by centrifugation filtration through a 0.45 m nylon membrane filter at 14,000 rpm. Solid parts (wet cakes) were investigated by XRPDP.

TABLE 14

| Crystallization solvents and isolated polymorph. | | | |
|---|---|---|---|
| Solvents (mL)p | Anti-solvent (mL) | Polymorph | Comments |
| Water (1.5) | ACN (6.0) | // | Clear solution<br>Cooled to 5° C. → cooled to −20° C. |
| MeOH (0.4) | MTBE (1.6) | A | — |
| MeOH (0.4) | Toluene (1.6) | // | Clear solution<br>Cooled to 5° C. → cooled to −20° C. |
| EtOH (2.0) | Heptane (4.0) | A | — |
| EtOH (2.0) | MTBE (8.0) | A | Cooled to 5° C. → cooled to −20° C. |
| EtOH (2.0) | Toluene (8.0) | // | Clear solution<br>Cooled to 5° C. → cooled to −20° C. |

TABLE 14-continued

| Crystallization solvents and isolated polymorph. | | | |
|---|---|---|---|
| Solvents (mL)p | Anti-solvent (mL) | Polymorph | Comments |
| THF (4.0) | Toluene (16.0) | // | Clear solution<br>Cooled to 5° C. → cooled to −20° C. |
| 1,4-dioxane/water (0.3) | Toluene (1.2) | // | Clear solution<br>Cooled to 5° C. → cooled to −20° C. |

//: Not carried out

Compression Simulation Experiments

About 100 mg of succinate the salt of (S)-3-(2,5-dimethoxy-4-(trifluoromethyl)phenyl)piperidine (Polymorph A) was compressed for 5 minutes under 2 MPa, 5 MPa and 10 MPa with a hydraulic press. Potential change of polymorph form and degree of crystallinity were evaluated by XRPD as shown in Table 15.

TABLE 15

| Compression simulation experiments | | |
|---|---|---|
| Pressure (MPa) | Polymorph | Comments |
| 2 | A | No change in crystallinity or polymorph |
| 5 | A | No change in crystallinity or polymorph |
| 10 | A | No change in crystallinity or polymorph |

Dry Grinding Simulation Experiments

About 50 mg of the succinate salt of (S)-3-(2,5-dimethoxy-4-(trifluoromethyl)phenyl)piperidine (Polymorph A) was ground manually with a mortar and a pestle for 5 min. Potential change of polymorph form and degree of crystallinity were evaluated by XRPD. No change in polymorph form and crystallinity was observed.

Wet Granulation Simulation Experiments

Water or ethanol were added dropwise to about 50 mg the succinate salt (Polymorph A) of (S)-3-(2,5-dimethoxy-4-(trifluoromethyl)phenyl)piperidine until the sample was wetted sufficiently. Wet samples were ground gently with a mortar and pestle. Post granulation samples were dried under ambient condition for 10 min. Potential change of polymorph form and degree of crystallinity were evaluated by XRPD. No change in polymorph form and crystallinity was observed.

Conclusion

The results show that polymorph A is the only identified polymorph of the mono-succinate salt of (S)-3-(2,5-dimethoxy-4-(trifluoromethyl)phenyl)piperidine. The data indicates that the polymorph is highly stable and that spontaneous conversion of polymorph A, during storage or formulation, into other polymorph forms are highly unlikely. Polymorph A has high crystallinity, good chemical and physical stability, non-hygroscopicity and good tolerance to formulation processes. Therefore, polymorph A is an optimal polymorph for development.

The invention claimed is:

1. A method for the manufacture of a compound of Formula (VI) comprising the steps of:

a) reacting the compound of Formula (III), (III)

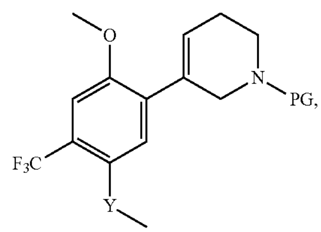

wherein Y is selected from S or O; PG is an amine protecting group selected from fluorenylmethoxycarbonyl (Fmoc), tert-butyloxycarbonyl (Boc), benzyloxycarbonyl (Cbz), acetyl (Ac), trifluoroacetyl ($CF_3CO$), benzyl (Bn) or 4-methoxybenzyl (PMB); trityl (Tr), or tosyl (Ts), in a solvent with hydrogen gas ($H_2$) in the presence of a transition metal catalyst selected from palladium/charcoal (Pd/C), $PtO_2$, a palladium complex, a rhodium complex, a ruthenium complex, or an iridium complex to obtain a racemic compound of Formula (IVa) or (IVb)

(IVa)

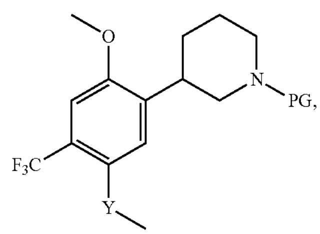

(IVb)

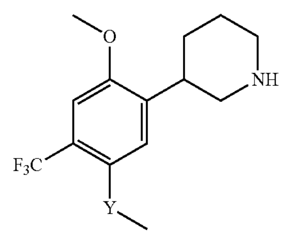

or, alternatively, reacting the compound of Formula (III) in a solvent, with a deprotection reagent to obtain a compound of Formula (IIIa)

(IIIa)

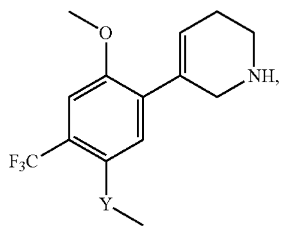

b) reacting the compound of Formula (IVa), if formed in step a), in a solvent with a deprotection reagent to obtain a racemic compound of Formula (IVb), or, alternatively, reacting the compound of Formula (IIIa), if formed in step a), in a solvent, with hydrogen gas ($H_2$) in the presence of a transition metal catalyst selected from palladium/charcoal (Pd/C), $PtO_2$, a palladium complex, a rhodium complex, a ruthenium complex, or an iridium complex, to obtain a racemic compound of Formula (IVb)

(IVb)

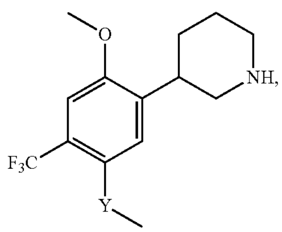

c) reacting a compound of Formula (IVb) with a chiral acid in a solvent to obtain a compound of Formula (V) having an enantiomeric excess (ee) of at least 70%, (V)

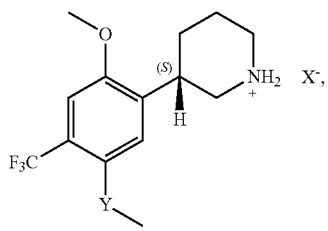

wherein $X^-$ is the conjugate base of the chiral acid, and liberating the salt of Formula (V) to obtain the compound of Formula(S)-(IVb)

(S)-(IVb)

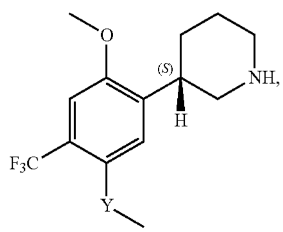

d) reacting the compound of Formula(S)-(IVb) in a solvent with succinic acid, L-tartaric acid, or HCl to obtain a crystalline compound of Formula (VI), (VI)

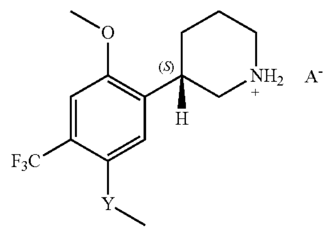

wherein $A^-$ is selected from 3-carboxypropanoate, (2R,3R)-3-carboxy-2,3-dihydroxypropanoate or chloride ($Cl^-$).

2. The method according to claim 1, wherein the chiral acid in step c) is selected from (−)-O,O'-Di-p-toluoyl-L-tartaric acid or (−)-Di-p-anisoyl-L-tartaric acid.

3. The method according to claim 1, wherein the transition metal catalyst is palladium/charcoal (Pd/C).

4. The method according to claim 1, wherein the solvent in the hydrogenation, in step a) or b), comprises EtOAc.

5. The method according to claim 1, wherein the solvent, in the chiral resolution in step c) comprises THF, ACN, IPA, or MTBE and optionally further $H_2O$ as co-solvent.

6. The method according to claim 5, wherein the solvent comprises THF and $H_2O$ as co-solvent.

7. A method for the manufacture of a compound of Formula (VI), comprising the steps of:

a) reacting the compound of Formula (III), (III)

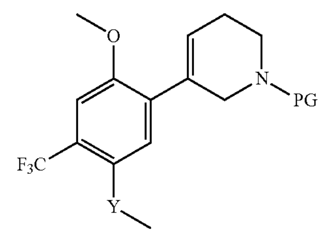

wherein Y is selected from S or O; PG is an amine protecting group selected from fluorenylmethoxycarbonyl (Fmoc), tert-butyloxycarbonyl (Boc), benzyloxycarbonyl (Cbz), acetyl (Ac), trifluoroacetyl ($CF_3CO$), benzyl (Bn) or 4-methoxybenzyl (PMB); trityl (Tr), or tosyl (Ts), in a solvent with hydrogen gas ($H_2$) in the presence of a transition metal catalyst, and a chiral ligand, wherein the transition metal catalyst is selected from a palladium complex, a rhodium complex, a ruthenium complex, or an iridium complex, to obtain a compound of Formula(S)-(IVa) or(S)-(IVb), having an enantiomeric excess (% ee) of at least 70%, (S)-(IVa)

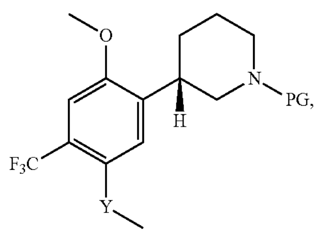

(S)-(IVb)

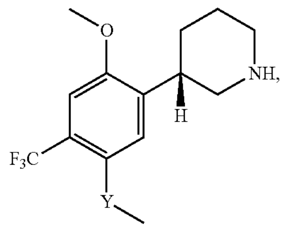

or reacting the compound of Formula (III) in a solvent, with a deprotection reagent to obtain a compound of Formula (IIIa)

(IIIa)

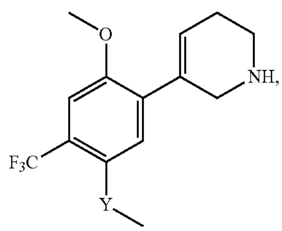

b) reacting the compound of Formula(S)—(IVa), if formed in step a), in a solvent with a deprotection reagent to obtain a compound of Formula(S)-(IVb) having an enantiomeric excess (% ee) of at least 70%, or alternatively, reacting the compound of Formula (IIIa), if formed in step a), in a solvent with hydrogen gas ($H_2$) in the presence of a transition metal catalyst and a chiral ligand, wherein the transition metal catalyst is selected from a palladium complex, a rhodium complex, a ruthenium complex, or an iridium complex, to obtain a compound of Formula(S)-(IVb), having an enantiomeric excess (% ee) of at least 70%, (S)-(IVb)

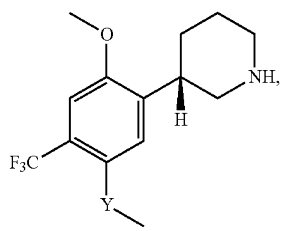

c) reacting the compound of Formula(S)-(IVb) in a solvent with succinic acid, L-tartaric acid, or HCl to obtain a crystalline compound of Formula (VI), (VI)

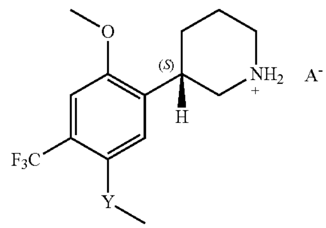

wherein $A^-$ is selected from 3-carboxypropanoate, (2R,3R)-3-carboxy-2,3-dihydroxypropanoate or chloride ($Cl^-$).

8. The method according to claim 1, wherein the amine protecting group is tert-butyloxycarbonyl (Boc) and the deprotection reagent is an acid.

9. The method according to claim 1, wherein the solvent, in the deprotection in step a) or b), comprises EtOAc or 2-Me-THF.

10. The method according to claim 7, wherein the organic solvent in the asymmetric hydrogenation, in step a) or b), comprises EtOH.

11. The method according to claim 1, wherein the solvent, in the crystallization with succinic acid, L-tartaric acid, or HCl, comprises ACN, EtOH, or Acetone.

12. The method according to claim 11, wherein the solvent comprises EtOH.

13. The method according to claim 7, wherein the chiral ligand is (R,R)-i-Pr-DuPhos.

14. The method according to claim 7, wherein transition metal catalyst is a rhodium complex.

15. A crystalline compound of Formula (VI), (VI)

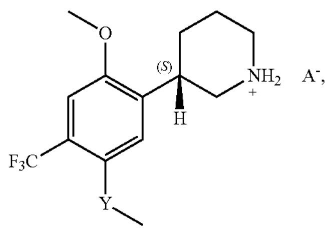

wherein $A^-$ is 3-carboxypropanoate and the crystalline compound is the polymorph with the XRPD spectrum having 2θ peaks 4.077°, 8.108°, 11.991°, 12.156°, 13.893°, 15.876°, 16.218°, 16.412, 16.596°, 17.849°, 19.507°, 19.786°, 20.031°, 20.297°, 21.122°, 22.011°, 22.635°, 23.000°, 23.268°, 24.065°, 24.408°, 25.414°, 25.758°, 26.947°, 27.751°, 28.032°, 28.314°, 29.966°, 30.358°, 30.562°, 30.770°, 31.378°, 32.306°, 32.868°, 33.505°, 34.710°, 35.206°, 36.418°, 36.714°, 37.306°, 38.147°, 38.322°, 38.745°, when measured with a radiation wavelength of λ=1.5418 Å, or $A^-$ is (2R,3R)-3-carboxy-2,3-dihydroxypropanoate and the crystalline compound is the polymorph with the XRPD spectrum having 2θ peaks 5.925°, 10.183°, 11.313°, 11.823°, 12.209°, 12.542°, 15.233°, 15.592°, 15.776°, 16.275°, 16.719°, 17.063°, 17.406°, 17.752°, 18.012°, 19.568°, 19.692°, 20.291°, 20.746°, 21.261°, 21.839°, 22.200°, 22.700°, 23.226°, 23.372°, 23.603°, 23.962°, 24.516°, 24.707°, 25.013°, 25.440°, 25.914°, 26.502°, 27.003°, 27.496°, 27.902°, 28.365°, 28.786°, 29.078°, 29.791°, 30.027°, 30.299°, 30.785°, 31.187°, 31.686°, 32.070°, 32.392°, 33.434°, 33.862°, 34.358°, 34.790°, 35.584°, 36.277°, 36.801°, 37.197°, 38.121° and 39.667°, when measured with a radiation wavelength of λ=1.5418 Å, or $A^-$ is selected as chloride ($Cl^-$) and the crystalline compound is the polymorph with the XRPD spectrum having 2θ peaks 7.457°, 9.185°, 10.899°, 11.738°, 12.604°, 14.956°, 17.706°, 18.215°, 18.382°, 19.307°, 19.902°, 20.442°, 20.956°, 21.850°, 22.449°, 23.781°, 24.007°, 24.357°, 24.752°, 25.327°, 25.557°, 26.064°, 27.377°, 27.702°, 28.340°, 28.557°, 29.144°, 29.366°, 29.915°, 30.164°, 30.669°, 30.975°, 32.213°, 32.725°, 33.018°, 33.742°, 34.605°, 35.012°, 35.618°, 36.883°, 37.131°, 37.250°, 37.772°, 38.358°, 38.626°, 39.140°, 39.869°, when measured with a radiation wavelength of λ=1.5418Å.

16. The crystalline compound according to claim 15, wherein $A^-$ is 3-carboxypropanoate and the salt is the polymorph with the XRPD spectrum having 2θ peaks 4.077°, 8.108°, 11.991°, 12.156°, 13.893°, 15.876°, 16.218°, 16.412, 16.596°, 17.849°, 19.507°, 19.786°, 20.031°, 20.297°, 21.122°, 22.011°, 22.635°, 23.000°, 23.268°, 24.065°, 24.408°, 25.414°, 25.758°, 26.947°, 27.751°, 28.032°, 28.314°, 29.966°, 30.358°, 30.562°, 30.770°, 31.378°, 32.306°, 32.868°, 33.505°, 34.710°, 35.206°, 36.418°, 36.714°, 37.306°, 38.147°, 38.322°, 38.745°, when measured with a radiation wavelength of λ=1.5418Å.

17. An intermediate compound of Formula (III) or (IIIa), (III)

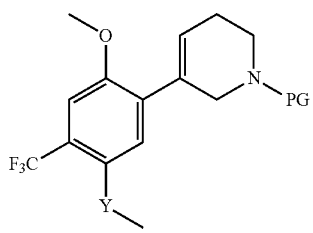

(IIIa)

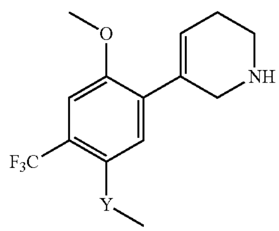

wherein Y is selected from O or S, PG is selected from fluorenylmethoxycarbonyl (Fmoc), tert-butyloxycarbonyl (Boc), benzyloxycarbonyl (Cbz), acetyl (Ac), trifluoroacetyl ($CF_3CO$), benzyl (Bn) or 4-methoxybenzyl (PMB); trityl (Tr), or tosyl (Ts).

18. The intermediate compound according to claim 17, wherein the amine protecting group is tert-butyloxycarbonyl (Boc).

19. The intermediate compound according to claim 17, wherein Y is O.

20. A method of manufacturing a compound having the structure of Formula (IVa), Formula (IVa)

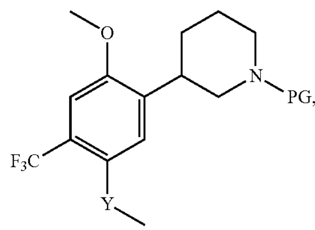

Formula (IVb)

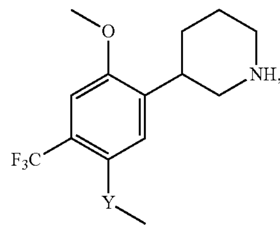

Formula (S)-(IVa)

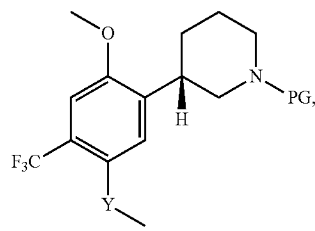

Formula (S)-(IVb)

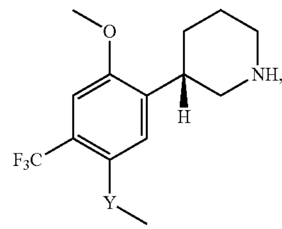

Formula (V)

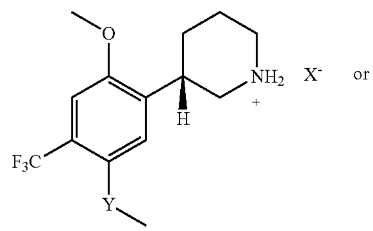

or

Formula (VI)

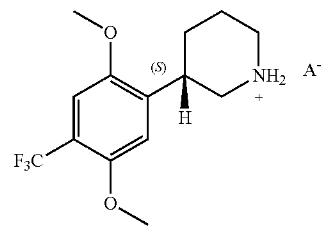

comprising a step of using the intermediate compound of claim 17.

21. The method according to claim 7, wherein the amine protecting group is tert-butyloxycarbonyl (Boc) and the deprotection reagent is an acid.

22. The method according to claim 7, wherein the solvent, in the deprotection in step a) or b), comprises EtOAc or 2-Me-THF.

23. The method according to claim 7, wherein the solvent, in the crystallization with succinic acid, L-tartaric acid, or HCl, comprises ACN, EtOH, or Acetone.

* * * * *